United States Patent
Marrichi et al.

(10) Patent No.: US 10,227,416 B2
(45) Date of Patent: Mar. 12, 2019

(54) METHODS AND COMPOSITION FOR SECRETION OF HETEROLOGOUS POLYPEPTIDES

(71) Applicant: Genentech, Inc., South San Francisco, CA (US)

(72) Inventors: Matthew Marrichi, Needham, MA (US); Dorothea E. Reilly, San Francisco, CA (US)

(73) Assignee: GENENTECH, INC., South San Francisco, CA (US)

( * ) Notice: Subject to any disclaimer, the term of this patent is extended or adjusted under 35 U.S.C. 154(b) by 0 days.

(21) Appl. No.: 14/250,268

(22) Filed: Apr. 10, 2014

(65) Prior Publication Data
US 2014/0371429 A1 Dec. 18, 2014

Related U.S. Application Data

(60) Continuation of application No. 13/722,398, filed on Dec. 20, 2012, now Pat. No. 8,735,098, which is a division of application No. 12/940,825, filed on Nov. 5, 2010, now Pat. No. 8,361,744.

(60) Provisional application No. 61/258,565, filed on Nov. 5, 2009.

(51) Int. Cl.
| | | |
|---|---|---|
| *A61K 49/00* | (2006.01) | |
| *C12N 15/67* | (2006.01) | |
| *C12N 15/70* | (2006.01) | |
| *C07K 16/00* | (2006.01) | |
| *C07K 16/30* | (2006.01) | |

(52) U.S. Cl.
CPC .............. *C07K 16/30* (2013.01); *C07K 16/00* (2013.01); *C12N 15/67* (2013.01); *C12N 15/70* (2013.01); *A61K 49/0058* (2013.01); *C07K 2317/14* (2013.01); *C07K 2319/02* (2013.01)

(58) Field of Classification Search
None
See application file for complete search history.

(56) References Cited

U.S. PATENT DOCUMENTS

| | | | |
|---|---|---|---|
| 5,747,662 A | 5/1998 | Simmons et al. | |
| 5,849,576 A * | 12/1998 | Skerra et al. | 435/320.1 |
| 6,242,177 B1 | 6/2001 | Simmons et al. | |
| 6,979,556 B2 | 12/2005 | Simmons et al. | |
| 7,615,529 B2 * | 11/2009 | Kong-Beltran et al. | 514/1.1 |
| 8,361,744 B2 | 1/2013 | Marrichi et al. | |
| 8,536,118 B2 | 9/2013 | Kong-Beltran et al. | |
| 8,735,098 B2 | 5/2014 | Marrichi et al. | |
| 2003/0073164 A1 * | 4/2003 | Simmons et al. | 435/69.1 |
| 2005/0032173 A1 | 2/2005 | Rojas | |
| 2005/0227324 A1 * | 10/2005 | Huang et al. | 435/69.1 |
| 2005/0271654 A1 * | 12/2005 | Rinderknecht et al. | 424/141.1 |
| 2006/0270594 A1 | 11/2006 | Kong-Beltran et al. | |
| 2007/0015244 A1 | 1/2007 | Simmons et al. | |
| 2007/0128111 A1 | 6/2007 | Reilly et al. | |
| 2009/0226443 A1 | 9/2009 | Filvaroff et al. | |
| 2010/0028337 A1 | 2/2010 | Kong-Beltran et al. | |
| 2010/0144546 A1 * | 6/2010 | Delisa et al. | 506/10 |
| 2011/0111408 A1 | 5/2011 | Marrichi et al. | |
| 2012/0089541 A1 | 4/2012 | Patel et al. | |
| 2013/0004484 A1 | 1/2013 | Demeule et al. | |
| 2013/0078252 A1 | 3/2013 | Wilson et al. | |
| 2013/0096280 A1 | 4/2013 | Marrichi et al. | |
| 2013/0129718 A1 | 5/2013 | Wong et al. | |
| 2014/0037625 A1 | 2/2014 | Patel et al. | |
| 2015/0050275 A1 | 2/2015 | Wong et al. | |
| 2015/0056207 A1 | 2/2015 | Filvaroff et al. | |
| 2015/0064191 A1 | 3/2015 | Demeule et al. | |
| 2015/0125452 A1 | 5/2015 | Wilson et al. | |

FOREIGN PATENT DOCUMENTS

| | | |
|---|---|---|
| CN | 1154736 C | 6/2004 |
| EP | 1 356 052 B1 | 10/2003 |
| EP | 1 908 769 | 4/2008 |
| JP | 337590 B2 | 2/2003 |
| JP | 2004-530419 A | 10/2004 |
| JP | 2005-517385 A | 6/2005 |
| JP | 2007-508032 A | 4/2007 |
| JP | 2008-504007 A | 2/2008 |
| JP | 2009-500027 A | 1/2009 |
| RU | 2287574 C2 | 11/2006 |
| WO | 96/27016 | 9/1996 |
| WO | WO-02/48376 A2 | 6/2002 |
| WO | WO-02/48376 A3 | 6/2002 |
| WO | 02/061090 A2 | 8/2002 |
| WO | WO-03/018771 A2 | 3/2003 |
| WO | 2005/038031 | 4/2005 |
| WO | 2005/063816 A2 | 7/2005 |
| WO | WO-2006/042158 A2 | 4/2006 |

(Continued)

OTHER PUBLICATIONS

Andersen et al., "Production technologies for monoclonal antibodies and their fragments" Curr. Op. Biotechnol. 15:456-462 (2004).
Jackson et al., "Effects of Toluene on *Escherichia coli*" Journal of Bacteriology 90(5):1420 ( 1965).
Kadokura et al., "Detecting Folding Intermediates of a Protein as it Passes through the Bacterial Translocation Channel" Cell 138:1164 (Sep. 2009).
Karamyshev et al., "Processing of *Escherichia* coli Alkaline Phosphatase: Role of the Primary Structure of the Signal Peptide Cleavage Region" J. Mol. Biol, 277:859-870 ( 1998).
Kipriyanov and Little, "Generation of Recombinant Antibodies" Mol. Biotech. 12:173-201 (1999).
Le Calvez et al., "Increased Efficiency of Alkaline Phosphatase Production Levels in *Escherichia coli* Using a Degenerate PelB Signal Sequence" Gene 170:51 ( 1996).

(Continued)

*Primary Examiner* — Addison D Ault
(74) *Attorney, Agent, or Firm* — Morrison & Foerster LLP

(57) ABSTRACT

The present invention relates generally to the fields of molecular biology and protein technology. More specifically, the invention concerns signal sequences for the secretion of heterologous polypeptide from bacteria. The invention also concerns recombinant polypeptides and uses thereof.

184 Claims, 7 Drawing Sheets
Specification includes a Sequence Listing.

(56) References Cited

FOREIGN PATENT DOCUMENTS

| WO | WO-2006/042158 A3 | 4/2006 |
| WO | WO-2007/006665 A1 | 1/2007 |
| WO | 2009/021548 | 2/2009 |
| WO | WO-2011/057120 A1 | 5/2011 |

OTHER PUBLICATIONS

Marrichi et al., "Food, Pharmaceutical & Bioengineering Divisiona (185c) Periplasmic Expression of Full-Length Antibodies and /Antibody Derivatives in *Escherichia Coli* Via Multiple Translocation Pathways" Abstract 09AIChEAnnual Meeting, Nashville, TN, ( Nov. 10, 2009).

Marrichi et al., "Genetic Toggling of lkaline Phosphatase Folding Reveals Signal Peptides for all Major Modes of Transport Across the Inner Membrane of Bacteria" The Journal of Biological Chemistry 283(50):35223 (Dec. 2008).

Martens et al., "A novel one-armed anti-c met antibody inhibits glioblastoma growth in vivo" Clin Cancer Res 12(20):6144-6152 (Oct. 2006).

Natale et al., "Sec- and tat-mediated Protein Secretion Across the Bacterial Cytoplasmic Membrane-Distinct translocases and Mechanisms" Biochimica et Biophysica Acta 1778:1735 ( 2008).

PCT/US2010/055702 International Search Report, dated Jan. 26, 2011.

Pluckthun and Pack, "New Protein Engineering Approaches to Multivalent and Bispecific Antibody Fragments" Immunotechnology 3:83-105 (Jun. 1997).

Rakestraw et al., "Directed Evolution of a Secretory Leader for the Improved Expression of Heterologous Proteins and Full-Length Antibodies in *Saccharomyces cerevisiae*" Biotechnology and Bioengineering 103(6):1192 (Aug. 2009).

Schwall et al., "Inhibition of cMet activation by a one-armed antibody" Proceedings of the American Association for Cancer Research (Abstract #1424) 45:327 (Mar. 2004).

Simmons and Yansura, "Translational level is a critical factor for the secretion of heterologous proteins in *Escherichia coli*" Nat Biotechnol 14:629-634 (May 1996).

Simmons et al., "Expression of Full-length Immunoglobulins in *Escherichia coli*: Rapid and Efficient Production of Aglycosylated Antibodies" Journal of Immunological Methods 263:133 ( 2002).

Simmons et al., "Translational level is a critical factor for the secretion of heterologous proteins in *Escherichia coli*" Nature Biotech, 14(5):629-634 ( 1996).

Stemmer et al., "Increased Antibody Expression from *Escherichia coli* Throught wobble-base Library mutagenesis by Enzymatic Inverse PCR" Gene 123:1-7 ( 1993).

Thie et al., "SRP and SEC Pathway Leader Peptides for Antibody Phage Display and Antibody Fragment Production in *E. coli*" New Biotechnology 25(1):49 (Jun. 2008).

Vimberg et al., "Translation Initiation Region Sequence Preferences in *Escherichia coli*" MC Molecular Biology 8:100 (Oct. 2007).

\* cited by examiner

FIG. 7

5D5.v2 Light Chain
FR1-LC:   DIQMTQSPSSLSASVGDRVTITC
FR2-LC:   WYQQKPGKAPKLLIY
FR3-LC:   GVPSRFSGSGSGTDFTLTISSLQPEDFATYYC
FR4-LC:   FGQGTKVEIKR
CDR1-LC:  KSSQSLLYTSSQKNYLA
CDR2-LC:  WASTRES
CDR3-LC:  QQYYAYPWT
CL1:      TVAAPSVFIFPPSDEQLKSGTASVVCLLNNFYPREAKVQWKVDNALQSGNSQESVTEQDSK
          DSTYSLSSTLTLSKADYEKHKVYACEVTHQGLSSPVTKSFNRGEC

5D5.v2 Heavy Chain
FR1-HC:   EVQLVESGGGLVQPGGSLRLSCAAS
FR2-HC:   WVRQAPGKGLEWV
FR3-HC:   RFTISADTSKNTAYLQMNSLRAEDTAVYYC
FR4-HC:   WGQGTLVTVSS
CDR1-HC:  GYTFTSYWLH
CDR2-HC:  GMIDPSNSDTRFNPNFKD
CDR3-HC:  ATYRSYVTPLDY
CH1:      ASTKGPSVFPLAPSSKSTSGGTAALGCLVKDYFPEPVTVSWNSGALTSGVHTFPA
          VLQSSGLYSLSSVVTVPSSSLGTQTYICNVNHKPSNTKVDKKVEPKSCDKTHT
Fc:       CPPCPAPELLGGPSVFLFPPKPKDTLMISRTPEVTCVVVDVSHEDPEVKFNWYVDGVEVH
          NAKTKPREEQYNSTYRVVSVLTVLHQDWLNGKEYKCKVSNKALPAPIEKTISKAKGQPREP
          QVYTLPPSREEMTKNQVSLSCAVKGFYPSDIAVEWESNGQPENNYKTTPPVLDSDGSFFL
          VSKLTVDKSRWQQGNVFSCSVMHEALHNHYTQKSLSLSPGK

FIG. 8

DKTHTCPPCPAPELLGGPSVFLFPPKPKDTLMISRTPEVTCVVVDVSHED
PEVKFNWYVDGVEVHNAKTKPREEQYNSTYRVVSVLTVLHQDWLNGKE
YKCKVSNKALPAPIEKTISKAKGQPREPQVYTLPPSREEMTKNQVSLWCL
VKGFYPSDIAVEWESNGQPENNYKTTPPVLDSDGSFFLYSKLTVDKSRW
QQGNVFSCSVMHEALHNHYTQKSLSLSPGK

METHODS AND COMPOSITION FOR SECRETION OF HETEROLOGOUS POLYPEPTIDES

CROSS-REFERENCE TO RELATED APPLICATIONS

This application is a continuation application to U.S. patent application Ser. No. 13/722,398, filed on Dec. 20, 2012, now U.S. Pat. No. 8,735,098, issued on May 27, 2014, which is a divisional application to U.S. patent application Ser. No. 12/940,825, filed on Nov. 5, 2010, now U.S. Pat. No. 8,361,744, issued on Jan. 29, 2013, which claims priority to U.S. patent application No. 61/258,565, filed on Nov. 5, 2009, the contents of each of which are incorporated herein by reference in their entirety.

SEQUENCE LISTING

The instant application contains a Sequence Listing which has been submitted in ASCII format via EFS-Web and is hereby incorporated by reference in its entirety. Said ASCII copy, created on Apr. 9, 2014, is named P4386R1D1C1_SequenceListing.TXT and is 33,160 bytes in size.

FIELD OF THE INVENTION

The present invention relates generally to the fields of molecular biology and protein technology. More specifically, the invention concerns signal sequences for the secretion of heterologous polypeptides from bacteria. The invention also concerns prokaryotically produced recombinant polypeptides and uses thereof.

BACKGROUND OF THE INVENTION

Secretion of heterologous polypeptides into the periplasmic space of $E$ $coli$ and other prokaryotes or into their culture media is subject to a variety of parameters. Typically, vectors for secretion of a polypeptide of interest are engineered to position DNA encoding a secretory signal sequence 5' to the DNA encoding the polypeptide of interest.

Recent years have seen increasing promises of using heterologous polypeptide, for example, antibodies, as diagnostic and therapeutic agents for various disorders and diseases. Many research and clinical applications require large quantities of functional polypeptide, thus calling for scaled-up, yet economic systems for polypeptide production. Particularly useful is the recombinant production of antibodies using a variety of expression hosts, ranging from prokaryotes such as $E$. $coli$ or $B$. $subtilis$, to yeast, plants, insect cells and mammalian cells. Kipriyanov and Little (1999) *Mol. Biotech.* 12:173-201.

Compared to other polypeptide production systems, bacteria, particularly *E. coli*, provides many unique advantages. The raw materials used (i.e. bacterial cells) are inexpensive and easy to grow, therefore reducing the cost of products. Prokaryotic hosts grow much faster than, e.g., mammalian cells, allowing quicker analysis of genetic manipulations. Shorter generation time and ease of scaling up also make bacterial fermentation a more attractive means for large quantity protein production. The genomic structure and biological activity of many bacterial species including *E. coli* have been well-studied and a wide range of suitable vectors are available, making expression of a desirable antibody more convenient. Compared with eukaryotes, fewer steps are involved in the production process, including the manipulation of recombinant genes, stable transformation of multiple copies into the host, expression induction and characterization of the products. Pluckthun and Pack (1997) *Immunotech* 3:83-105.

Various approaches have been used to make recombinant polypeptides in bacteria. Recombinant proteins can be obtained from bacteria either through refolding of inclusion bodies expressed in the cytoplasm, or through expression followed by secretion to the bacterial periplasm. The choice between secretion and refolding is generally guided by several considerations. Secretion is usually the faster and more commonly used strategy for producing antibodies. Kipriyanov and Little (1999), supra.

Antibody expression in prokaryotic systems can be carried out in different scales. The shake-flask cultures (in the 2-5 liter-range) typically generate less than 5 mg/liter products. Carter et al. (1992) *Bio/Technology* 10:12-16 developed a high cell-density fermentation system in which high-level expression (up to 2 g/liter) of antibody fragments was obtained. The gram per liter titers of Fab' obtained by Carter et al. is due largely to higher cell densities resulting from the more precisely controlled environment of a fermentor than that of a simple shake flask. The system contains a dicistronic operon designed to co-express the light chain and heavy chain fragments. The dicistronic operon is under the control of a single *E. coli* phoA promoter which is inducible by phosphate starvation. Each antibody chain is preceded by the *E. coli* heat-stable enterotoxin II (stII) signal sequence to direct secretion to the periplasmic space.

For general reviews of antibody production in *E. coli*, see Pluckthun and Pack (1997) *Immunotech* 3:83-105; Pluckthun et al. (1996) in ANTIBODY ENGINEERING: A PRACTICAL APPROACH, pp 203-252 (Oxford Press); Pluckthun (1994) in HANDBOOK OF EXP PHARMCOL VOL 3: THE PHARMCOL OF MONOCLONAL ANTIBODIES, pp 269-315 (ed. M. Rosenberg and G. P. Moore; Springer-Verlag, Berlin).

Many biological assays (such as X-ray crystallography) and clinical applications (such as protein therapy) require large amounts of protein. Accordingly, a need exists for high yield yet simple systems for producing properly assembled, soluble and functional heterologous polypeptides, such as antibodies.

All references cited herein, including patent applications and publications, are incorporated by reference in their entirety.

SUMMARY OF THE INVENTION

The invention provides a novel means for increasing production of heterologous proteins comprising use of novel translational initiation region (TIR) variants, including TIR variants comprising co-translational secretion signal peptides (signal peptides that direct translocation in a co-translational manner) and/or TIR variants comprising post-translational secretion signal peptides (signal peptides that direct translocation in a post-translational manner). In addition, demonstrated herein is increased antibody production using vectors comprising antibody light chain operably linked to a TIR comprising a co- or post-translational secretion signal peptide and an antibody heavy chain operably linked to a TIR comprising a co-translational secretion signal peptide for peak expression. Novel TIR variants are also provided herein.

In one aspect, the invention provides variant translation initiation regions. In some embodiments, the variant comprises a variant translation initiation region (in some embodiments, a prokaryotic post-translational secretion signal sequence or a prokaryotic co-translational secretion signal sequence). In some embodiments, the variant comprises nucleic acid variants of a secretion signal sequence, such as PhoA, MalE, DsbA or STII. In some embodiments, the variant further comprises a MlaI, BssHII, or XbaI restriction site. In some embodiments, the variant comprises a translation initiation region variant comprising a sequence shown Table 2.

In one aspect, the invention provides variant secretion signal sequences. In some embodiments, the secretion signal sequence is a prokaryotic post-translational secretion signal sequence or a prokaryotic co-translational secretion signal sequence. In some embodiments, the secretion signal sequence is a eukaryotic post-translational secretion signal sequence or a eukaryotic co-translational secretion signal sequence. In some embodiments, the variants are nucleic acid variants of a PhoA, MalE, DsbA or STII secretion signalsequence. In some embodiments, the variants comprise a secretion signal sequence shown in Table 2. The variant secretion signal sequences of the invention are suitable for use, for example, in any of the methods disclosed herein.

In another aspect, the invention provides a polynucleotide comprising a translation initiation region of the invention. In some embodiments, the translation initiation region comprises sequence shown in Table 2 (e.g., one of SEQ ID NOs 1-42). In some embodiments, the translation initiation region comprises one of SEQ ID NOs. 1-14, 16-24, 26-39, 41-42. The polynucleotides are suitable for use, for example, in any of the methods disclosed herein.

In another aspect, the invention provides a polynucleotide comprising a secretion signal sequence of the invention. In some embodiments, the secretion signal sequence comprises sequence shown in Table 2. (e.g., one of SEQ ID NOs 1-42). In some embodiments, the translation initiation region comprises one of SEQ ID NOs. 1-14, 16-24, 26-39, 41-42. The polynucleotides are suitable for use, for example, in any of the methods disclosed herein.

In another aspect, the invention provides a polynucleotide comprising a translation initiation region of the invention operably linked to a polynucleotide encoding a heterologous polypeptide, whereby upon expression of the heterologous polypeptide in a host cell (e.g., a prokaryotic host cell, e.g., an *E. coli* host cell), the heterologous polypeptide is folded and assembled to form a biologically active heterologous polypeptide. Examples of heterologous polypeptides are further disclosed herein. In some embodiments, the heterologous polypeptide is an antibody heavy chain. In some embodiments, the heterologous polypeptide is an antibody light chain. In some embodiments, the heterologous polypeptide is an Fc polypeptide. In some embodiments, the heterologous polypeptide is a multimeric polypeptide. In some embodiments, the heterologous polypeptide is a heteromultimer. In some embodiments, the translation initiation region is any translation initiation region disclosed herein, e.g., a translation initiation region comprising sequence shown in Table 2. In some embodiments, the translation initiation region comprises sequence of one of SEQ ID NOs 1-42. In some embodiments, the translation initiation region comprises sequence of one of SEQ ID NOs 1-14, 36-39, 41-42. In some embodiments, the translation initiation region comprises a variant STII, DsbA, PhoA, or MalE signal sequence.

In another aspect, the invention provides a polynucleotide comprising (1) a first translation initiation region (TIR) operably linked to a polynucleotide encoding a first heterologous polypeptide, wherein the TIR comprises a co-translation prokaryotic secretion signal sequence; and (2) a second TIR operably linked to a polynucleotide encoding an second heterologous, wherein the second TIR comprises a co-translation or post-translation prokaryotic secretion signal sequence, whereby upon expression of the antibody in a host cell, the first and second heterologous polypeptides are folded and assembled to form a biologically active polypeptide complex.

In another aspect, the invention provides a polynucleotide encoding an antibody, said polynucleotide comprising (1) a first translation initiation region of the invention operably linked to a polynucleotide encoding an antibody heavy chain and (2) a second translation initiation region operably linked to a polynucleotide encoding an antibody light chain, whereby upon expression of the antibody in a host cell (e.g., a prokaryotic host cell, e.g., an *E. coli* host cell), the heavy and light chains are folded and assembled to form a biologically active antibody.

In some embodiments, the first translation initiation region comprises a co-translational prokaryotic secretion signal sequence (e.g., a signal sequence that directs translation through the signal recognition peptide). In some embodiments, the first translation initiation region comprises a STII or DsbA signal sequence. In some embodiments, the first translation initiation region comprises a DsbA signal sequence. In some embodiments, the first translation initiation region comprises a PhoA or MalE signal sequence. In some embodiments, the first translation initiation region comprises sequence of one of SEQ ID NOs: 1-10 and 36-42. In some embodiments, the first translation initiation region comprises sequence of one of SEQ ID NOs: 1-10 and 36-29 and 41 and 42. In some embodiments, the first translation initiation region comprises sequence of one of SEQ ID Nos 1-42. In some embodiments, the first translation initiation region comprises sequence of one of SEQ ID Nos. 1-14, 16-24, 26-39, 41-42.

In some embodiments, the second translation initiation region comprises (i) a co-translational prokaryotic secretion signal sequence or a post-translation prokaryotic secretion signal sequence (e.g., a signal sequence that directs translation through the sec pathway). In some embodiments, the second translation initiation region comprises a STII, DsbA, MalE or PhoA signal sequence. In some embodiments, the second translation initiation region comprises a PhoA or MalE signal sequence. In some embodiments, the second translation initiation region comprises sequence of one of SEQ ID NOs 1-42. In some embodiments, the second translation initiation region comprises sequence of one of SEQ ID NOs 1-14, 16-24, 26-39, 41-42.

In some embodiments, the polynucleotide encoding an antibody further comprises (3) a third translation initiation region operably linked to a polynucleotide encoding a Fc polypeptide. In some embodiments, the third translation initiation region comprises a STII, PhoA or DsbA signal sequence. In some embodiments, the third translation initiation region comprises a DsbA signal sequence. In some embodiments, the third translation initiation region comprises a PhoA signal sequence.

In another aspect, the invention provides polynucleotide comprising (1) a first translation initiation region (TIR) operably linked to a polynucleotide encoding an antibody heavy chain, wherein the TIR comprises a co-translation prokaryotic secretion signal sequence; and (2) a second TIR operably linked to a polynucleotide encoding an antibody light chain, wherein the second TIR comprises a co-translation or post-translation prokaryotic secretion signal sequence, whereby upon expression of the antibody in a host cell, the heavy and light chains are folded and assembled to form a biologically active antibody.

In another aspect, the invention provides a polynucleotide encoding an antibody fragment (such as a monovalent antibody fragment), said polynucleotide comprising (1) a first translation initiation region of the invention operably linked to a polynucleotide encoding an antibody heavy chain; (2) a second translation initiation region operably linked to a polynucleotide encoding an antibody light chain; and (3) a third translation initiation region operably linked to a polynucleotide encoding a Fc polypeptide, whereby upon expression of the antibody in a host cell (e.g., a prokaryotic host cell), the heavy chain, light chain and Fc polypeptide are folded and assembled to form a biologically active antibody (such as an one-armed antibody). In some embodiments, the third translation initiation region comprises a co-translational prokaryotic secretion signal sequence or a post-translational prokaryotic secretion signal sequence. In some embodiments, the third translation initiation region comprises a STII, PhoA, MalE, or DsbA signal sequence. In some embodiments, the third translation initiation region comprises a DsbA signal sequence. In some embodiments, the third translation initiation region comprises a PhoA signal sequence. In some embodiments, the third translation initiation region comprises sequence of one of SEQ ID Nos 1-42. In some embodiments, the third translation initiation region comprises sequence of one of SEQ ID Nos. 1-14, 16-24, 26-39, 41-42.

In another aspect, the invention provides a polynucleotide encoding an antibody, said polynucleotide comprising (1) a first translation initiation region of the invention operably linked to a polynucleotide encoding an antibody heavy chain, wherein the first translation initiation region comprises a STII or DsbA signal sequence and (2) a second translation initiation region operably linked to a polynucleotide encoding an antibody light chain, wherein the second translation initiation region comprises a STII, DsbA, MalE or PhoA signal sequence, whereby upon expression of the antibody in a host cell (e.g., a prokaryotic host cell), the light and heavy chains are folded and assembled to form a biologically active antibody. In some embodiments, the first translation initiation region comprises a DsbA signal sequence and the second translation initiation region comprises a MalE or PhoA signal sequence. In some embodiments, the polynucleotide encoding an antibody further comprises (3) a third translation initiation region operably linked to a polynucleotide encoding a Fc polypeptide. In some embodiments, the third translation initiation region comprises a STII, PhoA or DsbA signal sequence. In some embodiments, the third translation initiation region comprises a PhoA signal sequence. In some embodiments, the third translation initiation region comprises a DsbA signal sequence.

In some embodiments, the translational strength of said variant translation initiation region is less than the translational strength of the wild-type translation initiation region. In some embodiments, the translational strength of said variant translation initiation region is greater than the translational strength of the wild-type translation initiation region. In some embodiments, the amino acid sequence of the translation initiation variant is not altered relative to wild-type amino acid sequence. In some embodiments, the amino acid sequence of the translation initiation variant is altered relative to wild-type amino acid sequence. In some embodiments, the translation initiation region includes a prokaryotic secretion signal sequence. In some embodiments, the first and second translational initiation regions (and in some embodiment, the third translational initiation region) provide approximately equal translational strengths. In some embodiments, the relative translation strength is about one or two. In some embodiments the relative translation strength is about one. In some embodiments, the relative translation strength is about two. In some embodiments, the relative translation strength is one and/or two. In some embodiments, the relative translation strength is about three or about four. In some embodiments, the relative translation strength is selected from one or more of one, two, three, four, five, or more (such as six or seven or more).

In some embodiments, the polynucleotide of the invention further comprises a promoter operably linked to the heterologous polypeptide. In some embodiments, the promoter is a prokaryotic promoter selected from the group consisting of phoA, tac, lpp, lac-lpp, lac, ara, trp, and T7 promoter. In some embodiments, the promoter is a phoA promoter. In some embodiments involving expression of antibody heavy and light chain, the polynucleotide further comprises (a) a first promoter, wherein the first promoter is operably linked to a light chain and (b) a second promoter, wherein the second promoter is operably linked to a heavy chain. In some embodiments, the first and second promoters are both phoA promoters. In some embodiments involving expression of antibody heavy and light chain and Fc polypeptide, the polynucleotide further comprises (c) a third promoter, wherein the third promoter is operably linked to a Fc polypeptide. In some embodiments, the third promoter is a Fc polypeptide.

When expressing polypeptides that comprise more than one polypeptide (e.g., an antibody comprising a heavy chain and light chain), the polynucleotide for expressing the polypeptide may be a polycistronic polynucleotide (ie, a single polynucleotide that contains and expresses multiple cistrons under the regulatory control of a single promoter). A common example of a polycistronic vector is a "dicistronic" vector that contains and expresses two different polypeptides under the control of one promoter. Upon expression of a dicistronic or polycistronic vector, multiple coding regions (eg, genes) are first transcribed as a single transcriptional unit, and then translated separately. A cistron refers to a genetic element broadly equivalent to a translation unit comprising the nucleotide sequence coding for a polypeptide chain and adjacent control regions (including, e.g., a TIR). In other embodiments, the polynucleotide may comprise separate cistrons, which refers to a single polynucleotide comprising at least two separate promoter-citron pairs, wherein each cistron is under the control of its own promoter. Upon expression of a separate cistron expression vector, both transcription and translation processes of different genes are separate and independent. In yet another embodiment, the polynucleotide may comprise a polycistronic portion and a separate cistron portion.

In yet another aspect, the invention provides vectors comprising polynucleotide of the invention. In some embodiments, the vectors are expression vectors.

In a further aspect, the invention provides compositions comprising one or more polynucleotides of the invention and a carrier. In one embodiment, the carrier is pharmaceutically acceptable.

In one aspect, the invention provides host cells comprising polynucleotide or vector of the invention. In some embodiments, the host cells comprise polynucleotide of the invention encoding an antibody (in some embodiments, a bispecific or one-armed antibody). The host cell may comprise one or more polynucleotides collectively encoding the antibody. A vector can be of any type, for example, a recombinant vector such as an expression vector. Any of a variety of host cells can be used. In one embodiment, a host cell is a prokaryotic cell, for example, E. coli. In some embodiments, the E. coli is of a strain deficient in endogenous protease activities. In some embodiments, the genotype of the E. coli lacks degP and prc genes and harbors a mutant spr gene.

In some embodiments, the host cell further comprises a polynucleotide encoding a prokaryotic chaperone protein (such as Dsb proteins (DsbA, DsbB, DsbC, DsbD, FkpA and/or DsbG). In some embodiments, chaperon protein is overexpressed in the host cell. In some embodiments, the chaperone protein is Dsb A and/or DsbC.

In one aspect, the host cell comprises one or more polynucleotides collectively encoding a one-armed antibody. In one embodiment, a single polynucleotide encodes (a) the light and heavy chain components of the one armed antibody, and (b) the Fc polypeptide. In one embodiment, a single polynucleotide encodes the light chain and Fc polypeptide components of the one armed antibody, and a separate polynucleotide encodes the heavy chain polypeptide. In one embodiment, a single polynucleotide encodes the heavy chain and Fc polypeptide components of the one-armed antibody and a separate polynucleotide encodes the light chain component of the one-armed antibody. In one embodiment, separate polynucleotides encode the light chain component of the one-armed antibody, the heavy chain component of the one-armed antibody and the Fc polypeptide, respectively.

Heterologous polypeptides are described herein. In some embodiments, the heterologous polypeptide is an antibody. In some embodiments, the antibody is a monoclonal antibody. In other embodiments, the antibody is a polyclonal antibody. In some embodiments, the antibody is selected from the group consisting of a chimeric antibody, an affinity matured antibody, a humanized antibody, and a human antibody. In certain embodiments, the antibody is a bispecific antibody. In certain embodiments, the antibody is an antibody fragment. In some embodiments, the antibody is a monovalent antibody. In some embodiments, the antibody is a Fab, Fab', Fab'-SH, F(ab')$_2$, or scFv. In some embodiments, the antibody is a one-armed antibody (i.e., the heavy chain variable domain and the light chain variable domain form a single antigen binding arm) comprising an Fc region, wherein the Fc region comprises a first and a second Fc polypeptide, wherein the first and second Fc polypeptides are present in a complex and form a Fc region that increases stability of said antibody fragment compared to a Fab molecule comprising said antigen binding arm.

In some embodiments, the antibody binds (in some embodiments, specifically binds) c-met. In some embodiments, the anti-c-met antibody comprises (a) a first polypeptide comprising a heavy chain variable domain having the sequence: EVQLVESGGGLVQPGGSLRLSCAAS-GYTFTSYWLHWVRQAPGKGLEWVGMIDPS NSDTRFNPNFKDRFTISADTSKNTAYLQMNSLRAED-TAVYYCATYRSYVTPLDYW GQGTLVTVSS (SEQ ID NO:43), CH1 sequence, and a first Fc polypeptide; (b) a second polypeptide comprising a light chain variable domain having the sequence: DIQMTQSPSSLSAS-VGDRVTITCKSSQSLLYTSSQKNYLAWYQQKPGKAP-KLLIYW ASTRESGVPSRFSGSGSGTDFTLTISS-LQPEDFATYYCQQYYAYPWTFGQGTKVEIK R (SEQ ID NO:44), and CL1 sequence; and (c) a third polypeptide comprising a second Fc polypeptide, wherein the heavy chain variable domain and the light chain variable domain are present as a complex and form a single antigen binding arm, wherein the first and second Fc polypeptides are present in a complex and form a Fc region that increases stability of said antibody fragment compared to a Fab molecule comprising said antigen binding arm. In some embodiments, the first polypeptide comprises the Fc sequence depicted in FIG. 7 (SEQ ID NO: 68) and the second polypeptide comprises the Fc sequence depicted in FIG. 8 (SEQ ID NO: 47). In some embodiments, the first polypeptide comprises the Fc sequence depicted in FIG. 8 (SEQ ID NO: 47) and the second polypeptide comprises the Fc sequence depicted in FIG. 7 (SEQ ID NO: 68).

In some embodiments, the anti-c-met antibody comprises (a) a first polypeptide comprising a heavy chain variable domain, said polypeptide comprising the sequence: EVQLVESGGGLVQPGGSLRLSCAASGYTFTSYWLH-WVRQAPGKGLEWVGMIDPS NSDTRFNPNFKDRFTI-SADTSKNTAYLQMNSLRAEDTAVYYCATYRSYVT-PLDYW GQGTLVTVSSASTKGPSVFPLAPSSKSTSGGTAALG-CLVKDYFPEPVTVSWNSGAL TSGVHTFPAVLQSS-GLYSLSSVVTVPSSSLGTQTYICNVNHKPSNTKVDK-KVEPKS CDKTHTCPPCPAPELLGGPSVFLFPPKPKDTLMISRT-PEVTCVVVDVSHEDPEVKFN WYVDGVEVHNAKTK-PREEQYNSTYRVVSVLTVLHQDWLNGKEYKCK-VSNKALP APIEKTISKAKGQPREPQVYTLPPSREEMTKNQVSLS-CAVKGFYPSDIAVEWESNG QPENNYKTTPPVLDS-DGSFFLVSKLTVDKSRWQQGNVFSCSVMHEALHN-HYTQKSLSLSPGK (SEQ ID NO: 45); (b) a second polypeptide comprising a light chain variable domain, the polypeptide comprising the sequence DIQMTQSPSSLSAS-VGDRVTITCKSSQSLLYTSSQKNYLAWYQQKPGKAP-KLLIYW ASTRESGVPSRFSGSGSGTDFTLTISS-LQPEDFATYYCQQYYAYPWTFGQGTKVEIK RTVAAPSVFIFPPSDEQLKSGTASVVCLLNNFY-PREAKVQWKVDNALQSGNSQESV TEQDSKD-STYSLSSTLTLSKADYEKHKVY-ACEVTHQGLSSPVTKSFNRGEC (SEQ ID NO:46); and a third polypeptide comprising a Fc polypeptide, the polypeptide comprising the sequence DKTHTCPPCPAPELLGGPS-VFLFPPKPKDTLMISRTPEVTCVVVDVSHEDPEVKFN WYVDGVEVHNAKTKPREEQYNSTYRVVSVLTVL-HQDWLNGKEYKCKVSNKALP APIEKTISKAK-GQPREPQVYTLPPSREEMTKNQVSLWCLVKGFYPS-DIAVEWESNG QPENNYKTTPPVLDSDGSFFLYSKLTVDKSRWQQGN-VFSCSVMHEALHNHYTQKS LSLSPGK (SEQ ID NO: 47), wherein the heavy chain variable domain and the light chain variable domain are present as a complex and form a single antigen binding arm, wherein the first and second Fc polypeptides are present in a complex and form a Fc region that increases stability of said antibody fragment compared to a Fab molecule comprising said antigen binding arm.

In one embodiment, the anti-c-met antibody comprises a heavy chain variable domain comprising one or more of CDR1-HC, CDR2-HC and CDR3-HC sequence depicted in FIG. 7 (SEQ ID NO:52-53 & 66). In some embodiments, the antibody comprises a light chain variable domain comprising one or more of CDR1-LC, CDR2-LC and CDR3-LC sequence depicted in FIG. 7 (SEQ ID NOs: 49-51). In some embodiments, the heavy chain variable domain comprises FR1-HC, FR2-HC, FR3-HC and FR4-HC sequence depicted in FIG. 7 (SEQ ID NOs: 62-65). In some embodiments, the light chain variable domain comprises FR1-LC, FR2-LC, FR3-LC and FR4-LC sequence depicted in FIG. 7 (SEQ ID NO: 57-60).

In some embodiments, the antibody comprises at least one characteristic that promotes heterodimerization, while minimizing homodimerization, of the Fc sequences within the antibody fragment. Such characteristic(s) improves yield and/or purity and/or homogeneity of the immunoglobulin populations obtainable by methods of the invention as described herein. In one embodiment, a first Fc polypeptide and a second Fc polypeptide meet/interact at an interface. In some embodiments wherein the first and second Fc polypeptides meet at an interface, the interface of the second Fc polypeptide (sequence) comprises a protuberance (also termed a "knob") which is positionable in a cavity (also termed a "hole") in the interface of the first Fc polypeptide (sequence). In one embodiment, the antibody comprises Fc mutations constituting "knobs" and "holes" as described in WO2005/063816. For example, a hole mutation can be one or more of T366A, L368A and/or Y407V in an Fc polypeptide, and a knob mutation can be T366W.

The invention also provides methods using the variant TIR and signal sequences of the invention. It is understood that any of the variant TIR, signal sequences and polynucleotides disclosed herein are suitable for use in methods, e.g., methods of the invention disclosed herein. In a further aspect, the invention provides methods of making a heterologous polypeptide of the invention. For example, the invention provides methods of making an a heterologous polypeptide (e.g., an antibody, which, as defined herein includes full length antibody and fragments thereof), said method comprising culturing a host cell comprising a polynucleotide of the invention (e.g., a polynucleotide comprising a translation initiation region) so that the polynucleotide is expressed, whereby upon expression of said polynucleotide in a host cell (e.g. a prokaryotic host cell), the heterologous polypeptide is folded to form a biologically active heterologous polypeptide. In embodiments involving expression of antibodies, upon expression of said polynucleotide in a host cell, the light and heavy chains are folded and assembled to form a biologically active antibody. In some embodiments, the method further comprises recovering the heterologous polypeptide (e.g., an antibody) from the host cell culture. In some embodiments, the heterologous polypeptide is recovered from the host cell culture medium. In some embodiments, the method further comprises combining the recovered heterologous polypeptide (e.g., an antibody) with a pharmaceutically acceptable carrier, excipient, or carrier to prepare a pharmaceutical formulation comprising the heterologous polypeptide (e.g., antibody).

In one aspect, the invention provides methods of secreting a heterologous polypeptide of interest from a cell, said method comprising culturing a host cell comprising a polynucleotide of the invention so that the polynucleotide is expressed and the heterologous polypeptide is secreted.

In one aspect, the invention provides methods of translocating a heterologous polypeptide of interest from a cell, said method comprising culturing a host cell comprising a polynucleotide of the invention so that the polynucleotide is expressed and the heterologous polypeptide is translocated.

In another aspect, the invention provides method of optimizing secretion of a heterologous polypeptide of interest in a cell comprising comparing the levels of expression of the polypeptide under control of a set of polynucleotide variants of a translation initiation region, wherein the set of variants represents a range of translational strengths, and determining the optimal translational strength for production of mature polypeptide. In some embodiments, the optimal translational strength is less than the translational strength of the wild-type translation initiation region. In some embodiments, the optimal translational strength is more than the translational strength of the wild-type translation initiation region. In some embodiments, the variants comprise polynucleotide variants of a secretion signal sequence. In some embodiments, the variant secretion signal sequences are sec pathway signal sequences and/or SRP pathway signal sequences. In some embodiments, the variant secretion signal sequences are PhoA, MalE, DsbA, or STII variant signal sequences. In some embodiments, the variant is one or more variant shown in Table 2. In some embodiments, the variant comprises sequence of one of SEQ ID Nos 1-14, 36-39, 41-42.

In one aspect, the invention provides a heterologous polypeptide obtained by a method of the invention as described herein. In some embodiments, the heterologous polypeptide is an antibody.

In one aspect, the invention provides uses of a heterologous polypeptide generated using the methods of the invention, in the preparation of a medicament for the therapeutic and/or prophylactic treatment of a disease, such as a cancer, a tumor, a cell proliferative disorder, and/or an immune (such as autoimmune) disorder. The heterologous polypeptide can be of any form described herein, including antibody, antibody fragment, polypeptide (e.g., an oligopeptide), or combination thereof.

In one aspect, the invention provides use of a polynucleotide of the invention in the preparation of a medicament for the therapeutic and/or prophylactic treatment of a disease, such as a cancer, a tumor, a cell proliferative disorder and/or an immune (such as autoimmune) disorder.

In one aspect, the invention provides use of an expression vector of the invention in the preparation of a medicament for the therapeutic and/or prophylactic treatment of a disease, such as a cancer, a tumor, a cell proliferative disorder and/or an immune (such as autoimmune) disorder.

In one aspect, the invention provides use of a host cell of the invention in the preparation of a medicament for the therapeutic and/or prophylactic treatment of a disease, such as a cancer, a tumor, a cell proliferative disorder and/or an immune (such as autoimmune) disorder.

In one aspect, the invention provides use of an article of manufacture of the invention in the preparation of a medicament for the therapeutic and/or prophylactic treatment of a disease, such as a cancer, a tumor, a cell proliferative disorder, an immune (such as autoimmune) disorder and/or an angiogenesis-related disorder (wound healing).

In one aspect, the invention provides use of a kit of the invention in the preparation of a medicament for the therapeutic and/or prophylactic treatment of a disease, such as a cancer, a tumor, a cell proliferative disorder and/or an immune (such as autoimmune) disorder).

BRIEF DESCRIPTION OF THE SEVERAL VIEWS OF THE DRAWINGS

(FIG. 3A) Samples from cells carrying the plasmid pBR-SS-5D5-1.1 (SS1.1), pBR-MS-5D5-1.1 (MS1.1), pBR-DS-5D5-1.1 (DS1.1) or pBR-PS-5D5-1.1 (PS1.1) were separated by SDS-PAGE gel electrophoresis (mass in kDa indicated at the left side), transferred to nitrocellulose, and probed for the presence of heavy chain-containing species with an α-Fc specific antibody. Soluble samples (top blot) consisted of the putatively identified bands corresponding to (from top to bottom): full-length antibody, heavy-heavy-light (HHL), heavy-light (HL) or free heavy chain (heavy chain monomer). Normalized, total protein samples (bottom blot) were reduced with 0.2 M DTT to disrupt disulfide bond structure and each individual lane migrated to a single band with an apparent mass of ~49 kDa. (FIG. 3B) The samples from (A) were run on a separate SDS-PAGE gel (mass in kDa indicated at the right side), transferred to nitrocellulose and probed for complexes containing a light chain with an α-κLc specific antibody. Soluble samples (top blot) consisted of the putatively identified bands corresponding to (from top to bottom): full-length antibody, HL, light-light (LL) dimer or free light chain (light chain monomer). Normalized, total protein samples (bottom blot) were reduced with 0.2 M DTT and each individual lane migrated to a single band with an apparent mass of ~25 kDa. Abbreviations: S=signal sequence STII M=signal sequence MalE D=signal sequence DsbA P=signal sequence PhoA. XX#.# (e.g. DS1.1) refers to heavy chain signal sequence, light chain signal sequence, heavy chain TIR, light chain TIR used in the experiment.

FIG. 7: depicts amino acid sequences of the framework (FR), CDR, first constant domain (CL or CH1) and Fc region (Fc) of MetMAb (OA5D5v2). Figure discloses Light Chain sequences as SEQ ID NOS 57-60, 49-51 & 61, respectively, in order of appearance and Heavy Chain sequences as SEQ ID NOS 62-65, 52-53 & 66-68, respectively, in order of appearance. The Fc sequence depicted comprises "hole" (cavity) mutations T366S, L368A and Y407V, as described in WO 2005/063816.

FIG. 8: depicts sequence of an Fc polypeptide (SEQ ID NO: 47) comprising "knob" (protuberance) mutation T366W, as described in WO 2005/063816. In one embodiment, an Fc polypeptide comprising this sequence forms a complex with an Fc polypeptide comprising the Fc sequence of FIG. 7 to generate an Fc region.

DETAILED DESCRIPTION OF THE INVENTION

General Techniques

Figure 1:
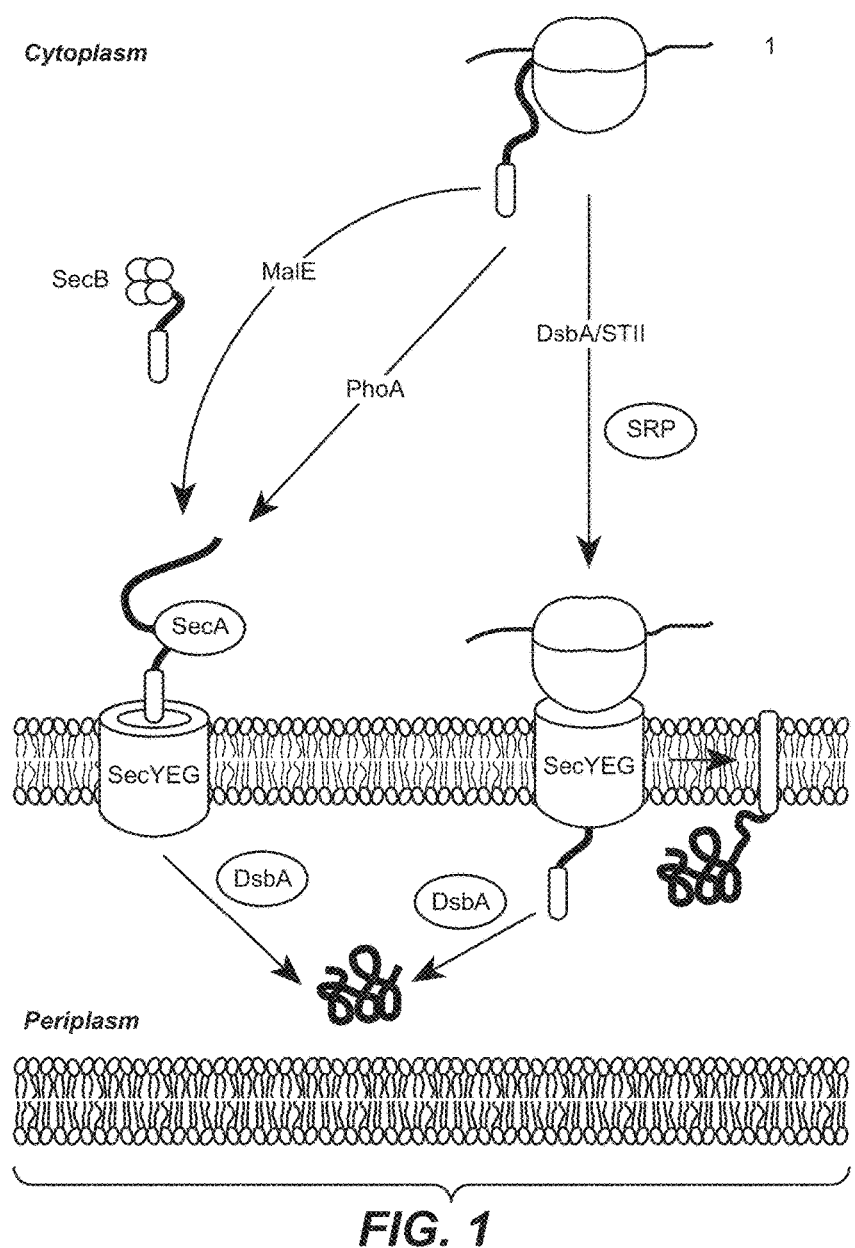
FIG. 1: Translocation of indicated signal peptides across the inner membrane of bacteria. The maltose-binding periplasmic protein (MalE) and alkaline phosphatase (PhoA) signal peptides direct translocation from the cytoplasm to the periplasm in a post-translational manner with the aid of the molecular motor SecA. The heat-stable enterotoxin II (StII) and thiol:disulfide interchange protein (DsbA) signal peptides direct translocation in a co-translational manner with aid from the signal recognition particle (SRP).

The techniques and procedures described or referenced herein are generally well understood and commonly employed using conventional methodology by those skilled in the art, such as, for example, the widely utilized methodologies described in Sambrook et al., Molecular Cloning: A Laboratory Manual 3rd. edition (2001) Cold Spring Harbor Laboratory Press, Cold Spring Harbor, N.Y. CURRENT PROTOCOLS IN MOLECULAR BIOLOGY (F. M. Ausubel, et al. eds., (2003)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)).

Definitions

The term "vector," as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a phage vector. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "recombinant vectors"). In general, expression vectors of utility in recombinant DNA techniques are often in the form of plasmids. In the present specification, "plasmid" and "vector" may be used interchangeably as the plasmid is the most commonly used form of vector.

The term "cistron," as used herein, is intended to refer to a genetic element broadly equivalent to a translational unit comprising the nucleotide sequence coding for a polypeptide chain and adjacent control regions. "Adjacent control regions" include, for example, a translational initiation region (TIR; as defined herein below) and a termination region.

A "polycistronic" expression vector refers to a single vector that contains and expresses multiple cistrons under the regulatory control of one single promoter. A common example of polycistronic vector is a "dicistronic" vector that contains and expresses two different polypeptides under the control of one promoter. Upon expression of a dicistronic or polycistronic vector, multiple genes are first transcribed as a single transcriptional unit, and then translated separately.

A "separate cistron" expression vector according to the present invention refers to a single vector comprising at least two separate promoter-cistron pairs, wherein each cistron is under the control of its own promoter. Upon expression of a separate cistron expression vector, both transcription and translation processes of different genes are separate and independent.

The "translation initiation region" or TIR or translational initiation region or translational initiation sequence, as used herein refers to a nucleic acid region providing the efficiency of translational initiation of a gene of interest. In general, a TIR within a particular cistron encompasses the ribosome binding site (RBS) and sequences 5' and 3' to RBS. The RBS is defined to contain, minimally, the Shine-Dalgarno region and the start codon (AUG). Accordingly, a TIR also includes at least a portion of the nucleic acid sequence to be translated. Preferably, a TIR of the invention includes a secretion signal sequence encoding a signal peptide that precedes the sequence encoding for the light or heavy chain within a cistron. A TIR variant contains sequence variants (particularly substitutions) within the TIR region that alter the property of the TIR, such as its translational strength as defined herein below. Preferably, a TIR variant of the invention contains sequence substitutions within the first 2 to about 14, preferably about 4 to 12, more preferably about 6 codons of the secretion signal sequence that precedes the sequence encoding for the light or heavy chain within a cistron.

The term "translational strength" as used herein refers to a measurement of a secreted polypeptide in a control system wherein one or more variants of a TIR is used to direct secretion of a polypeptide and the results compared to the wild-type TIR or some other control under the same culture and assay conditions. Without being limited to any one theory, "translational strength" as used herein can include, for example, a measure of mRNA stability, efficiency of ribosome binding to the ribosome binding site, and mode of translocation across a membrane.

"Secretion signal sequence" or "signal sequence" refers to a nucleic acid sequence encoding for a short signal peptide that can be used to direct a newly synthesized protein of interest through a cellular membrane, usually the inner membrane or both inner and outer membranes of prokaryotes. As such, the protein of interest such as the immunoglobulin light or heavy chain polypeptide is secreted into the periplasm of the prokaryotic host cells or into the culture medium. The signal peptide encoded by the secretion signal sequence may be endogenous to the host cells, or they may be exogenous, including signal peptides native to the polypeptide to be expressed. Secretion signal sequences are typically present at the amino terminus of a polypeptide to be expressed, and are typically removed enzymatically between biosynthesis and secretion of the polypeptide from the cytoplasm. Thus, the signal peptide is usually not present in a mature protein product.

"Operably linked" refers to a juxtaposition of two or more components, wherein the components so described are in a relationship permitting them to function in their intended manner. For example, a promoter is operably linked to a coding sequence if it acts in cis to control or modulate the transcription of the linked sequence. Generally, but not necessarily, the DNA sequences that are "operably linked" are contiguous and, where necessary to join two protein coding regions or in the case of a secretory leader, contiguous and in reading frame. However, although an operably linked promoter is generally located upstream of the coding sequence, it is not necessarily contiguous with it. Operably linked enhancers can be located upstream, within or downstream of coding sequences and at considerable distances from the promoter. Linking is accomplished by recombinant methods known in the art, e.g., using PCR methodology, by annealing, or by ligation at convenient restriction sites. If convenient restriction sites do not exist, then synthetic oligonucleotide adaptors or linkers are used in accord with conventional practice.

"Regulatory elements" as used herein, refer to nucleotide sequences present in cis, necessary for transcription and translation of a polynucleotide encoding a heterologous polypeptide into polypeptides. The transcriptional regulatory elements normally comprise a promoter 5' of the gene sequence to be expressed, transcriptional initiation and termination sites, and polyadenylation signal sequence. The term "transcriptional initiation site" refers to the nucleic acid in the construct corresponding to the first nucleic acid incorporated into the primary transcript, i.e., the mRNA precursor; the transcriptional initiation site may overlap with the promoter sequences.

A "promoter" refers to a polynucleotide sequence that controls transcription of a gene or sequence to which it is operably linked. A promoter includes signals for RNA polymerase binding and transcription initiation. The promoters used will be functional in the cell type of the host cell in which expression of the selected sequence is contemplated. A large number of promoters including constitutive, inducible and repressible promoters from a variety of different sources, are well known in the art (and identified in databases such as GenBank) and are available as or within cloned polynucleotides (from, e.g., depositories such as ATCC as well as other commercial or individual sources). With inducible promoters, the activity of the promoter increases or decreases in response to a signal.

The term "host cell" (or "recombinant host cell"), as used herein, is intended to refer to a cell that has been genetically altered, or is capable of being genetically altered by introduction of an exogenous polynucleotide, such as a recombinant plasmid or vector. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

An "isolated" polypeptide (e.g., an antibody) is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the polypeptide will be purified (1) to greater than 95% by weight of polypeptide as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE (sodium dodecyl sulfate polyacrylamide gel electrophoresis) under reducing or nonreducing conditions using Coomassie blue or, preferably, silver stain. Isolated polypeptide includes the polypeptide in situ within recombinant cells since at least one component of the polypeptide's natural environment will not be present. Ordinarily, however, isolated polypeptide will be prepared by at least one purification step.

An "isolated" nucleic acid molecule is a nucleic acid molecule that is identified and separated from at least one contaminant nucleic acid molecule with which it is ordinarily associated in the natural source of the nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the nucleic acid (for example, an antibody encoding nucleic acid) where, for example, the nucleic acid molecule is in a chromosomal location different from that of natural cells.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase, or by a synthetic reaction. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after synthesis, such as by conjugation with a label. Other types of modifications include, for example, "caps," substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semisolid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, alpha-anomeric sugars, epimeric sugars such as arabinose, xyloses or lyxoses, pyranose sugars, furanose sugars, sedoheptuloses, acyclic analogs and a basic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), (O)NR$_2$ ("amidate"), P(O)R, P(O)OR', CO or CH₂ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

"Oligonucleotide," as used herein, generally refers to short, generally single stranded, generally synthetic polynucleotides that are generally, but not necessarily, less than about 200 nucleotides in length. The terms "oligonucleotide" and "polynucleotide" are not mutually exclusive. The description above for polynucleotides is equally and fully applicable to oligonucleotides.

As used herein, "polypeptide" refers generally to peptides and proteins from any cell source having more than about ten amino acids. "Heterologous" polypeptides are those polypeptides foreign to the host cell being utilized, such as a human protein produced by E. coli. While the heterologous polypeptide may be prokaryotic or eukaryotic, preferably it is eukaryotic, more preferably mammalian, and most preferably human. Preferably, it is a recombinantly produced, or recombinant polypeptide. "Heterologous" polypeptides are those polypeptides foreign to the host cell being utilized, such as a human protein produced by E. coli. While the heterologous polypeptide may be prokaryotic or eukaryotic, preferably it is eukaryotic, more preferably mammalian, and most preferably human. Preferably, it is a recombinantly produced, or recombinant polypeptide.

Examples of mammalian polypeptides include molecules such as, e.g., renin, a growth hormone, including human growth hormone; bovine growth hormone; growth hormone releasing factor; parathyroid hormone; thyroid stimulating hormone; lipoproteins; 1-antitrypsin; insulin A-chain; insulin B-chain; proinsulin; thrombopoietin; follicle stimulating hormone; calcitonin; luteinizing hormone; glucagon; clotting factors such as factor VIIIC, factor IX, tissue factor, and von Willebrands factor; anti-clotting factors such as Protein C; atrial naturietic factor; lung surfactant; a plasminogen activator, such as urokinase or human urine or tissue-type plasminogen activator (t-PA) and variants thereof such as RETEVASE™ and TNKASE™; bombesin; thrombin; hemopoietic growth factor; tumor necrosis factor-alpha and -beta; antibodies to ErbB2 domain(s) such as 2C4 (WO 01/00245; hybridoma ATCC HB-12697), which binds to a region in the extracellular domain of ErbB2 (e.g., any one or more residues in the region from about residue 22 to about residue 584 of ErbB2, inclusive), enkephalinase; a serum albumin such as human serum albumin; Muellerian-inhibiting substance; relaxin A-chain; relaxin B-chain; prorelaxin; mouse gonadotropin-associated peptide; a microbial protein, such as beta-lactamase; DNase; inhibin; activin; vascular endothelial growth factor (VEGF); receptors for hormones or growth factors; integrin; protein A or D; rheumatoid factors; a neurotrophic factor such as brain-derived neurotrophic factor (BDNF), neurotrophin-3, -4, -5, or -6 (NT-3, NT-4, NT-5, or NT-6), or a nerve growth factor such as NGF; cardiotrophins (cardiac hypertrophy factor) such as cardiotrophin-1 (CT-1); platelet-derived growth factor (PDGF); fibroblast growth factor such as aFGF and bFGF; epidermal growth factor (EGF); transforming growth factor (TGF) such as TGF-alpha and TGF-beta, including TGF-1, TGF-2, TGF-3, TGF-4, or TGF-5; insulin-like growth factor-I and -II (IGF-I and IGF-II); des(I-3)-IGF-I (brain IGF-I), insulin-like growth factor binding proteins; CD proteins such as CD-3, CD-4, CD-8, and CD-19; erythropoietin; osteoinductive factors; immunotoxins; a bone morphogenetic protein (BMP); an interferon such as interferon-alpha, -beta, and -gamma; serum albumin, such as human serum albumin (HSA) or bovine serum albumin (BSA); colony stimulating factors (CSFs), e.g., M-CSF, GM-CSF, and G-CSF; interleukins (ILs), e.g., IL-1 to IL-10; anti-HER-2 antibody; Apo2 ligand; superoxide dismutase; T-cell receptors; surface membrane proteins; decay accelerating factor; viral antigen such as, for example, a portion of the AIDS envelope; transport proteins; homing receptors; addressins; regulatory proteins; antibodies; and fragments of any of the above-listed polypeptides.

Preferred polypeptides herein include human serum albumin (HSA), 2C4, tissue factor, anti-tissue factor, anti-CD20, anti-HER-2, heregulin, anti-IgE, anti-CD11a, anti-CD18, VEGF and receptors and antibodies thereto such as rhuFab V2 and AVASTINT™, growth hormone and its variants, such as hGH, growth hormone receptors, growth hormone releasing protein (GHRP), LIV-1 (EP 1,263,780), TRAIL, tumor necrosis factor (TNF) and antibodies thereto, TNF receptor and related antibodies, TNF-receptor-IgG, TNF receptor associated factors (TRAFs) and inhibitors thereof, Factor VIII, Factor VIII B domain, interferons such as interferon-gamma, transforming growth factors (TGFs) such as TGF-beta, anti-TGF such as anti-TGF-beta, activin, inhibin, anti-activin, anti-inhibin, tissue-plasminogen activators and their variants such as t-PA, RETEPLASE™, and TNKase, anti-Fas antibodies, Apo-2 ligand; Apo-2 ligand inhibitor; Apo-2 receptor, Apo-3, apoptotic factors, Ced-4, DcR3, death receptor and agonist antibodies (DR4, DR5), lymphotoxin (LT), prolactin, prolactin receptor, SOB proteins, WISP (wnt-induced secreted proteins), neurotoxin-3 (NT-3), nerve growth factor (NGF) and anti-NGF, DNase, hepatitis antigen, herpes simplex antigen, leptin, insulin-like growth factors (IGFs) such as IGF-1 and IGF-2 and their binding proteins and receptors such as IGFBP-1-IGFBP-6, insulin, fibroblast growth factors (FGFs) such as FGF-17, Toll protein, TIE ligands, CD40 and anti-CD40, immuno-adhesins, subtilisin, hepatocyte growth factor (HGF), thrombopoietin (TPO), interleukins such as IL-2, IL-12, IL-17, IL-22, IL-8, IL-9, and antibodies thereto, and prostrate-specific cancer antigen (PSCA).

Particularly preferred polypeptides are recombinant polypeptides, more preferably antibodies, which include monoclonal antibodies and humanized antibodies. Such antibodies may be full-length antibodies or antibody fragments. More preferably, these antibodies are human or humanized antibodies. Still more preferably, the antibody is an anti-c-met, anti-IgE, anti-CD18, anti-VEGF, anti-tissue factor, 2C4, anti-Her-2, anti-CD20, anti-CD40, or anti-CD11a antibody. Antibody fragments encompassed within the definition of polypeptide preferably comprise a light chain, more preferably a kappa light chain. Such preferred fragments include, for example, a Fab, Fab', F(ab')₂, or F(ab')₂-leucine zipper (LZ) fusion, and a one-armed antibody.

Protein "expression" refers to conversion of the information encoded in a gene into messenger RNA (mRNA) and then to the protein.

An "immunoconjugate" (interchangeably referred to as "antibody-drug conjugate," or "ADC") means an antibody conjugated to one or more cytotoxic agents, such as a chemotherapeutic agent, a drug, a growth inhibitory agent, a toxin (e.g., a protein toxin, an enzymatically active toxin of bacterial, fungal, plant, or animal origin, or fragments thereof), or a radioactive isotope (i.e., a radioconjugate).

A "blocking" antibody or an antibody "antagonist" is one which inhibits or reduces biological activity of the antigen it binds. In some embodiments, blocking antibodies or antagonist antibodies completely inhibit the biological activity of the antigen.

An "agonist antibody", as used herein, is an antibody which mimics at least one of the functional activities of a polypeptide of interest (e.g., HGF).

"Binding affinity" generally refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Desirably the Kd is $1 \times 10^{-7}$, $1 \times 10^{-8}$, $5 \times 10^{-8}$, $1 \times 10^{-9}$, $3 \times 10^{-9}$, $5 \times 10^{-9}$, or even $1 \times 10^{-10}$ or stronger. Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention. Specific illustrative embodiments are described in the following.

In one embodiment, the "Kd" or "Kd value" according to this invention is measured by a radiolabeled antigen binding assay (RIA) performed with the Fab version of an antibody of interest and its antigen as described by the following assay that measures solution binding affinity of Fabs for antigen by equilibrating Fab with a minimal concentration of ($^{125}$I)-labeled antigen in the presence of a titration series of unlabeled antigen, then capturing bound antigen with an anti-Fab antibody-coated plate (Chen, et al., (1999) J. Mol. Biol. 293:865-881). To establish conditions for the assay, microtiter plates (Dynex) are coated overnight with 5 μg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbant plate (Nunc #269620), 100 pM or 26 pM [$^{125}$I]-antigen are mixed with serial dilutions of a Fab of interest (e.g., consistent with assessment of an anti-VEGF antibody, Fab-12, in Presta et al., (1997) Cancer Res. 57:4593-4599). The Fab of interest is then incubated overnight; however, the incubation may continue for a longer period (e.g., 65 hours) to insure that equilibrium is reached. Thereafter, the mixtures are transferred to the capture plate for incubation at room temperature (e.g., for one hour). The solution is then removed and the plate washed eight times with 0.1% Tween-20 in PBS. When the plates have dried, 150 μl/well of scintillant (MicroScint-20; Packard) is added, and the plates are counted on a Topcount gamma counter (Packard) for ten minutes. Concentrations of each Fab that give less than or equal to 20% of maximal binding are chosen for use in competitive binding assays. According to another embodiment the Kd or Kd value is measured by using surface plasmon resonance assays using a BIAcore™-2000 or a BIAcore™-3000 (BIAcore, Inc., Piscataway, N.J.) at 25° C. with immobilized antigen CM5 chips at ~10 response units (RU). Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, into 5 m/ml (~0.2 μM) before injection at a flow rate of 5 μl/minute to achieve approximately 10 response units (RU) of coupled protein. Following the injection of antigen, 1M ethanolamine is injected to block unreacted groups. For kinetics measurements, two-fold serial dilutions of Fab (0.78 nM to 500 nM) are injected in PBS with 0.05% Tween 20 (PBST) at 25° C. at a flow rate of approximately 25 μl/min. In some embodiments, the following modifications are used for the surface Plasmon resonance assay method: antibody is immobilized to CM5 biosensor chips to achieve approximately 400 RU, and for kinetic measurements, two-fold serial dilutions of target protein are injected in PBST buffer at 25° C. with a flow rate of about 30 ul/minute. Association rates ($k_{on}$) and dissociation rates ($k_{off}$) are calculated using a simple one-to-one Langmuir binding model (BIAcore Evaluation Software version 3.2) by simultaneous fitting the association and dissociation sensorgram. The equilibrium dissociation constant (Kd) is calculated as the ratio $k_{off}/k_{on}$. See, e.g., Chen, Y., et al., (1999) J. Mol. Biol. 293:865-881. If the on-rate exceeds $10^6$ $M^{-1}$ $S^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-Aminco spectrophotometer (ThermoSpectronic) with a stir red cuvette.

An "on-rate" or "rate of association" or "association rate" or "$k_{on}$" according to this invention can also be determined with the same surface plasmon resonance technique described above using a BIAcore™-2000 or a BIAcore™-3000 (BIAcore, Inc., Piscataway, N.J.) at 25° C. with immobilized antigen CM5 chips at ~10 response units (RU). Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, into 5 μg/ml (~0.2 uM) before injection at a flow rate of 5 μl/minute to achieve approximately 10 response units (RU) of coupled protein. Following the injection of antigen, 1M ethanolamine is injected to block unreacted groups. For kinetics measurements, two-fold serial dilutions of Fab (0.78 nM to 500 nM) are injected in PBS with 0.05% Tween 20 (PBST) at 25° C. at a flow rate of approximately 25 μl/min. In some embodiments, the following modifications are used for the surface Plasmon resonance assay method: antibody is immobilized to CM5 biosensor chips to achieve approximately 400 RU, and for kinetic measurements, two-fold serial dilutions of target protein are injected in PBST buffer at 25° C. with a flow rate of about 30 ul/minute. Association rates ($k_{on}$) and dissociation rates ($k_{off}$) are calculated using a simple one-to-one Langmuir binding model (BIAcore Evaluation Software version 3.2) by simultaneous fitting the association and dissociation sensorgram. The equilibrium dissociation constant (Kd) was calculated as the ratio $k_{off}/k_{on}$. See, e.g., Chen, Y., et al., (1999) J. Mol. Biol. 293:865-881. However, if the on-rate exceeds $10^6$ $M^{-1}$ $S^{-1}$ by the surface plasmon resonance assay above, then the on-rate is preferably determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-Aminco spectrophotometer (ThermoSpectronic) with a stir red cuvette.

A "naked antibody" is an antibody that is not conjugated to a heterologous molecule, such as a cytotoxic moiety or radiolabel.

An antibody having a "biological characteristic" of a designated antibody is one which possesses one or more of the biological characteristics of that antibody which distinguish it from other antibodies that bind to the same antigen.

In order to screen for antibodies which bind to an epitope on an antigen bound by an antibody of interest, a routine cross-blocking assay such as that described in Antibodies, A Laboratory Manual, Cold Spring Harbor Laboratory, Ed Harlow and David Lane (1988), can be performed.

To increase the half-life of the antibodies or polypeptide containing the amino acid sequences of this invention, one can attach a salvage receptor binding epitope to the antibody (especially an antibody fragment), as described, e.g., in U.S. Pat. No. 5,739,277. For example, a nucleic acid molecule encoding the salvage receptor binding epitope can be linked in frame to a nucleic acid encoding a polypeptide sequence of this invention so that the fusion protein expressed by the engineered nucleic acid molecule comprises the salvage receptor binding epitope and a polypeptide sequence of this invention. As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule (e.g., Ghetie et al., *Ann. Rev. Immunol.* 18:739-766 (2000), Table 1). Antibodies with substitutions in an Fc region thereof and increased serum half-lives are also described in WO00/42072, WO 02/060919; Shields et al., *J. Biol. Chem.* 276:6591-6604 (2001); Hinton, *J. Biol. Chem.* 279:6213-6216 (2004)). In another embodiment, the serum half-life can also be increased, for example, by attaching other polypeptide sequences. For example, antibodies or other polypeptides useful in the methods of the invention can be attached to serum albumin or a portion of serum albumin that binds to the FcRn receptor or a serum albumin binding peptide so that serum albumin binds to the antibody or polypeptide, e.g., such polypeptide sequences are disclosed in WO01/45746. In one preferred embodiment, the serum albumin peptide to be attached comprises an amino acid sequence of DICLPRWGCLW (SEQ ID NO: 48). In another embodiment, the half-life of a Fab is increased by these methods. See also, Dennis et al. *J. Biol. Chem.* 277:35035-35043 (2002) for serum albumin binding peptide sequences.

By "fragment" is meant a portion of a polypeptide or nucleic acid molecule that contains, preferably, at least 10%, 20%, 30%, 40%, 50%, 60%, 70%, 80%, 90%, 95%, or more of the entire length of the reference nucleic acid molecule or polypeptide. A fragment may contain 10, 20, 30, 40, 50, 60, 70, 80, 90, or 100, 200, 300, 400, 500, 600, or more nucleotides or 10, 20, 30, 40, 50, 60, 70, 80, 90, 100, 120, 140, 160, 180, 190, 200 amino acids or more.

The terms "antibody" and "immunoglobulin" are used interchangeably in the broadest sense and include monoclonal antibodies (e.g., full length or intact monoclonal antibodies), polyclonal antibodies, multivalent antibodies, multispecific antibodies (e.g., bispecific antibodies so long as they exhibit the desired biological activity) and may also include certain antibody fragments (as described in greater detail herein). An antibody can be human, humanized, and/or affinity matured.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity-determining regions (CDRs) or hypervariable regions both in the light-chain and the heavy-chain variable domains. The more highly conserved portions of variable domains are called the framework (FR). The variable domains of native heavy and light chains each comprise four FR regions, largely adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the antigen-binding site of antibodies (see Kabat et al., *Sequences of Proteins of Immunological Interest*, Fifth Edition, National Institute of Health, Bethesda, Md. (1991)). The constant domains are not involved directly in binding an antibody to an antigen, but exhibit various effector functions, such as participation of the antibody in antibody-dependent cellular toxicity.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an $F(ab')_2$ fragment that has two antigen-combining sites and is still capable of cross-linking antigen.

"Fv" is the minimum antibody fragment which contains a complete antigen-recognition and -binding site. In a two-chain Fv species, this region consists of a dimer of one heavy- and one light-chain variable domain in tight, non-covalent association. In a single-chain Fv species, one heavy- and one light-chain variable domain can be covalently linked by a flexible peptide linker such that the light and heavy chains can associate in a "dimeric" structure analogous to that in a two-chain Fv species. It is in this configuration that the three CDRs of each variable domain interact to define an antigen-binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. $F(ab')_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa (κ) and lambda (λ), based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG, and IgM, and several of these can be further divided into subclasses (isotypes), e.g., $IgG_1$, $IgG_2$, $IgG_3$, $IgG_4$, $IgA_1$, and $IgA_2$. The heavy-chain constant domains that correspond to the different classes of immunoglobulins are called α, δ, ε, γ, and μ, respectively. The subunit structures and three-dimensional configurations of different classes of immunoglobulins are well known. "Antibody fragments" comprise only a portion of an intact antibody, wherein the portion preferably retains at least one, preferably most or all, of the functions normally associated with that portion when present in an intact antibody. Examples of antibody fragments include Fab, Fab', F(ab')2, and Fv fragments; diabodies; linear antibodies; single-chain antibody molecules; and multispecific antibodies formed from antibody fragments. In one embodiment, an antibody fragment comprises an antigen binding site of the intact antibody and thus retains the ability to bind antigen. In another embodiment, an antibody fragment, for example one that comprises the Fc region, retains at least one of the biological functions normally associated with the Fc region when present in an intact antibody, such as FcRn binding, antibody half life modulation, ADCC function and complement binding. In one embodiment, an antibody fragment is a monovalent antibody that has an in vivo half life substantially similar to an intact antibody. For e.g., such an antibody fragment may comprise on antigen binding arm linked to an Fc sequence capable of conferring in vivo stability to the fragment.

The term "hypervariable region," "HVR," or "HV," when used herein refers to the regions of an antibody variable domain which are hypervariable in sequence and/or form structurally defined loops. Generally, antibodies comprise six hypervariable regions; three in the VH (H1, H2, H3), and three in the VL (L1, L2, L3). A number of hypervariable region delineations are in use and are encompassed herein. The Kabat Complementarity Determining Regions (CDRs) are based on sequence variability and are the most commonly used (Kabat et al., Sequences of Proteins of Immunological Interest, 5th Ed. Public Health Service, National Institutes of Health, Bethesda, Md. (1991)). Chothia refers instead to the location of the structural loops (Chothia and Lesk, J. Mol. Biol. 196:901-917 (1987)). The AbM hypervariable regions represent a compromise between the Kabat CDRs and Chothia structural loops, and are used by Oxford Molecular's AbM antibody modeling software. The "contact" hypervariable regions are based on an analysis of the available complex crystal structures. The residues from each of these hypervariable regions are noted below.

| | Loop Kabat | AbM | Chothia | Contact |
|---|---|---|---|---|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B | H26-H35B | H26-H32 | H30-H35B |
| | | (Kabat Numbering) | | |
| H1 | H31-H35 | H26-H35 | H26-H32 | H30-H35 |
| | | (Chothia Numbering) | | |
| H2 | H50-H65 | H50-H58 | H53-H55 | H47-H58 |
| H3 | H95-H102 | H95-H102 | H96-H101 | H93-H101 |

Hypervariable regions may comprise "extended hypervariable regions" as follows: 24-36 or 24-34 (L1), 46-56 or 50-56 (L2) and 89-97 (L3) in the VL and 26-35 (H1), 50-65 or 49-65 (H2) and 93-102, 94-102 or 95-102 (H3) in the VH. The variable domain residues are numbered according to Kabat et al., supra for each of these definitions.

"Framework" or "FR" residues are those variable domain residues other than the hypervariable region residues as herein defined.

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally will also comprise at least a portion of an immunoglobulin constant region (Fc), typically that of a human immunoglobulin. For further details, see Jones et al., Nature 321:522-525 (1986); Riechmann et al., Nature 332:323-329 (1988); and Presta, Curr. Op. Struct. Biol. 2:593-596 (1992). See also the following review articles and references cited therein: Vaswani and Hamilton, Ann. Allergy, Asthma & Immunol. 1:105-115 (1998); Harris, Biochem. Soc. Transactions 23:1035-1038 (1995); Hurle and Gross, Curr. Op. Biotech. 5:428-433 (1994).

"Chimeric" antibodies (immunoglobulins) have a portion of the heavy and/or light chain identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., Proc. Natl. Acad. Sci. USA 81:6851-6855 (1984)). Humanized antibody as used herein is a subset of chimeric antibodies.

"Single-chain Fv" or "scFv" antibody fragments comprise the VH and VL domains of antibody, wherein these domains are present in a single polypeptide chain. Generally, the scFv polypeptide further comprises a polypeptide linker between the VH and VL domains which enables the scFv to form the desired structure for antigen binding. For a review of scFv see Pluckthun, in *The Pharmacology of Monoclonal Antibodies*, vol. 113, Rosenburg and Moore eds., Springer-Verlag, New York, pp. 269-315 (1994).

An "antigen" is a predetermined antigen to which an antibody can selectively bind. The target antigen may be polypeptide, carbohydrate, nucleic acid, lipid, hapten or other naturally occurring or synthetic compound. Preferably, the target antigen is a polypeptide.

The term "diabodies" refers to small antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA*, 90:6444-6448 (1993).

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues.

An "affinity matured" antibody is one with one or more alterations in one or more CDRs thereof which result in an improvement in the affinity of the antibody for antigen, compared to a parent antibody which does not possess those alteration(s). Preferred affinity matured antibodies will have nanomolar or even picomolar affinities for the target antigen. Affinity matured antibodies are produced by procedures known in the art. Marks et al. Bio/Technology 10:779-783 (1992) describes affinity maturation by VH and VL domain shuffling. Random mutagenesis of CDR and/or framework residues is described by: Barbas et al., Proc Nat. Acad. Sci, USA 91:3809-3813 (1994); Schier et al., Gene 169:147-155 (1995); Yelton et al., J. Immunol. 155:1994-2004 (1995); Jackson et al., J. Immunol. 154(7):3310-9 (1995); and Hawkins et al., J. Mol. Biol. 226:889-896 (1992).

"Fc receptor" or "FcR" describes a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see review M. in Daëron, *Annu. Rev. Immunol.* 15:203-234 (1997)). FcRs are reviewed in Ravetch and Kinet, *Annu. Rev. Immunol* 9:457-92 (1991); Capel et al., *Immunomethods* 4:25-34 (1994); and de Haas et al., *J. Lab. Clin. Med.* 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., *J. Immunol.* 117:587 (1976) and Kim et al., *J. Immunol.* 24:249 (1994)) and regulates homeostasis of immunoglobulins. WO 00/42072 (Presta) describes antibody variants with improved or diminished binding to FcRs. The content of that patent publication is specifically incorporated herein by reference. See, also, Shields et al., *J. Biol. Chem.* 9(2): 6591-6604 (2001).

Methods of measuring binding to FcRn are known (see, e.g., Ghetie 1997, Hinton 2004). Binding to human FcRn in vivo and serum half life of human FcRn high affinity binding polypeptides can be assayed, e.g., in transgenic mice or transfected human cell lines expressing human FcRn, or in primates administered with the Fc variant polypeptides.

Polypeptide variants with altered Fc region amino acid sequences and increased or decreased C1q binding capability are described in U.S. Pat. No. 6,194,551B1 and WO 99/51642. The contents of those patent publications are specifically incorporated herein by reference. See, also, Idusogie et al., *J. Immunol.* 164:4178-4184 (2000).

The term "Fc region", as used herein, generally refers to a dimer complex comprising the C-terminal polypeptide sequences of an immunoglobulin heavy chain, wherein a C-terminal polypeptide sequence is that which is obtainable by papain digestion of an intact antibody. The Fc region may comprise native or variant Fc sequences. Although the boundaries of the Fc sequence of an immunoglobulin heavy chain might vary, the human IgG heavy chain Fc sequence is usually defined to stretch from an amino acid residue at about position Cys226, or from about position Pro230, to the carboxyl terminus of the Fc sequence. The Fc sequence of an immunoglobulin generally comprises two constant domains, a CH2 domain and a CH3 domain, and optionally comprises a CH4 domain. By "Fc polypeptide" herein is meant one of the polypeptides that make up an Fc region. An Fc polypeptide may be obtained from any suitable immunoglobulin, such as IgG1, IgG2, IgG3, or IgG4 subtypes, IgA, IgE, IgD or IgM. In some embodiments, an Fc polypeptide comprises part or all of a wild type hinge sequence (generally at its N terminus). In some embodiments, an Fc polypeptide does not comprise a functional or wild type hinge sequence.

As used herein, "antibody mutant" or "antibody variant" refers to an amino acid sequence variant of an antibody wherein one or more of the amino acid residues of the species-dependent antibody have been modified. Such mutants necessarily have less than 100% sequence identity or similarity with the species-dependent antibody. In one embodiment, the antibody mutant will have an amino acid sequence having at least 75% amino acid sequence identity or similarity with the amino acid sequence of either the heavy or light chain variable domain of the species-dependent antibody, more preferably at least 80%, more preferably at least 85%, more preferably at least 90%, and most preferably at least 95%. Identity or similarity with respect to this sequence is defined herein as the percentage of amino acid residues in the candidate sequence that are identical (i.e. same residue) or similar (i.e. amino acid residue from the same group based on common side-chain properties, see below) with the species-dependent antibody residues, after aligning the sequences and introducing gaps, if necessary, to achieve the maximum percent sequence identity. None of N-terminal, C-terminal, or internal extensions, deletions, or insertions into the antibody sequence outside of the variable domain shall be construed as affecting sequence identity or similarity.

A "disorder" or "disease" is any condition that would benefit from treatment with a substance/molecule or method of the invention. This includes chronic and acute disorders or diseases including those pathological conditions which predispose the mammal to the disorder in question. Non-limiting examples of disorders to be treated herein include malignant and benign tumors; carcinoma, blastoma, and sarcoma.

"Treatment" refers to both therapeutic treatment and prophylactic or preventative measures. Those in need of treatment include those already having a benign, pre-cancerous, or non-metastatic tumor as well as those in which the occurrence or recurrence of cancer is to be prevented.

The term "therapeutically effective amount" refers to an amount of a therapeutic agent to treat or prevent a disease or disorder in a mammal. In the case of cancers, the therapeutically effective amount of the therapeutic agent may reduce the number of cancer cells; reduce the primary tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the disorder. To the extent the drug may prevent growth and/or kill existing cancer cells, it may be cytostatic and/or cytotoxic. For cancer therapy, efficacy in vivo can, for example, be measured by assessing the duration of survival, time to disease progression (TTP), the response rates (RR), duration of response, and/or quality of life.

An "autoimmune disease" herein is a non-malignant disease or disorder arising from and directed against an individual's own tissues. The autoimmune diseases herein specifically exclude malignant or cancerous diseases or conditions, especially excluding B cell lymphoma, acute lymphoblastic leukemia (ALL), chronic lymphocytic leukemia (CLL), Hairy cell leukemia and chronic myeloblastic leukemia. Examples of autoimmune diseases or disorders include, but are not limited to, inflammatory responses such as inflammatory skin diseases including psoriasis and dermatitis (e.g. atopic dermatitis); systemic scleroderma and sclerosis; responses associated with inflammatory bowel disease (such as Crohn's disease and ulcerative colitis); respiratory distress syndrome (including adult respiratory distress syndrome; ARDS); dermatitis; meningitis; encephalitis; uveitis; colitis; glomerulonephritis; allergic conditions such as eczema and asthma and other conditions involving infiltration of T cells and chronic inflammatory responses; atherosclerosis; leukocyte adhesion deficiency; rheumatoid arthritis; systemic lupus erythematosus (SLE); diabetes mellitus (e.g. Type I diabetes mellitus or insulin dependent diabetes mellitis); multiple sclerosis; Reynaud's syndrome; autoimmune thyroiditis; allergic encephalomyelitis; Sjorgen's syndrome; juvenile onset diabetes; and immune responses associated with acute and delayed hypersensitivity mediated by cytokines and T-lymphocytes typically found in tuberculosis, sarcoidosis, polymyositis, granulomatosis and vasculitis; pernicious anemia (Addison's disease); diseases involving leukocyte diapedesis; central nervous system (CNS) inflammatory disorder; multiple organ injury syndrome; hemolytic anemia (including, but not limited to cryoglobinemia or Coombs positive anemia); myasthenia gravis; antigen-antibody complex mediated diseases; anti-glomerular basement membrane disease; antiphospholipid syndrome; allergic neuritis; Graves' disease; Lambert-Eaton myasthenic syndrome; pemphigoid bullous; pemphigus; autoimmune polyendocrinopathies; Reiter's disease; stiff-man syndrome; Behcet disease; giant cell arteritis; immune complex nephritis; IgA nephropathy; IgM polyneuropathies; immune thrombocytopenic purpura (ITP) or autoimmune thrombocytopenia etc.

The terms "cancer" and "cancerous" refer to or describe the physiological condition in mammals that is typically characterized by unregulated cell growth. Included in this definition are benign and malignant cancers. By "early stage cancer" or "early stage tumor" is meant a cancer that is not invasive or metastatic or is classified as a Stage 0, I, or II cancer. Examples of cancer include, but are not limited to, carcinoma, lymphoma, blastoma (including medulloblastoma and retinoblastoma), sarcoma (including liposarcoma and synovial cell sarcoma), neuroendocrine tumors (including carcinoid tumors, gastrinoma, and islet cell cancer), mesothelioma, schwannoma (including acoustic neuroma), meningioma, adenocarcinoma, melanoma, and leukemia or lymphoid malignancies. More particular examples of such cancers include squamous cell cancer (e.g. epithelial squamous cell cancer), lung cancer including small-cell lung cancer (SCLC), non-small cell lung cancer (NSCLC), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer (including metastatic breast cancer), colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, testicular cancer, esophageal cancer, tumors of the biliary tract, as well as head and neck cancer and multiple myeloma.

The term "pre-cancerous" refers to a condition or a growth that typically precedes or develops into a cancer. A "pre-cancerous" growth will have cells that are characterized by abnormal cell cycle regulation, proliferation, or differentiation, which can be determined by markers of cell cycle regulation, cellular proliferation, or differentiation.

By "dysplasia" is meant any abnormal growth or development of tissue, organ, or cells. Preferably, the dysplasia is high grade or precancerous.

By "metastasis" is meant the spread of cancer from its primary site to other places in the body. Cancer cells can break away from a primary tumor, penetrate into lymphatic and blood vessels, circulate through the bloodstream, and grow in a distant focus (metastasize) in normal tissues elsewhere in the body. Metastasis can be local or distant. Metastasis is a sequential process, contingent on tumor cells breaking off from the primary tumor, traveling through the bloodstream, and stopping at a distant site. At the new site, the cells establish a blood supply and can grow to form a life-threatening mass.

Both stimulatory and inhibitory molecular pathways within the tumor cell regulate this behavior, and interactions between the tumor cell and host cells in the distant site are also significant.

By "non-metastatic" is meant a cancer that is benign or that remains at the primary site and has not penetrated into the lymphatic or blood vessel system or to tissues other than the primary site. Generally, a non-metastatic cancer is any cancer that is a Stage 0, I, or II cancer, and occasionally a Stage III cancer.

By "primary tumor" or "primary cancer" is meant the original cancer and not a metastatic lesion located in another tissue, organ, or location in the subject's body.

By "benign tumor" or "benign cancer" is meant a tumor that remains localized at the site of origin and does not have the capacity to infiltrate, invade, or metastasize to a distant site.

By "tumor burden" is meant the number of cancer cells, the size of a tumor, or the amount of cancer in the body. Tumor burden is also referred to as tumor load.

By "tumor number" is meant the number of tumors.

By "subject" is meant a mammal, including, but not limited to, a human or non-human mammal, such as a bovine, equine, canine, ovine, or feline. Preferably, the subject is a human.

The term "anti-cancer therapy" refers to a therapy useful in treating cancer. Examples of anti-cancer therapeutic agents include, but are limited to, e.g., chemotherapeutic agents, growth inhibitory agents, cytotoxic agents, agents used in radiation therapy, anti-angiogenesis agents, apoptotic agents, anti-tubulin agents, and other agents to treat cancer, anti-CD20 antibodies, platelet derived growth factor inhibitors (e.g., Gleevec™ (Imatinib Mesylate)), a COX-2 inhibitor (e.g., celecoxib), interferons, cytokines, antagonists (e.g., neutralizing antibodies) that bind to one or more of the following targets ErbB2, ErbB3, ErbB4, PDGFR-beta, BlyS, APRIL, BCMA or VEGF receptor(s), TRAIL/

Apo2, and other bioactive and organic chemical agents, etc. Combinations thereof are also included in the invention.

The term "cytotoxic agent" as used herein refers to a substance that inhibits or prevents the function of cells and/or causes destruction of cells. The term is intended to include radioactive isotopes (e.g., $I^{131}$, $I^{125}$, $Y^{90}$ and $Re^{186}$), chemotherapeutic agents, and toxins such as enzymatically active toxins of bacterial, fungal, plant or animal origin, or fragments thereof.

A "chemotherapeutic agent" is a chemical compound useful in the treatment of cancer. Examples of chemotherapeutic agents include is a chemical compound useful in the treatment of cancer. Examples of chemotherapeutic agents include alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaI1 (see, e.g., Agnew, *Chem Intl. Ed. Engl.,* 33: 183-186 (1994)); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® doxetaxel (Rhône-Poulenc Rorer, Antony, France); chloranbucil; GEMZAR® gemcitabine; 6-thioguanine; mercaptopurine; methotrexate; platinum analogs such as cisplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; VELCADE bortezomib; REVLIMID lenalidomide; leucovorin (LV); oxaliplatin, including the oxaliplatin treatment regimen (FOLFOX); inhibitors of PKC-alpha, Raf, H-Ras, EGFR (e.g., erlotinib (Tarceva™)) and VEGF-A that reduce cell proliferation and pharmaceutically acceptable salts, acids or derivatives of any of the above.

Also included in this definition are anti-hormonal agents that act to regulate or inhibit hormone action on tumors such as anti-estrogens and selective estrogen receptor modulators (SERMs), including, for example, tamoxifen (including NOLVADEX® tamoxifen), raloxifene, droloxifene, 4-hydroxytamoxifen, trioxifene, keoxifene, LY117018, onapristone, and FARESTON•toremifene; aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those which inhibit expression of genes in signaling pathways implicated in abherant cell proliferation, such as, for example, PKC-alpha, Raf and H-Ras; ribozymes such as a VEGF expression inhibitor (e.g., ANGIOZYME® ribozyme) and a HER2 expression inhibitor; vaccines such as gene therapy vaccines, for example, ALLOVECTIN® vaccine, LEUVECTIN® vaccine, and VAXID® vaccine; PROLEUKIN® rIL-2; LURTOTECAN® topoisomerase 1 inhibitor; ABARELIX® rmRH; Vinorelbine and Esperamicins (see U.S. Pat. No. 4,675,187), and pharmaceutically acceptable salts, acids or derivatives of any of the above.

The term "prodrug" as used in this application refers to a precursor or derivative form of a pharmaceutically active substance that is less cytotoxic to tumor cells compared to the parent drug and is capable of being enzymatically activated or converted into the more active parent form. See, e.g., Wilman, "Prodrugs in Cancer Chemotherapy" *Biochemical Society Transactions,* 14, pp. 375-382, 615th Meeting Belfast (1986) and Stella et al., "Prodrugs: A Chemical Approach to Targeted Drug Delivery," *Directed Drug Delivery,* Borchardt et al., (ed.), pp. 247-267, Humana Press (1985). The prodrugs of this invention include, but are not limited to, phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, those chemotherapeutic agents described above.

By "radiation therapy" is meant the use of directed gamma rays or beta rays to induce sufficient damage to a cell so as to limit its ability to function normally or to destroy the cell altogether. It will be appreciated that there will be many ways known in the art to determine the dosage and duration of treatment. Typical treatments are given as a one time administration and typical dosages range from 10 to 200 units (Grays) per day.

A "biologically active" or "functional" polypeptide (such as a heterologous polypeptide) is one capable of exerting one or more of its natural activities in structural, regulatory, biochemical or biophysical events.

A "biologically active" or "functional" antibody is one capable of exerting one or more of its natural activities in structural, regulatory, biochemical or biophysical events. For example, a biologically active antibody may have the ability to specifically bind an antigen and the binding may in turn elicit or alter a cellular or molecular event such as signaling transduction or enzymatic activity. A biologically active antibody may also block ligand activation of a receptor or act as an agonist antibody. The capability of a antibody to exert one or more of its natural activities depends on several factors, including proper folding and assembly of the polypeptide chains. As used herein, the biologically active antibody generated by the disclosed methods typically comprise heterotetramers having two identical L chains and two identical H chains that are linked by multiple disulfide bonds and properly folded.

Compositions of the Invention and Methods Using Same

In one aspect, the present invention provides TIR variants. Thus, for a given TIR, a series of amino acid or nucleic acid sequence variants can be created with a range of translational strengths, thereby providing a convenient means by which to adjust this factor for the optimal secretion of many different polypeptides. The use of a reporter gene expressed under the control of these variants, such as PhoA, provides a method to quantitate the relative translational strengths of different translation initiation regions. The variant or mutant TIRs can be provided in the background of a plasmid vector thereby providing a set of plasmids into which a gene of interest may be inserted and its expression measured, so as to establish an optimum range of translational strengths for maximal expression of mature polypeptide.

Mutagenesis of the TIR is done by conventional techniques that result in codon changes which can alter the amino acid sequence, although silent changes in the nucleotide sequence are preferred. Alterations in the TIR can include, for example, alterations in the number or spacing of Shine-Dalgarno sequences, along with alterations in the signal sequence. One method for generating mutant signal sequences is the generation of a "codon bank" at the beginning of a coding sequence that does not change the amino acid sequence of the signal sequence (i.e., the changes are silent). This can be accomplished by changing the third nucleotide position of each codon; additionally, some amino acids, such as leucine, serine, and arginine, have multiple first and second positions that can add complexity in making the bank. This method of mutagenesis is described in detail in Yansura et al. (METHODS: A Companion to Methods in Enzymol. 4:151-158 (1992)). Basically, a DNA fragment encoding the signal sequence and the beginning of the mature polypeptide is synthesized such that the third (and, possibly, the first and second, as described above) position of each of the first 6 to 12 codons is altered. The additional nucleotides downstream of these codons provide a site for the binding of a complementary primer used in making the bottom strand. Treatment of the top coding strand and the bottom strand primer with DNA polymerase I (Klenow) will result in a set of duplex DNA fragments containing randomized codons. The primers are designed to contain useful cloning sites that can then be used to insert the DNA fragments in an appropriate vector, thereby allowing amplification of the codon bank. Alternative methods include, for example, replacement of the entire rbs with random nucleotides (Wilson et al., BioTechniques 17:944-952 (1994)), and the use of phage display libraries (see, for example, Barbas et al., Proc. Natl. Acad. Sci. U.S.A. 89:4457-4461 (1992); Garrard et al., Gene 128:103-109 (1993)).

The bacterial Sec translocase facilitates protein export in prokaryotes. Secretory proteins can be targeted to the Sec translocase by two different mechanisms, ie, the co-translational and the post-translational targeting. In the latter, the signal sequence containing secretory protein is released from the ribosome in its synthesis completed state and directed to the Sec-translocase. In various Gram-negative bacteria, secretory proteins are guided to the Sec-translocase by the secretion specific chaperone SecB that maintains these proteins in a translocation-competent, unfolded state. During co-translational targeting, the signal recognition particle (SRP) binds to the signal sequence of the secretory protein while it emerges from the ribosome and the entire ternary complex of SRP/ribosome/nascent secretory protein chain is targeted to the Sec-translocase.

For example, the maltose-binding periplasmic protein (MalE) and alkaline phosphatase (PhoA) signal peptides direct translocation from the cytoplasm to the periplasm in a post-translational manner with the aid of the molecular motor SecA. Other exemplary signal peptides that direct translocation in a post-translational manner are dsbC, lolA, ompA, lamb, and lpp. The heat-stable enterotoxin II (stII) and thiol:disulfide interchange protein (dsbA) signal peptides direct translocation in a co-translational manner with aid from the signal recognition particle (SRP). Other exemplary signal peptides that direct translocation in a co-translational manner are yraI, tort, tolB, sfmC, nikA, and sfmC. See also Natale et al. for a review of Sec- and Tat-mediated protein secretion across the bacterial cytoplasmic membrane. (Natale et al. (2008) Biochemica et Biophysica Acta 1778:1735-56.)

We developed novel variant translational initiation region (TIR) signal peptide libraries (FIG. 2, Table 2) for signal peptides representing two of the major secretion pathways for transport across the inner-membrane in *E. coli*: sec (PhoA, MalE) and SRP (DsbA, STII). Each library comprises a panel of vectors with comprising variant TIRs of differing translational strengths, providing a means by which to readily adjust level of translation for a given protein of interest.

Typically, the TIR variants will be provided in a plasmid vector with appropriate elements for expression of a gene of interest. For example, a typical construct will contain a promoter 5' to the signal sequence, a restriction enzyme recognition site 3' to the signal sequence for insertion of a gene of interest or a reporter gene, and a selectable marker, such as a drug resistance marker, for selection and/or maintenance of bacteria transformed with the resulting plasmids. Plasmid vectors are further discussed and exemplified herein. Promoters suitable for use with prokaryotic hosts are known in the art and some are exemplified and described herein.

Any reporter gene may be used which can be quantified in some manner. Thus, for example, alkaline phosphatase production can be quantitated as a measure of the secreted level of the phoA gene product. Other examples include, for example, the β-lactamase genes.

Generally, a set of vectors may be generated with a range of TIR strengths for each cistron of the vector therein. This limited set provides a comparison of expression levels of each chain as well as the yield of full length products under various TIR strength combinations. TIR strengths can be determined by quantifying the expression level of a reporter gene as described in detail in Simmons et al. U.S. Pat. No. 5,840,523. For the purpose of this invention, the translational strength combination for a particular pair of TIRs within a vector is represented by (N-light, M-heavy), wherein N is the relative TIR strength of light chain and M is the relative TIR strength of heavy chain. For example, (3-light, 7-heavy) means the vector provides a relative TIR strength of about 3 for light chain expression and a relative TIR strength of about 7 for heavy chain expression. Based on the translational strength comparison, the desired individual TIRs are selected to be combined in the expression vector constructs of the invention. Vectors so constructed can be used to transform an appropriate host. Preferably, the host is a prokaryotic host. More preferably, the host is *E. coli*.

The secreted level of polypeptides can be determined, for example, by a functional assays for the polypeptide of interest, if available, radioimmunoassays (RIA), enzyme-linked immunoassays (ELISA), or by PAGE and visualization of the correct molecular weight of the polypeptide of interest. Methods for determining level of secreted polypeptide are well known in the art and some are exemplified herein.

Antibodies

The antibodies of the invention are preferably monoclonal. Also encompassed within the scope of the invention are Fab, Fab', Fab'-SH and F(ab')$_2$ fragments of the antibodies provided herein. These antibody fragments can be created by traditional means, such as enzymatic digestion, or may be generated by recombinant techniques. Such antibody fragments may be chimeric or humanized. These fragments are useful for the diagnostic and therapeutic purposes set forth below.

Accordingly, in some embodiment, the anti-c-met antibody is a one-armed antibody (i.e., the heavy chain variable domain and the light chain variable domain form a single antigen binding arm) comprising an Fc region, wherein the Fc region comprises a first and a second Fc polypeptide, wherein the first and second Fc polypeptides are present in a complex and form a Fc region that increases stability of said antibody fragment compared to a Fab molecule comprising said antigen binding arm. For treatment of pathological conditions requiring an antagonistic function, and where bivalency of an antibody results in an undesirable agonistic effect, the monovalent trait of a one-armed antibody (i.e., an antibody comprising a single antigen binding arm) results in and/or ensures an antagonistic function upon binding of the antibody to a target molecule. Furthermore, the one-armed antibody comprising a Fc region is characterized by superior pharmacokinetic attributes (such as an enhanced half life and/or reduced clearance rate in vivo) compared to Fab forms having similar/substantially identical antigen binding characteristics, thus overcoming a major drawback in the use of conventional monovalent Fab antibodies. One-armed antibodies are disclosed in, for example, WO2005/063816; Martens et al, Clin Cancer Res (2006), 12: 6144. In some embodiments, the one armed antibody is a monovalent antibody fragment, wherein the antibody fragment comprises a first polypeptide comprising a light chain variable domain, a second polypeptide comprising a heavy chain variable domain and said first Fc polypeptide, and a third polypeptide comprising said second Fc polypeptide, whereby the heavy chain variable domain and the light chain variable domain form a single antigen binding arm, and whereby the first and second Fc polypeptides are present in a complex and form a Fc region that increases stability of said antibody fragment compared to a Fab molecule comprising said antigen binding arm.

In some embodiments, the antibody binds (in some embodiments, specifically binds) c-met. In some embodiments, the anti-c-met antibody comprises (a) a first polypeptide comprising a heavy chain variable domain having the sequence: EVQLVESGGGLVQPGGSLRLSCAAS-GYTFTSYWLHWVRQAPGKGLEWVGMIDPS NSDTRFNPNFKDRFTISADTSKNTAYLQMNSLRAED-TAVYYCATYRSYVTPLDYW GQGTLVTVSS (SEQ ID NO: 43), CH1 sequence, and a first Fc polypeptide; (b) a second polypeptide comprising a light chain variable domain having the sequence: DIQMTQSPSSLSAS-VGDRVTITCKSSQSLLYTSSQKNYLAWYQQKPGKAP-KLLIYW ASTRESGVPSRFSGSGSGTDFTLTISS-LQPEDFATYYCQQYYAYPWTFGQGTKVEIK R (SEQ ID NO: 44), and CL1 sequence; and (c) a third polypeptide comprising a second Fc polypeptide, wherein the heavy chain variable domain and the light chain variable domain are present as a complex and form a single antigen binding arm, wherein the first and second Fc polypeptides are present in a complex and form a Fc region that increases stability of said antibody fragment compared to a Fab molecule comprising said antigen binding arm. In some embodiments, the first polypeptide comprises the Fc sequence depicted in FIG. 7 (SEQ ID NO: 68) and the second polypeptide comprises the Fc sequence depicted in FIG. 8 (SEQ ID NO: 47). In some embodiments, the first polypeptide comprises the Fc sequence depicted in FIG. 8 (SEQ ID NO: 47) and the second polypeptide comprises the Fc sequence depicted in FIG. 7 (SEQ ID NO: 68).

In some embodiments, the anti-c-met antibody comprises (a) a first polypeptide comprising a heavy chain variable domain, said polypeptide comprising the sequence: EVQLVESGGGLVQPGGSLRLSCAASGYTFTSYWLH-WVRQAPGKGLEWVGMIDPS NSDTRFNPNFKDRFTI-SADTSKNTAYLQMNSLRAEDTAVYYCATYRSYVT-PLDYW
GQGTLVTVSSASTKGPSVFPLAPSSKSTSGGTAALG-CLVKDYFPEPVTVSWNSGAL TSGVHTFPAVLQSS-GLYSLSSVVTVPSSSLGTQTYICNVNHKPSNTKVDK-KVEPKS
CDKTHTCPPCPAPELLGGPSVFLFPPKPKDTLMISRT-PEVTCVVVDVSHEDPEVKFN WYVDGVEVHNAKTK-PREEQYNSTYRVVSVLTVLHQDWLNGKEYKCK-VSNKALP
APIEKTISKAKGQPREPQVYTLPPSREEMTKNQVSLS-CAVKGFYPSDIAVEWESNG QPENNYKTTPPVLDS- DGSFFLVSKLTVDKSRWQQGNVFSCSVMHEALHN-HYTQKS LSLSPGK (SEQ ID NO: 45); (b) a second polypeptide comprising a light chain variable domain, the polypeptide comprising the sequence DIQMTQSPSSLSAS-VGDRVTITCKSSQSLLYTSSQKNYLAWYQQKPGKAP-KLLIYW ASTRESGVPSRFSGSGSGTDFTLTISS-LQPEDFATYYCQQYYAYPWTFGQGTKVEIK RTVAAPSVFIFPPSDEQLKSGTASVVCLLNNFY-PREAKVQWKVDNALQSGNSQESV TEQDSKD-STYSLSSTLTLSKADYEKHKVY-ACEVTHQGLSSPVTKSFNRGEC (SEQ ID NO: 46); and a third polypeptide comprising a Fc sequence, the polypeptide comprising the sequence DKTHTCPPCPAPELLGGPS-VFLFPPKPKDTLMISRTPEVTCVVVDVSHEDPEVKFN WYVDGVEVHNAKTKPREEQYNSTYRVVSVLTVL-HQDWLNGKEYKCKVSNKALP APIEKTISKAK-GQPREPQVYTLPPSREEMTKNQVSLWCLVKGFYPS-DIAVEWESNG QPENNYKTTPPVLDSDGSFFLYSKLTVDKSRWQQGN-VFSCSVMHEALHNHYTQKS LSLSPGK (SEQ ID NO: 47), wherein the heavy chain variable domain and the light chain variable domain are present as a complex and form a single antigen binding arm, wherein the first and second Fc polypeptides are present in a complex and form a Fc region that increases stability of said antibody fragment compared to a Fab molecule comprising said antigen binding arm.

In one aspect, the anti-c-met antibody comprises:

(a) at least one, two, three, four or five hypervariable region (CDR) sequences selected from the group consisting of:

(i) CDR-L1 comprising sequence A1-A17, wherein A1-A17 is KSSQSLLYTSSQKNYLA (SEQ ID NO:49)

(ii) CDR-L2 comprising sequence B1-B7, wherein B1-B7 is WASTRES (SEQ ID NO:50)

(iii) CDR-L3 comprising sequence C1-C9, wherein C1-C9 is QQYYAYPWT (SEQ ID NO:51)

(iv) CDR-H1 comprising sequence D1-D10, wherein D1-D10 is GYTFTSYWLH (SEQ ID NO:52)

(v) CDR-H2 comprising sequence E1-E 18, wherein E1-E 18 is GMIDPSNSDTRFNPNFKD (SEQ ID NO:53) and (vi) CDR-H3 comprising sequence F1-F11, wherein F1-F11 is T/SYGSYVSPLDY (SEQ ID NO:54);

and (b) at least one variant CDR, wherein the variant CDR sequence comprises modification of at least one residue of the sequence depicted in (i)-(vi). In one embodiment, CDR-H3 comprises TYGSYVSPLDY (SEQ ID NO: 55). In one embodiment, CDR-H3 comprises SYGSYVSPLDY (SEQ ID NO: 56). In one embodiment, an antibody of the invention comprising these sequences (in combination as described herein) is humanized or human.

In one embodiment, the anti-c-met antibody comprises a heavy chain variable domain comprising one or more of CDR1-HC, CDR2-HC and CDR3-HC sequence depicted in FIG. 7 (SEQ ID NO: 52-53 & 66). In some embodiments, the antibody comprises a light chain variable domain comprising one or more of CDR1-LC, CDR2-LC and CDR3-LC sequence depicted in FIG. 7 (SEQ ID NOs: 49-51). In some embodiments, the heavy chain variable domain comprises FR1-HC, FR2-HC, FR3-HC and FR4-HC sequence depicted in FIG. 7 (SEQ ID NOs: 62-65). In some embodiments, the light chain variable domain comprises FR1-LC, FR2-LC, FR3-LC and FR4-LC sequence depicted in FIG. 7 (SEQ ID NOs: 57-60).

Variant HVRs in an anti-c-met antibody of the invention can have modifications of one or more residues within the HVR. In one embodiment, a HVR-L2 variant comprises 1-5 (1, 2, 3, 4 or 5) substitutions in any combination of the following positions: B1 (M or L), B2 (P, T, G or S), B3 (N, G, R or T), B4 (I, N or F), B5 (P, I, L or G), B6 (A, D, T or V) and B7 (R, I, M or G). In one embodiment, a HVR-H1 variant comprises 1-5 (1, 2, 3, 4 or 5) substitutions in any combination of the following positions: D3 (N, P, L, S, A, I), D5 (I, S or Y), D6 (G, D, T, K, R), D7 (F, H, R, S, T or V) and D9 (M or V). In one embodiment, a HVR-H2 variant comprises 1-4 (1, 2, 3 or 4) substitutions in any combination of the following positions: E7 (Y), E9 (I), E10 (I), E14 (T or Q), E15 (D, K, S, T or V), E16 (L), E17 (E, H, N or D) and E18 (Y, E or H). In one embodiment, a HVR-H3 variant comprises 1-5 (1, 2, 3, 4 or 5) substitutions in any combination of the following positions: F1 (T, S), F3 (R, S, H, T, A, K), F4 (G), F6 (R, F, M, T, E, K, A, L, W), F7 (L, I, T, R, K, V), F8 (S, A), F10 (Y, N) and F11 (Q, S, H, F). Letter(s) in parenthesis following each position indicates an illustrative substitution (i.e., replacement) amino acid; as would be evident to one skilled in the art, suitability of other amino acids as substitution amino acids in the context described herein can be routinely assessed using techniques known in the art and/or described herein. In one embodiment, a HVR-L1 comprises the sequence of SEQ ID NO:49. In one embodiment, F1 in a variant HVR-H3 is T. In one embodiment, F1 in a variant HVR-H3 is S. In one embodiment, F3 in a variant HVR-H3 is R. In one embodiment, F3 in a variant HVR-H3 is S. In one embodiment, F7 in a variant HVR-H3 is T. In one embodiment, an antibody of the invention comprises a variant HVR-H3 wherein F1 is T or S, F3 is R or S, and F7 is T.

In one embodiment, an anti-c-met antibody of the invention comprises a variant HVR-H3 wherein F1 is T, F3 is R and F7 is T. In one embodiment, an antibody of the invention comprises a variant HVR-H3 wherein F1 is S. In one embodiment, an antibody of the invention comprises a variant HVR-H3 wherein F1 is T, and F3 is R. In one embodiment, an antibody of the invention comprises a variant HVR-H3 wherein F1 is S, F3 is R and F7 is T. In one embodiment, an antibody of the invention comprises a variant HVR-H3 wherein F1 is T, F3 is S, F7 is T, and F8 is S. In one embodiment, an antibody of the invention comprises a variant HVR-H3 wherein F1 is T, F3 is S, F7 is T, and F8 is A. In some embodiments, said variant HVR-H3 antibody further comprises HVR-L1, HVR-L2, HVR-L3, HVR-H1 and HVR-H2 wherein each comprises, in order, the sequence depicted in SEQ ID NOs:49, 50, 51, 52, and 53. In some embodiments, these antibodies further comprise a human subgroup III heavy chain framework consensus sequence. In one embodiment of these antibodies, the framework consensus sequence comprises substitution at position 71, 73 and/or 78. In some embodiments of these antibodies, position 71 is A, 73 is T and/or 78 is A. In one embodiment of these antibodies, these antibodies further comprise a human κI light chain framework consensus sequence.

In one embodiment, an anti-c-met antibody of the invention comprises a variant HVR-L2 wherein B6 is V. In some embodiments, said variant HVR-L2 antibody further comprises HVR-L1, HVR-L3, HVR-H1, HVR-H2 and HVR-H3, wherein each comprises, in order, the sequence depicted in SEQ ID NOs: 49, 51, 52, 53, 54. In some embodiments, said variant HVR-L2 antibody further comprises HVR-L1, HVR-L3, HVR-H1, HVR-H2 and HVR-H3, wherein each comprises, in order, the sequence depicted in SEQ ID NOs: 49, 51, 52, 53, 55. In some embodiments, said variant HVR-L2 antibody further comprises HVR-L1, HVR-L3, HVR-H1, HVR-H2 and HVR-H3, wherein each comprises, in order, the sequence depicted in SEQ ID NOs: 49, 51, 52, 53, 56. In some embodiments, these antibodies further comprise a human subgroup III heavy chain framework consensus sequence. In one embodiment of these antibodies, the framework consensus sequence comprises substitution at position 71, 73 and/or 78. In some embodiments of these antibodies, position 71 is A, 73 is T and/or 78 is A. In one embodiment of these antibodies, these antibodies further comprise a human id light chain framework consensus sequence.

In one embodiment, an anti-cmet antibody of the invention comprises a variant HVR-H2 wherein E14 is T, E15 is K and E11 is E. In one embodiment, an antibody of the invention comprises a variant HVR-H2 wherein E11 is E. In some embodiments, said variant HVR-H3 antibody further comprises HVR-L1, HVR-L2, HVR-L3, HVR-H1, and HVR-H3 wherein each comprises, in order, the sequence depicted in SEQ ID NOs: 49, 50, 51, 52, 54. In some embodiments, said variant HVR-H2 antibody further comprises HVR-L1, HVR-L2, HVR-L3, HVR-H1, and HVR-H3, wherein each comprises, in order, the sequence depicted in SEQ ID NOs: 49, 50, 51, 52, 55. In some embodiments, said variant HVR-H2 antibody further comprises HVR-L1, HVR-L2, HVR-L3, HVR-H1, and HVR-H3, wherein each comprises, in order, the sequence depicted in SEQ ID NOs: 49, 50, 51, 52, 55. In some embodiments, these antibodies further comprise a human subgroup III heavy chain framework consensus sequence. In one embodiment of these antibodies, the framework consensus sequence comprises substitution at position 71, 73 and/or 78. In some embodiments of these antibodies, position 71 is A, 73 is T and/or 78 is A. In one embodiment of these antibodies, these antibodies further comprise a human κI light chain framework consensus sequence.

Other anti-c-met antibodies suitable for use in the methods of the invention are known in the art.

In one aspect, the anti-c-met antibody comprises at least one characteristic that promotes heterodimerization, while minimizing homodimerization, of the Fc sequences within the antibody fragment. Such characteristic(s) improves yield and/or purity and/or homogeneity of the immunoglobulin populations. In one embodiment, the antibody comprises Fc mutations constituting "knobs" and "holes" as described in WO2005/063816. For example, a hole mutation can be one or more of T366A, L368A and/or Y407V in an Fc polypeptide, and a knob mutation can be T366W. Knob and hole Fc mutations are further described herein.

Monoclonal antibodies are obtained from a population of substantially homogeneous antibodies, i.e., the individual antibodies comprising the population are identical except for possible naturally occurring mutations that may be present in minor amounts. Thus, the modifier "monoclonal" indicates the character of the antibody as not being a mixture of discrete antibodies.

The monoclonal antibodies of the invention can be made using the hybridoma method first described by Kohler et al., *Nature*, 256:495 (1975), or may be made by recombinant DNA methods (U.S. Pat. No. 4,816,567).

In the hybridoma method, a mouse or other appropriate host animal, such as a hamster, is immunized to elicit lymphocytes that produce or are capable of producing antibodies that will specifically bind to the protein used for immunization. Antibodies to antigen may be raised in animals by multiple subcutaneous (sc) or intraperitoneal (ip) injections of antigen and an adjuvant. Antigen may be prepared using methods well-known in the art, some of which are further described herein. For example, recombinant production of human and mouse antigen is described below. In one embodiment, animals are immunized with a antigen fused to the Fc portion of an immunoglobulin heavy chain. In a preferred embodiment, animals are immunized with a antigen-IgG1 fusion protein. Animals ordinarily are immunized against immunogenic conjugates or derivatives of antigen with monophosphoryl lipid A (MPL)/trehalose dicrynomycolate (TDM) (Ribi Immunochem. Research, Inc., Hamilton, Mont.) and the solution is injected intradermally at multiple sites. Two weeks later the animals are boosted. 7 to 14 days later animals are bled and the serum is assayed for antibody titer. Animals are boosted until titer plateaus.

Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice*, pp. 59-103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, *J. Immunol.*, 133:3001 (1984); Brodeur et al., *Monoclonal Antibody Production Techniques and Applications*, pp. 51-63 (Marcel Dekker, Inc., New York, 1987)).

Culture medium in which hybridoma cells are growing is assayed for production of monoclonal antibodies directed against antigen. Preferably, the binding specificity of monoclonal antibodies produced by hybridoma cells is determined by immunoprecipitation or by an in vitro binding assay, such as radioimmunoassay (RIA) or enzyme-linked immunoadsorbent assay (ELISA).

The binding affinity of the monoclonal antibody can, for example, be determined by the Scatchard analysis of Munson et al., *Anal. Biochem.*, 107:220 (1980).

After hybridoma cells are identified that produce antibodies of the desired specificity, affinity, and/or activity, the clones may be subcloned by limiting dilution procedures and grown by standard methods (Goding, *Monoclonal Antibodies: Principles and Practice*, pp. 59-103 (Academic Press, 1986)). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

The antibodies of the invention can be made by using combinatorial libraries to screen for synthetic antibody clones with the desired activity or activities. In principle, synthetic antibody clones are selected by screening phage libraries containing phage that display various fragments of antibody variable region (Fv) fused to phage coat protein. Such phage libraries are panned by affinity chromatography against the desired antigen. Clones expressing Fv fragments capable of binding to the desired antigen are adsorbed to the antigen and thus separated from the non-binding clones in the library. The binding clones are then eluted from the antigen, and can be further enriched by additional cycles of antigen adsorption/elution. Any of the antibodies of the invention can be obtained by designing a suitable antigen screening procedure to select for the phage clone of interest followed by construction of a antibody clone using the Fv sequences from the phage clone of interest and suitable constant region (Fc) sequences described in Kabat et al., *Sequences of Proteins of Immunological Interest*, Fifth Edition, NIH Publication 91-3242, Bethesda Md. (1991), vols. 1-3. An exemplary method for generating antibodies is disclosed in the Examples.

The antigen-binding domain of an antibody is formed from two variable (V) regions of about 110 amino acids, one each from the light (VL) and heavy (VH) chains, that both present three hypervariable loops or complementarity-determining regions (CDRs). Variable domains can be displayed functionally on phage, either as single-chain Fv (scFv) fragments, in which VH and VL are covalently linked through a short, flexible peptide, or as Fab fragments, in which they are each fused to a constant domain and interact non-covalently, as described in Winter et al., *Ann. Rev. Immunol.*, 12: 433-455 (1994). As used herein, scFv encoding phage clones and Fab encoding phage clones are collectively referred to as "Fv phage clones" or "Fv clones".

Repertoires of VH and VL genes can be separately cloned by polymerase chain reaction (PCR) and recombined randomly in phage libraries, which can then be searched for antigen-binding clones as described in Winter et al., *Ann. Rev. Immunol.*, 12: 433-455 (1994). Libraries from immunized sources provide high-affinity antibodies to the immunogen without the requirement of constructing hybridomas. Alternatively, the naive repertoire can be cloned to provide a single source of human antibodies to a wide range of non-self and also self antigens without any immunization as described by Griffiths et al., *EMBO J*, 12: 725-734 (1993). Finally, naive libraries can also be made synthetically by cloning the unrearranged V-gene segments from stem cells, and using PCR primers containing random sequence to encode the highly variable CDR3 regions and to accomplish rearrangement in vitro as described by Hoogenboom and Winter, *J. Mol. Biol.*, 227: 381-388 (1992).

Filamentous phage is used to display antibody fragments by fusion to the minor coat protein pIII. The antibody fragments can be displayed as single chain Fv fragments, in which VH and VL domains are connected on the same polypeptide chain by a flexible polypeptide spacer, e.g., as described by Marks et al., *J. Mol. Biol.*, 222: 581-597 (1991), or as Fab fragments, in which one chain is fused to pIII and the other is secreted into the bacterial host cell periplasm where assembly of a Fab-coat protein structure which becomes displayed on the phage surface by displacing some of the wild type coat proteins, e.g., as described in Hoogenboom et al., *Nucl. Acids Res.*, 19: 4133-4137 (1991).

In general, nucleic acids encoding antibody gene fragments are obtained from immune cells harvested from humans or animals. If a library biased in favor of clones targeting a particular antigen is desired, the individual is immunized with antigen to generate an antibody response, and spleen cells and/or circulating B cells other peripheral blood lymphocytes (PBLs) are recovered for library construction. In a preferred embodiment, a human antibody gene fragment library biased in favor of antigen-reactive clones is obtained by generating an antibody response in transgenic mice carrying a functional human immunoglobulin gene array (and lacking a functional endogenous antibody production system) such that antigen immunization gives rise to B cells producing human antibodies against antigen. The generation of human antibody-producing transgenic mice is described below.

Additional enrichment for antigen reactive cell populations can be obtained by using a suitable screening procedure to isolate B cells expressing antigen-specific membrane bound antibody, e.g., by cell separation with antigen affinity chromatography or adsorption of cells to fluorochrome-labeled antigen followed by flow-activated cell sorting (FACS).

Alternatively, the use of spleen cells and/or B cells or other PBLs from an unimmunized donor provides a better representation of the possible antibody repertoire, and also permits the construction of an antibody library using any animal (human or non-human) species in which antigen is not antigenic. For libraries incorporating in vitro antibody gene construction, stem cells are harvested from the individual to provide nucleic acids encoding unrearranged antibody gene segments. The immune cells of interest can be obtained from a variety of animal species, such as human, mouse, rat, lagomorpha, luprine, canine, feline, porcine, bovine, equine, and avian species, etc.

Nucleic acid encoding antibody variable gene segments (including VH and VL segments) are recovered from the cells of interest and amplified. In the case of rearranged VH and VL gene libraries, the desired DNA can be obtained by isolating genomic DNA or mRNA from lymphocytes followed by polymerase chain reaction (PCR) with primers matching the 5' and 3' ends of rearranged VH and VL genes as described in Orlandi et al., *Proc. Natl. Acad. Sci. (USA)*, 86: 3833-3837 (1989), thereby making diverse V gene repertoires for expression. The V genes can be amplified from cDNA and genomic DNA, with back primers at the 5' end of the exon encoding the mature V-domain and forward primers based within the J-segment as described in Orlandi et al. (1989) and in Ward et al., *Nature,* 341: 544-546 (1989). However, for amplifying from cDNA, back primers can also be based in the leader exon as described in Jones et al., *Biotechnol.,* 9: 88-89 (1991), and forward primers within the constant region as described in Sastry et al., *Proc. Natl. Acad. Sci. (USA)*, 86: 5728-5732 (1989). To maximize complementarity, degeneracy can be incorporated in the primers as described in Orlandi et al. (1989) or Sastry et al. (1989). Preferably, the library diversity is maximized by using PCR primers targeted to each V-gene family in order to amplify all available VH and VL arrangements present in the immune cell nucleic acid sample, e.g. as described in the method of Marks et al., *J. Mol. Biol.*, 222: 581-597 (1991) or as described in the method of Orum et al., *Nucleic Acids Res.*, 21: 4491-4498 (1993). For cloning of the amplified DNA into expression vectors, rare restriction sites can be introduced within the PCR primer as a tag at one end as described in Orlandi et al. (1989), or by further PCR amplification with a tagged primer as described in Clackson et al., *Nature,* 352: 624-628 (1991).

Repertoires of synthetically rearranged V genes can be derived in vitro from V gene segments. Most of the human VH-gene segments have been cloned and sequenced (reported in Tomlinson et al., *J. Mol. Biol.*, 227: 776-798

(1992)), and mapped (reported in Matsuda et al., *Nature Genet.*, 3: 88-94 (1993); these cloned segments (including all the major conformations of the H1 and H2 loop) can be used to generate diverse VH gene repertoires with PCR primers encoding H3 loops of diverse sequence and length as described in Hoogenboom and Winter, *J. Mol. Biol.*, 227: 381-388 (1992). VH repertoires can also be made with all the sequence diversity focused in a long H3 loop of a single length as described in Barbas et al., *Proc. Natl. Acad. Sci. USA*, 89: 4457-4461 (1992). Human Vκ and Vλ segments have been cloned and sequenced (reported in Williams and Winter, *Eur. J. Immunol.*, 23: 1456-1461 (1993)) and can be used to make synthetic light chain repertoires. Synthetic V gene repertoires, based on a range of VH and VL folds, and L3 and H3 lengths, will encode antibodies of considerable structural diversity. Following amplification of V-gene encoding DNAs, germline V-gene segments can be rearranged in vitro according to the methods of Hoogenboom and Winter, *J. Mol. Biol.*, 227: 381-388 (1992).

Repertoires of antibody fragments can be constructed by combining VH and VL gene repertoires together in several ways. Each repertoire can be created in different vectors, and the vectors recombined in vitro, e.g., as described in Hogrefe et al., *Gene*, 128:119-126 (1993), or in vivo by combinatorial infection, e.g., the loxP system described in Waterhouse et al., *Nucl. Acids Res.*, 21:2265-2266 (1993). The in vivo recombination approach exploits the two-chain nature of Fab fragments to overcome the limit on library size imposed by *E. coli* transformation efficiency. Naive VH and VL repertoires are cloned separately, one into a phagemid and the other into a phage vector. The two libraries are then combined by phage infection of phagemid-containing bacteria so that each cell contains a different combination and the library size is limited only by the number of cells present (about $10^{12}$ clones). Both vectors contain in vivo recombination signals so that the VH and VL genes are recombined onto a single replicon and are co-packaged into phage virions. These huge libraries provide large numbers of diverse antibodies of good affinity ($K_d^{-1}$ of about $10^{-8}$ M).

Alternatively, the repertoires may be cloned sequentially into the same vector, e.g., as described in Barbas et al., *Proc. Natl. Acad. Sci. USA*, 88:7978-7982 (1991), or assembled together by PCR and then cloned, e.g. as described in Clackson et al., *Nature*, 352: 624-628 (1991). PCR assembly can also be used to join VH and VL DNAs with DNA encoding a flexible peptide spacer to form single chain Fv (scFv) repertoires. In yet another technique, "in cell PCR assembly" is used to combine VH and VL genes within lymphocytes by PCR and then clone repertoires of linked genes as described in Embleton et al., *Nucl. Acids Res.*, 20:3831-3837 (1992).

The antibodies produced by naive libraries (either natural or synthetic) can be of moderate affinity ($K_d^{-1}$ of about $10^6$ to $10^7$ M$^{-1}$), but affinity maturation can also be mimicked in vitro by constructing and reselecting from secondary libraries as described in Winter et al. (1994), supra. For example, mutations can be introduced at random in vitro by using error-prone polymerase (reported in Leung et al., *Technique*, 1:11-15 (1989)) in the method of Hawkins et al., *J. Mol. Biol.*, 226: 889-896 (1992) or in the method of Gram et al., *Proc. Natl. Acad. Sci USA*, 89: 3576-3580 (1992). Additionally, affinity maturation can be performed by randomly mutating one or more CDRs, e.g. using PCR with primers carrying random sequence spanning the CDR of interest, in selected individual Fv clones and screening for higher affinity clones. WO 96/07754 (published 14 Mar. 1996) described a method for inducing mutagenesis in a complementarity determining region of an immunoglobulin light chain to create a library of light chain genes. Another effective approach is to recombine the VH or VL domains selected by phage display with repertoires of naturally occurring V domain variants obtained from unimmunized donors and screen for higher affinity in several rounds of chain reshuffling as described in Marks et al., *Biotechnol.*, 10:779-783 (1992). This technique allows the production of antibodies and antibody fragments with affinities in the $10^{-9}$ M range.

Nucleic acid sequence encoding the desired target antigen can be designed using the amino acid sequence of the desired region of antigen.

Nucleic acids encoding target antigen can be prepared by a variety of methods known in the art. These methods include, but are not limited to, chemical synthesis by any of the methods described in Engels et al., *Agnew. Chem. Int. Ed. Engl.*, 28: 716-734 (1989), such as the triester, phosphite, phosphoramidite and H-phosphonate methods. In one embodiment, codons preferred by the expression host cell are used in the design of the antigen encoding DNA. Alternatively, DNA encoding the antigen can be isolated from a genomic or cDNA library.

Following construction of the DNA molecule encoding the antigen, the DNA molecule is operably linked to an expression control sequence in an expression vector, such as a plasmid, wherein the control sequence is recognized by a host cell transformed with the vector. In general, plasmid vectors contain replication and control sequences which are derived from species compatible with the host cell. The vector ordinarily carries a replication site, as well as sequences which encode proteins that are capable of providing phenotypic selection in transformed cells. Suitable vectors for expression in prokaryotic and eukaryotic host cells are known in the art and some are further described herein. Eukaryotic organisms, such as yeasts, or cells derived from multicellular organisms, such as mammals, may be used.

Optionally, the DNA encoding the antigen is operably linked to a secretory leader sequence resulting in secretion of the expression product by the host cell into the culture medium. Examples of secretory leader sequences include stII, ecotin, lamB, herpes GD, lpp, alkaline phosphatase, invertase, and alpha factor. Also suitable for use herein is the 36 amino acid leader sequence of protein A (Abrahmsen et al., *EMBO J.*, 4: 3901 (1985)).

Host cells are transfected and preferably transformed with the above-described expression or cloning vectors of this invention and cultured in conventional nutrient media modified as appropriate for inducing promoters, selecting transformants, or amplifying the genes encoding the desired sequences.

Transfection refers to the taking up of an expression vector by a host cell whether or not any coding sequences are in fact expressed. Numerous methods of transfection are known to the ordinarily skilled artisan, for example, $CaPO_4$ precipitation and electroporation. Successful transfection is generally recognized when any indication of the operation of this vector occurs within the host cell. Methods for transfection are well known in the art, and some are further described herein.

Transformation means introducing DNA into an organism so that the DNA is replicable, either as an extrachromosomal element or by chromosomal integrant. Depending on the host cell used, transformation is done using standard techniques appropriate to such cells. Methods for transformation are well known in the art, and some are further described herein.

Prokaryotic host cells used to produce the antigen can be cultured as described generally in Sambrook et al., supra.

The mammalian host cells used to produce the antigen can be cultured in a variety of media, which is well known in the art and some of which is described herein.

The host cells referred to in this disclosure encompass cells in in vitro culture as well as cells that are within a host animal.

Purification of antigen may be accomplished using art-recognized methods, some of which are described herein.

The purified antigen can be attached to a suitable matrix such as agarose beads, acrylamide beads, glass beads, cellulose, various acrylic copolymers, hydroxyl methacrylate gels, polyacrylic and polymethacrylic copolymers, nylon, neutral and ionic carriers, and the like, for use in the affinity chromatographic separation of phage display clones. Attachment of the antigen protein to the matrix can be accomplished by the methods described in *Methods in Enzymology*, vol. 44 (1976). A commonly employed technique for attaching protein ligands to polysaccharide matrices, e.g. agarose, dextran or cellulose, involves activation of the carrier with cyanogen halides and subsequent coupling of the peptide ligand's primary aliphatic or aromatic amines to the activated matrix.

Alternatively, antigen can be used to coat the wells of adsorption plates, expressed on host cells affixed to adsorption plates or used in cell sorting, or conjugated to biotin for capture with streptavidin-coated beads, or used in any other art-known method for panning phage display libraries.

The phage library samples are contacted with immobilized antigen under conditions suitable for binding of at least a portion of the phage particles with the adsorbent. Normally, the conditions, including pH, ionic strength, temperature and the like are selected to mimic physiological conditions. The phages bound to the solid phase are washed and then eluted by acid, e.g. as described in Barbas et al., *Proc. Natl. Acad. Sci USA*, 88: 7978-7982 (1991), or by alkali, e.g. as described in Marks et al., *J. Mol. Biol.*, 222: 581-597 (1991), or by antigen antigen competition, e.g. in a procedure similar to the antigen competition method of Clackson et al., *Nature*, 352: 624-628 (1991). Phages can be enriched 20-1,000-fold in a single round of selection. Moreover, the enriched phages can be grown in bacterial culture and subjected to further rounds of selection.

The efficiency of selection depends on many factors, including the kinetics of dissociation during washing, and whether multiple antibody fragments on a single phage can simultaneously engage with antigen. Antibodies with fast dissociation kinetics (and weak binding affinities) can be retained by use of short washes, multivalent phage display and high coating density of antigen in solid phase. The high density not only stabilizes the phage through multivalent interactions, but favors rebinding of phage that has dissociated. The selection of antibodies with slow dissociation kinetics (and good binding affinities) can be promoted by use of long washes and monovalent phage display as described in Bass et al., *Proteins*, 8: 309-314 (1990) and in WO 92/09690, and a low coating density of antigen as described in Marks et al., *Biotechnol.*, 10: 779-783 (1992).

It is possible to select between phage antibodies of different affinities, even with affinities that differ slightly, for antigen. However, random mutation of a selected antibody (e.g. as performed in some of the affinity maturation techniques described above) is likely to give rise to many mutants, most binding to antigen, and a few with higher affinity. With limiting antigen, rare high affinity phage could be competed out. To retain all the higher affinity mutants, phages can be incubated with excess biotinylated antigen, but with the biotinylated antigen at a concentration of lower molarity than the target molar affinity constant for antigen. The high affinity-binding phages can then be captured by streptavidin-coated paramagnetic beads. Such "equilibrium capture" allows the antibodies to be selected according to their affinities of binding, with sensitivity that permits isolation of mutant clones with as little as two-fold higher affinity from a great excess of phages with lower affinity. Conditions used in washing phages bound to a solid phase can also be manipulated to discriminate on the basis of dissociation kinetics.

Antigen clones may be activity selected. Fv clones corresponding to such antigen antibodies can be selected by (1) isolating antigen clones from a phage library as described above, and optionally amplifying the isolated population of phage clones by growing up the population in a suitable bacterial host; (2) selecting antigen and a second protein against which blocking and non-blocking activity, respectively, is desired; (3) adsorbing the antigen binding phage clones to immobilized antigen; (4) using an excess of the second protein to elute any undesired clones that recognize antigen-binding determinants which overlap or are shared with the binding determinants of the second protein; and (5) eluting the clones which remain adsorbed following step (4). Optionally, clones with the desired blocking/non-blocking properties can be further enriched by repeating the selection procedures described herein one or more times.

DNA encoding the hybridoma-derived monoclonal antibodies or phage display Fv clones of the invention is readily isolated and sequenced using conventional procedures (e.g., by using oligonucleotide primers designed to specifically amplify the heavy and light chain coding regions of interest from hybridoma or phage DNA template). Once isolated, the DNA can be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of the desired monoclonal antibodies in the recombinant host cells. Review articles on recombinant expression in bacteria of antibody-encoding DNA include Skerra et al., *Curr. Opinion in Immunol.*, 5: 256 (1993) and Pluckthun, *Immunol. Revs*, 130:151 (1992).

DNA encoding the Fv clones of the invention can be combined with known DNA sequences encoding heavy chain and/or light chain constant regions (e.g., the appropriate DNA sequences can be obtained from Kabat et al., supra) to form clones encoding full or partial length heavy and/or light chains. It will be appreciated that constant regions of any isotype can be used for this purpose, including IgG, IgM, IgA, IgD, and IgE constant regions, and that such constant regions can be obtained from any human or animal species. A Fv clone derived from the variable domain DNA of one animal (such as human) species and then fused to constant region DNA of another animal species to form coding sequence(s) for "hybrid," full length heavy chain and/or light chain is included in the definition of "chimeric" and "hybrid" antibody as used herein. In a preferred embodiment, a Fv clone derived from human variable DNA is fused to human constant region DNA to form coding sequence(s) for all human, full or partial length heavy and/or light chains.

DNA encoding antibody derived from a hybridoma of the invention can also be modified, for example, by substituting the coding sequence for human heavy- and light-chain constant domains in place of homologous murine sequences derived from the hybridoma clone (e.g., as in the method of Morrison et al., *Proc. Natl. Acad. Sci. USA*, 81:6851-6855 (1984)). DNA encoding a hybridoma or Fv clone-derived antibody or fragment can be further modified by covalently joining to the immunoglobulin coding sequence all or part of the coding sequence for a non-immunoglobulin polypeptide. In this manner, "chimeric" or "hybrid" antibodies are prepared that have the binding specificity of the Fv clone or hybridoma clone-derived antibodies of the invention.

Antigen Specificity

The present invention is applicable to antibodies of any appropriate antigen binding specificity. Preferably, the antibodies of the invention are specific to antigens that are biologically important polypeptides. More preferably, the antibodies of the invention are useful for therapy or diagnosis of diseases or disorders in a mammal. Non-limiting examples of therapeutic antibodies include anti-VEGF, anti-c-met, anti-IgE, anti-CD11, anti-CD18, anti-CD40, anti-tissue factor (TF), anti-HER2, and anti-TrkC antibodies. Antibodies directed against non-polypeptide antigens (such as tumor-associated glycolipid antigens) are also contemplated.

Where the antigen is a polypeptide, it may be a transmembrane molecule (e.g. receptor, such as a receptor tyrosine kinase) or a ligand such as a growth factor. Exemplary antigens include molecules such as renin; a growth hormone, including human growth hormone and bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor VIIIC, factor IX, tissue factor (TF), and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); a serum albumin such as human serum albumin; Muellerian-inhibiting substance; relaxin A-chain; relaxin B-chain; prorelaxin; mouse gonadotropin-associated peptide; a microbial protein, such as beta-lactamase; DNase; IgE; a cytotoxic T-lymphocyte associated antigen (CTLA), such as CTLA-4; inhibin; activin; vascular endothelial growth factor (VEGF); receptors for hormones or growth factors; protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-13; platelet-derived growth factor (PDGF); fibroblast growth factor such as aFGF and bFGF; epidermal growth factor (EGF); transforming growth factor (TGF) such as TGF-alpha and TGF-beta, including TGF-$\beta$1, TGF-$\beta$2, TGF-$\beta$3, TGF-$\beta$4, or TGF-$\beta$5; insulin-like growth factor-I and -II (IGF-I and IGF-II); des(1-3)-IGF-I (brain IGF-I), insulin-like growth factor binding proteins; CD proteins such as CD3, CD4, CD8, CD19, CD20 and CD40; erythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the AIDS envelope; transport proteins; homing receptors; addressins; regulatory proteins; integrins such as CD11a, CD11b, CD11c, CD18, an ICAM, VLA-4 and VCAM; a tumor associated antigen such as HER2, HER3 or HER4 receptor; and fragments of any of the above-listed polypeptides.

Exemplary antigens for antibodies encompassed by the present invention include CD proteins such as CD3, CD4, CD8, CD19, CD20, CD34, and CD46; members of the ErbB receptor family such as the EGF receptor, HER2, HER3 or HER4 receptor; cell adhesion molecules such as LFA-1, Mac1, p150.95, VLA-4, ICAM-1, VCAM, $\alpha4/\beta7$ integrin, and $\alpha v/\beta3$ integrin including either $\alpha$ or $\beta$ subunits thereof (e.g. anti-CD11a, anti-CD18 or anti-CD11b antibodies); growth factors such as VEGF; tissue factor (TF); TGF-$\beta$ alpha interferon ($\alpha$-IFN); an interleukin, such as IL-8; IgE; blood group antigens Apo2, death receptor; flk2/flt3 receptor; obesity (OB) receptor; mpl receptor; CTLA-4; protein C etc. In some embodiments, the antibody of the invention binds (in some embodiments, specifically binds) c-met.

Antibody Fragments

The present invention encompasses antibody fragments. In certain circumstances there are advantages of using antibody fragments, rather than whole antibodies. The smaller size of the fragments allows for rapid clearance, and may lead to improved access to solid tumors.

Various techniques have been developed for the production of antibody fragments. Traditionally, these fragments were derived via proteolytic digestion of intact antibodies (see, e.g., Morimoto et al., Journal of Biochemical and Biophysical Methods 24:107-117 (1992); and Brennan et al., Science, 229:81 (1985)). However, these fragments can now be produced directly by recombinant host cells. Fab, Fv and ScFv antibody fragments can all be expressed in and secreted from *E. coli*, thus allowing the facile production of large amounts of these fragments. Antibody fragments can be isolated from the antibody phage libraries discussed above. Alternatively, Fab'-SH fragments can be directly recovered from *E. coli* and chemically coupled to form F(ab')$_2$ fragments (Carter et al., Bio/Technology 10:163-167 (1992)). According to another approach, F(ab')$_2$ fragments can be isolated directly from recombinant host cell culture. Fab and F(ab')$_2$ fragment with increased in vivo half-life comprising a salvage receptor binding epitope residues are described in U.S. Pat. No. 5,869,046. Other techniques for the production of antibody fragments will be apparent to the skilled practitioner. In other embodiments, the antibody of choice is a single chain Fv fragment (scFv) (see, e.g., WO 93/16185; U.S. Pat. Nos. 5,571,894 and 5,587,458). Fv and sFv are the only species with intact combining sites that are devoid of constant regions; thus, they are suitable for reduced nonspecific binding during in vivo use. sFv fusion proteins may be constructed to yield fusion of an effector protein at either the amino or the carboxy terminus of an sFv. See Antibody Engineering, ed. Borrebaeck, supra. The antibody fragment may also be a "linear antibody," e.g., as described, for example, in U.S. Pat. No. 5,641,870. Such linear antibody fragments may be monospecific or bispecific.

Accordingly, in some embodiment, the anti-c-met antibody is a one-armed antibody (i.e., the heavy chain variable domain and the light chain variable domain form a single antigen binding arm) comprising an Fc region, wherein the Fc region comprises a first and a second Fc polypeptide, wherein the first and second Fc polypeptides are present in a complex and form a Fc region that increases stability of said antibody fragment compared to a Fab molecule comprising said antigen binding arm. One armed antibodies are further described herein.

Humanized Antibodies

The present invention encompasses humanized antibodies. Various methods for humanizing non-human antibodies are known in the art. For example, a humanized antibody can have one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al. (1986) Nature 321:522-525; Riechmann et al. (1988) Nature 332:323-327; Verhoeyen et al. (1988) Science 239:1534-1536), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework for the humanized antibody (Sims et al. (1993) J. Immunol. 151:2296; Chothia et al. (1987) J. Mol. Biol. 196:901. Another method uses a particular framework derived from the consensus sequence of all human antibodies of a particular subgroup of light or heavy chains. The same framework may be used for several different humanized antibodies (Carter et al. (1992) Proc. Natl. Acad. Sci. USA, 89:4285; Presta et al. (1993) J. Immunol., 151:2623.

It is further important that antibodies be humanized with retention of high affinity for the antigen and other favorable biological properties. To achieve this goal, according to one method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Human Antibodies

Human antibodies of the invention can be constructed by combining Fv clone variable domain sequence(s) selected from human-derived phage display libraries with known human constant domain sequences(s) as described above. Alternatively, human monoclonal antibodies of the invention can be made by the hybridoma method. Human myeloma and mouse-human heteromyeloma cell lines for the production of human monoclonal antibodies have been described, for example, by Kozbor J. Immunol., 133:3001 (1984); Brodeur et al., Monoclonal Antibody Production Techniques and Applications, pp. 51-63 (Marcel Dekker, Inc., New York, 1987); and Boerner et al., J. Immunol., 147:86 (1991).

It is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region (JH) gene in chimeric and germline mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., Proc. Natl. Acad. Sci USA, 90: 2551 (1993); Jakobovits et al., Nature, 362: 255 (1993); Bruggermann et al., Year in Immunol., 7:33 (1993).

Gene shuffling can also be used to derive human antibodies from non-human, e.g., rodent, antibodies, where the human antibody has similar affinities and specificities to the starting non-human antibody. According to this method, which is also called "epitope imprinting," either the heavy or light chain variable region of a non-human antibody fragment obtained by phage display techniques as described above is replaced with a repertoire of human V domain genes, creating a population of non-human chain/human chain scFv or Fab chimeras. Selection with antigen results in isolation of a non-human chain/human chain chimeric scFv or Fab wherein the human chain restores the antigen binding site destroyed upon removal of the corresponding non-human chain in the primary phage display clone, i.e. the epitope governs (imprints) the choice of the human chain partner. When the process is repeated in order to replace the remaining non-human chain, a human antibody is obtained (see PCT WO 93/06213 published Apr. 1, 1993). Unlike traditional humanization of non-human antibodies by CDR grafting, this technique provides completely human antibodies, which have no FR or CDR residues of non-human origin.

Bispecific Antibodies

Bispecific antibodies are monoclonal, preferably human or humanized, antibodies that have binding specificities for at least two different antigens. In the present case, one of the binding specificities is for antigen and the other is for any other antigen. Exemplary bispecific antibodies may bind to two different epitopes of the antigen. Bispecific antibodies may also be used to localize cytotoxic agents to cells which express antigen. These antibodies possess a antigen-binding arm and an arm which binds the cytotoxic agent (e.g., saporin, anti-interferon-α, vinca alkaloid, ricin A chain, methotrexate or radioactive isotope hapten). Bispecific antibodies can be prepared as full length antibodies or antibody fragments (e.g., $F(ab')_2$ bispecific antibodies).

Methods for making bispecific antibodies are known in the art. Traditionally, the recombinant production of bispecific antibodies is based on the co-expression of two immunoglobulin heavy chain-light chain pairs, where the two heavy chains have different specificities (Milstein and Cuello, Nature, 305: 537 (1983)). Because of the random assortment of immunoglobulin heavy and light chains, these hybridomas (quadromas) produce a potential mixture of 10 different antibody molecules, of which only one has the correct bispecific structure. The purification of the correct molecule, which is usually done by affinity chromatography steps, is rather cumbersome, and the product yields are low. Similar procedures are disclosed in WO 93/08829 published May 13, 1993, and in Traunecker et al., *EMBO J.,* 10: 3655 (1991).

According to a different and more preferred approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CH1), containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., *Methods in Enzymology,* 121:210 (1986).

According to another approach, the interface between a pair of antibody molecules can be engineered to maximize the percentage of heterodimers which are recovered from recombinant cell culture. The preferred interface comprises at least a part of the $C_H3$ domain of an antibody constant domain. In this method, one or more small amino acid side chains from the interface of the first antibody molecule are replaced with larger side chains (e.g., tyrosine or tryptophan) (knobs or protuberances). Compensatory "cavities" (holes) of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers. Knobs and holes are further described herein.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/00373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science,* 229: 81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli,* which can be chemically coupled to form bispecific antibodies. Shalaby et al., *J. Exp. Med.,* 175: 217-225 (1992) describe the production of a fully humanized bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells overexpressing the HER2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., *J. Immunol.,* 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA,* 90:6444-6448 (1993) has provided an alternative mechanism for making bispecific antibody fragments. The fragments comprise a heavy-chain variable domain (VH) connected to a light-chain variable domain (VL) by a linker which is too short to allow pairing between the two domains on the same chain. Accordingly, the VH and VL domains of one fragment are forced to pair with the complementary VL and VH domains of another fragment, thereby forming two antigen-binding sites. Another strategy for making bispecific antibody fragments by the use of single-chain Fv (sFv) dimers has also been reported. See Gruber et al., *J. Immunol.,* 152:5368 (1994).

Antibodies with more than two valencies are contemplated. For example, trispecific antibodies can be prepared. Tutt et al. *J. Immunol.* 147: 60 (1991).

Multivalent Antibodies

A multivalent antibody may be internalized (and/or catabolized) faster than a bivalent antibody by a cell expressing an antigen to which the antibodies bind. The antibodies of the present invention can be multivalent antibodies (which are other than of the IgM class) with three or more antigen binding sites (e.g. tetravalent antibodies), which can be readily produced by recombinant expression of nucleic acid encoding the polypeptide chains of the antibody. The multivalent antibody can comprise a dimerization domain and three or more antigen binding sites. The preferred dimerization domain comprises (or consists of) an Fc region or a hinge region. In this scenario, the antibody will comprise an Fc region and three or more antigen binding sites amino-terminal to the Fe region. The preferred multivalent antibody herein comprises (or consists of) three to about eight, but preferably four, antigen binding sites. The multivalent antibody comprises at least one polypeptide chain (and preferably two polypeptide chains), wherein the polypeptide chain(s) comprise two or more variable domains. For instance, the polypeptide chain(s) may comprise VD1-(X1)n-VD2-(X2)n-Fc, wherein VD1 is a first variable domain, VD2 is a second variable domain, Fc is one polypeptide chain of an Fc region, X1 and X2 represent an amino acid or polypeptide, and n is 0 or 1. For instance, the polypeptide chain(s) may comprise: VH-CH1-flexible linker-VH-CH1-Fc region chain; or VH-CH1-VH-CH1-Fc region chain. The multivalent antibody herein preferably further comprises at least two (and preferably four) light chain variable domain polypeptides. The multivalent antibody herein may, for instance, comprise from about two to about eight light chain variable domain polypeptides. The light chain variable domain polypeptides contemplated here comprise a light chain variable domain and, optionally, further comprise a CL domain.

Antibody Variants

In some embodiments, amino acid sequence modification(s) of the antibodies described herein are contemplated. For example, it may be desirable to improve the binding affinity and/or other biological properties of the antibody. Amino acid sequence variants of the antibody are prepared by introducing appropriate nucleotide changes into the antibody nucleic acid, or by peptide synthesis. Such modifications include, for example, deletions from, and/or insertions into and/or substitutions of, residues within the amino acid sequences of the antibody. Any combination of deletion, insertion, and substitution is made to arrive at the final construct, provided that the final construct possesses the desired characteristics. The amino acid alterations may be introduced in the subject antibody amino acid sequence at the time that sequence is made.

A useful method for identification of certain residues or regions of the antibody that are preferred locations for mutagenesis is called "alanine scanning mutagenesis" as described by Cunningham and Wells (1989) *Science,* 244: 1081-1085. Here, a residue or group of target residues are identified (e.g., charged residues such as arg, asp, his, lys, and glu) and replaced by a neutral or negatively charged amino acid (most preferably alanine or polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed immunoglobulins are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to a cytotoxic polypeptide. Other insertional variants of the antibody molecule include the fusion to the N- or C-terminus of the antibody to an enzyme (e.g., for ADEPT) or a polypeptide which increases the serum half-life of the antibody.

Glycosylation of polypeptides is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Where the antibody comprises an Fc region, the carbohydrate attached thereto may be altered. For example, antibodies with a mature carbohydrate structure that lacks fucose attached to an Fc region of the antibody are described in US Pat Appl No US 2003/0157108 (Presta, L.). See also US 2004/0093621 (Kyowa Hakko Kogyo Co., Ltd). Antibodies with a bisecting N-acetylglucosamine (GlcNAc) in the carbohydrate attached to an Fc region of the antibody are referenced in WO 2003/011878, Jean-Mairet et al. and U.S. Pat. No. 6,602,684, Umana et al. Antibodies with at least one galactose residue in the oligosaccharide attached to an Fc region of the antibody are reported in WO 1997/30087, Patel et al. See, also, WO 1998/58964 (Raju, S.) and WO 1999/22764 (Raju, S.) concerning antibodies with altered carbohydrate attached to the Fc region thereof. See also US 2005/0123546 (Umana et al.) on antigen-binding molecules with modified glycosylation.

The preferred glycosylation variant herein comprises an Fc region, wherein a carbohydrate structure attached to the Fc region lacks fucose. Such variants have improved ADCC function. Optionally, the Fc region further comprises one or more amino acid substitutions therein which further improve ADCC, for example, substitutions at positions 298, 333, and/or 334 of the Fc region (Eu numbering of residues). Examples of publications related to "defucosylated" or "fucose-deficient" antibodies include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; Okazaki et al. *J. Mol. Biol.* 336:1239-1249 (2004); Yamane-Ohnuki et al. *Biotech. Bioeng.* 87: 614 (2004). Examples of cell lines producing defucosylated antibodies include Lec13 CHO cells deficient in protein fucosylation (Ripka et al. *Arch. Biochem. Biophys.* 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (Yamane-Ohnuki et al. *Biotech. Bioeng.* 87: 614 (2004)).

In one aspect, the invention provides an antibody fragment comprising at least one characteristic that promotes heterodimerization, while minimizing homodimerization, of the Fc sequences within the antibody fragment. Such characteristic(s) improves yield and/or purity and/or homogeneity of the immunoglobulin populations obtainable by methods of the invention as described herein. In one embodiment, a first Fc polypeptide and a second Fc polypeptide meet/interact at an interface. In some embodiments wherein the first and second Fc polypeptides meet at an interface, the interface of the second Fc polypeptide (sequence) comprises a protuberance (also termed a "knob") which is positionable in a cavity (also termed a "hole") in the interface of the first Fc polypeptide (sequence). In one embodiment, the first Fc polypeptide has been altered from a template/original polypeptide to encode the cavity or the second Fc polypeptide has been altered from a template/original polypeptide to encode the protuberance, or both. In one embodiment, the first Fc polypeptide has been altered from a template/original polypeptide to encode the cavity and the second Fc polypeptide has been altered from a template/original polypeptide to encode the protuberance. In one embodiment, the interface of the second Fc polypeptide comprises a protuberance which is positionable in a cavity in the interface of the first Fc polypeptide, wherein the cavity or protuberance, or both, have been introduced into the interface of the first and second Fc polypeptides, respectively. In some embodiments wherein the first and second Fc polypeptides meet at an interface, the interface of the first Fc polypeptide (sequence) comprises a protuberance which is positionable in a cavity in the interface of the second Fc polypeptide (sequence). In one embodiment, the second Fc polypeptide has been altered from a template/original polypeptide to encode the cavity or the first Fc polypeptide has been altered from a template/original polypeptide to encode the protuberance, or both. In one embodiment, the second Fc polypeptide has been altered from a template/original polypeptide to encode the cavity and the first Fc polypeptide has been altered from a template/original polypeptide to encode the protuberance. In one embodiment, the interface of the first Fc polypeptide comprises a protuberance which is positionable in a cavity in the interface of the second Fc polypeptide, wherein the protuberance or cavity, or both, have been introduced into the interface of the first and second Fc polypeptides, respectively.

In one embodiment, the protuberance and cavity each comprise a naturally occurring amino acid residue. In one embodiment, the Fc polypeptide comprising the protuberance is generated by replacing an original residue from the interface of a template/original polypeptide with an import residue having a larger side chain volume than the original residue. In one embodiment, the Fc polypeptide comprising the protuberance is generated by a method comprising a step wherein polynucleotide encoding an original residue from the interface of said polypeptide is replaced with polynucleotide encoding an import residue having a larger side chain volume than the original. In one embodiment, the original residue is threonine. In one embodiment, the original residue is T366. In one embodiment, the import residue is arginine (R). In one embodiment, the import residue is phenylalanine (F). In one embodiment, the import residue is tyrosine (Y). In one embodiment, the import residue is tryptophan (W). In one embodiment, the import residue is R, F, Y or W. In one embodiment, a protuberance is generated by replacing two or more residues in a template/original polypeptide. In one embodiment, the Fc polypeptide comprising a protuberance comprises replacement of threonine at position 366 with tryptophan, amino acid numbering according to the EU numbering scheme of Kabat et al. (pp. 688-696 in Sequences of proteins of immunological interest, 5th ed., Vol. 1 (1991; NIH, Bethesda, Md.)).

In some embodiments, the Fc polypeptide comprising a cavity is generated by replacing an original residue in the interface of a template/original polypeptide with an import residue having a smaller side chain volume than the original residue. For example, the Fc polypeptide comprising the cavity may be generated by a method comprising a step wherein polynucleotide encoding an original residue from the interface of said polypeptide is replaced with polynucleotide encoding an import residue having a smaller side chain volume than the original. In one embodiment, the original residue is threonine. In one embodiment, the original residue is leucine. In one embodiment, the original residue is tyrosine. In one embodiment, the import residue is not cysteine (C). In one embodiment, the import residue is alanine (A). In one embodiment, the import residue is serine (S). In one embodiment, the import residue is threonine (T). In one embodiment, the import residue is valine (V). A cavity can be generated by replacing one or more original residues of a template/original polypeptide. For example, in one embodiment, the Fc polypeptide comprising a cavity comprises replacement of two or more original amino acids selected from the group consisting of threonine, leucine and tyrosine. In one embodiment, the Fc polypeptide comprising a cavity comprises two or more import residues selected from the group consisting of alanine, serine, threonine and valine. In some embodiments, the Fc polypeptide comprising a cavity comprises replacement of two or more original amino acids selected from the group consisting of threonine, leucine and tyrosine, and wherein said original amino acids are replaced with import residues selected from the group consisting of alanine, serine, threonine and valine. In some embodiments, an original amino acid that is replaced is T366, L368 and/or Y407. In one embodiment, the Fc polypeptide comprising a cavity comprises replacement of threonine at position 366 with serine, amino acid numbering according to the EU numbering scheme of Kabat et al. supra. In one embodiment, the Fc polypeptide comprising a cavity comprises replacement of leucine at position 368 with alanine, amino acid numbering according to the EU numbering scheme of Kabat et al. supra. In one embodiment, the Fc polypeptide comprising a cavity comprises replacement of tyrosine at position 407 with valine, amino acid numbering according to the EU numbering scheme of Kabat et al. supra. In one embodiment, the Fc polypeptide comprising a cavity comprises two or more amino acid replacements selected from the group consisting of T366S, L368A and Y407V, amino acid numbering according to the EU numbering scheme of Kabat et al. supra. In some embodiments of these antibody fragments, the Fc polypeptide comprising the protuberance comprises replacement of threonine at position 366 with tryptophan, amino acid numbering according to the EU numbering scheme of Kabat et al. supra.

In one embodiment, the antibody comprises Fc mutations constituting "knobs" and "holes" as described in WO2005/063816. For example, a hole mutation can be one or more of T366A, L368A and/or Y407V in an Fc polypeptide, and a knob mutation can be T366W.

Another type of variant is an amino acid substitution variant. These variants have at least one amino acid (at least two, at least three, at least 4 or more) residue in the antibody molecule replaced by a different residue. The sites of greatest interest for substitutional mutagenesis include the hypervariable regions, but FR alterations are also contemplated. Conservative substitutions are shown in Table A under the heading of "preferred substitutions." If such substitutions result in a change in biological activity, then more substantial changes, denominated "exemplary substitutions" in Table A, or as further described below in reference to amino acid classes, may be introduced and the products screened.

TABLE A

| Original Residue | Exemplary Substitutions | Preferred Substitutions |
| --- | --- | --- |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:
  (1) hydrophobic: norleucine, met, ala, val, leu, ile;
  (2) neutral hydrophilic: Cys, Ser, Thr, Asn, Gln;
  (3) acidic: asp, glu;
  (4) basic: his, lys, arg;
  (5) residues that influence chain orientation: gly, pro; and
  (6) aromatic: trp, tyr, phe.
Non-conservative substitutions will entail exchanging a member of one of these classes for another class.

One type of substitutional variant involves substituting one or more hypervariable region residues of a parent antibody (e.g., a humanized or human antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g., 6-7 sites) are mutated to generate all possible amino acid substitutions at each site. The antibodies thus generated are displayed from filamentous phage particles as fusions to the gene III product of M13 packaged within each particle. The phage-displayed variants are then screened for their biological activity (e.g., binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and antigen. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Nucleic acid molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody.

It may be desirable to introduce one or more amino acid modifications in an Fc region of the immunoglobulin polypeptides of the invention, thereby generating a Fc region variant. The Fc region variant may comprise a human Fc region sequence (e.g., a human IgG1, IgG2, IgG3 or IgG4 Fc region) comprising an amino acid modification (e.g., a substitution) at one or more amino acid positions including that of a hinge cysteine.

In accordance with this description and the teachings of the art, it is contemplated that in some embodiments, an antibody used in methods of the invention may comprise one or more alterations as compared to the wild type counterpart antibody, e.g., in the Fc region. These antibodies would nonetheless retain substantially the same characteristics required for therapeutic utility as compared to their wild type counterpart. For example, it is thought that certain alterations can be made in the Fc region that would result in altered (i.e., either improved or diminished) C1q binding and/or Complement Dependent Cytotoxicity (CDC), e.g., as described in WO99/51642. See also Duncan & Winter Nature 322:738-40 (1988); U.S. Pat. Nos. 5,648,260; 5,624,821; and WO94/29351 concerning other examples of Fc region variants. WO00/42072 (Presta) and WO 2004/056312 (Lowman) describe antibody variants with improved or diminished binding to FcRs. The content of these patent publications are specifically incorporated herein by reference. See, also, Shields et al. J. Biol. Chem. 9(2): 6591-6604 (2001). Antibodies with increased half lives and improved binding to the neonatal Fc receptor (FcRn), which is responsible for the transfer of maternal IgGs to the fetus (Guyer et al., J. Immunol. 117:587 (1976) and Kim et al., J. Immunol. 24:249 (1994)), are described in US2005/0014934A1 (Hinton et al.). These antibodies comprise an Fc region with one or more substitutions therein which improve binding of the Fc region to FcRn. Polypeptide variants with altered Fc region amino acid sequences and increased or decreased C1q binding capability are described in U.S. Pat. No. 6,194,551B1, WO99/51642. The contents of those patent publications are specifically incorporated herein by reference. See, also, Idusogie et al., J. Immunol. 164: 4178-4184 (2000).

Antibody Derivatives

The antibodies of the present invention can be further modified to contain additional nonproteinaceous moieties that are known in the art and readily available. Preferably, the moieties suitable for derivatization of the antibody are water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymers are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

Screening for Antibodies with Desired Properties

The antibodies of the present invention can be characterized for their physical/chemical properties and biological functions by various assays known in the art (some of which are disclosed herein). For example, the antibodies can be further characterized by a series of assays including, but not limited to, N-terminal sequencing, amino acid analysis, non-denaturing size exclusion high pressure liquid chromatography (HPLC), mass spectrometry, ion exchange chromatography and papain digestion.

In certain embodiments of the invention, the antibodies produced herein are analyzed for their biological activity. In some embodiments, the antibodies of the present invention are tested for their antigen binding activity. The antigen binding assays that are known in the art and can be used herein include without limitation any direct or competitive binding assays using techniques such as western blots, radioimmunoassays, ELISA (enzyme linked immunosorbent assay), "sandwich" immunoassays, immunoprecipitation assays, fluorescent immunoassays, and protein A immunoassays. Illustrative assays are provided below in the Examples section.

Vectors, Host Cells, and Recombinant Methods

For recombinant production of a heterologous polypeptide (e.g, an antibody), the nucleic acid encoding it is isolated and inserted into a replicable vector for further cloning (amplification of the DNA) or for expression. DNA encoding the polypeptide (eg, antibody) is readily isolated and sequenced using conventional procedures (e.g., by using oligonucleotide probes that are capable of binding specifically to genes encoding the heavy and light chains of the antibody). Many vectors are available. The choice of vector depends in part on the host cell to be used. Generally, preferred host cells are of either prokaryotic origin. It will be appreciated that constant regions of any isotype can be used for this purpose, including IgG, IgM, IgA, IgD, and IgE constant regions, and that such constant regions can be obtained from any human or animal species.

a. Generating Antibodies Using Prokaryotic Host Cells:
  i. Vector Construction

Polynucleotide sequences encoding polypeptide components of the polypeptide (e.g., antibody) of the invention can be obtained using standard recombinant techniques. Desired polynucleotide sequences may be isolated and sequenced from antibody producing cells such as hybridoma cells. Alternatively, polynucleotides can be synthesized using nucleotide synthesizer or PCR techniques. Once obtained, sequences encoding the polypeptides are inserted into a recombinant vector capable of replicating and expressing heterologous polynucleotides in prokaryotic hosts. Many vectors that are available and known in the art can be used for the purpose of the present invention. Selection of an appropriate vector will depend mainly on the size of the nucleic acids to be inserted into the vector and the particular host cell to be transformed with the vector. Each vector contains various components, depending on its function (amplification or expression of heterologous polynucleotide, or both) and its compatibility with the particular host cell in which it resides. The vector components generally include, but are not limited to: an origin of replication, a selection marker gene, a promoter, a ribosome binding site (RBS), a signal sequence, the heterologous nucleic acid insert and a transcription termination sequence.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, *E. coli* is typically transformed using pBR322, a plasmid derived from an *E. coli* species. pBR322 contains genes encoding ampicillin (Amp) and tetracycline (Tet) resistance and thus provides easy means for identifying transformed cells. pBR322, its derivatives, or other microbial plasmids or bacteriophage may also contain, or be modified to contain, promoters which can be used by the microbial organism for expression of endogenous proteins. Examples of pBR322 derivatives used for expression of particular antibodies are described in detail in Carter et al., U.S. Pat. No. 5,648,237.

In addition, phage vectors containing replicon and control sequences that are compatible with the host microorganism can be used as transforming vectors in connection with these hosts. For example, bacteriophage such as λGEM™-11 may be utilized in making a recombinant vector which can be used to transform susceptible host cells such as *E. coli* LE392.

The expression vector of the invention may comprise two or more promoter-cistron pairs, encoding each of the polypeptide components. A promoter is an untranslated regulatory sequence located upstream (5') to a cistron that modulates its expression. Prokaryotic promoters typically fall into two classes, inducible and constitutive. Inducible promoter is a promoter that initiates increased levels of transcription of the cistron under its control in response to changes in the culture condition, e.g., the presence or absence of a nutrient or a change in temperature.

A large number of promoters recognized by a variety of potential host cells are well known. The selected promoter can be operably linked to cistron DNA encoding the light or heavy chain by removing the promoter from the source DNA via restriction enzyme digestion and inserting the isolated promoter sequence into the vector of the invention. Both the native promoter sequence and many heterologous promoters may be used to direct amplification and/or expression of the target genes. In some embodiments, heterologous promoters are utilized, as they generally permit greater transcription and higher yields of expressed target gene as compared to the native target polypeptide promoter.

Promoters suitable for use with prokaryotic hosts include the PhoA promoter, the β-lactamase and lactose promoter systems, a tryptophan (trp) promoter system and hybrid promoters such as the tac or the trc promoter. However, other promoters that are functional in bacteria (such as other known bacterial or phage promoters) are suitable as well. Their nucleotide sequences have been published, thereby enabling a skilled worker operably to ligate them to cistrons encoding the target light and heavy chains (Siebenlist et al., (1980) Cell 20: 269) using linkers or adaptors to supply any required restriction sites.

In one aspect of the invention, each cistron within the recombinant vector comprises a secretion signal sequence component that directs translocation of the expressed polypeptides across a membrane. In general, the signal sequence may be a component of the vector, or it may be a part of the target polypeptide DNA that is inserted into the vector. The signal sequence selected for the purpose of this invention should be one that is recognized and processed (i.e., cleaved by a signal peptidase) by the host cell. For prokaryotic host cells that do not recognize and process the signal sequences native to the heterologous polypeptides, the signal sequence is substituted by a prokaryotic signal sequence selected, for example, from the signal polypeptides of the present invention. In addition, the vector may comprise a signal sequence selected from the group consisting of the alkaline phosphatase, penicillinase, Lpp, or heat-stable enterotoxin II (STII) leaders, LamB, PhoE, PelB, OmpA, and MBP.

In one aspect of the invention, one or more polynucleotides (e.g., expression vectors) collectively encode a one-armed antibody. In one embodiment, a single polynucleotide encodes (a) the light and heavy chain components of the one armed antibody, and (b) the Fc polypeptide. In one embodiment, a single polynucleotide encodes the light and heavy chain components of the one armed antibody, and a separate polynucleotide encodes the Fc polypeptide. In one embodiment, separate polynucleotides encode the light chain component of the one-armed antibody, the heavy chain component of the one-armed antibody and the Fc polypeptide, respectively. Production of a one-armed antibody is described in, for example, in WO2005063816.

Prokaryotic host cells suitable for expressing antibodies of the invention include Archaebacteria and Eubacteria, such as Gram-negative or Gram-positive organisms. Examples of useful bacteria include *Escherichia* (e.g., *E. coli*), Bacilli (e.g., *B. subtilis*), Enterobacteria, *Pseudomonas* species (e.g., *P. aeruginosa*), *Salmonella typhimurium, Serratia marcescans, Klebsiella, Proteus, Shigella, Rhizobia, Vitreoscilla*, or *Paracoccus*. In one embodiment, gram-negative cells are used. In one embodiment, *E. coli* cells are used as hosts for the invention. Examples of *E. coli* strains include strain W3110 (Bachmann, Cellular and Molecular Biology, vol. 2 (Washington, D.C.: American Society for Microbiology, 1987), pp. 1190-1219; ATCC Deposit No. 27,325) and derivatives thereof, including strain 33D3 having genotype W3110 ΔfhuA (ΔtonA) ptr3 lac Iq lacL8 Δomp TΔ(nmpc-fepE) degP41 kanR (U.S. Pat. No. 5,639,635) and strains 63C1 and 64B4. Other strains and derivatives thereof, such as *E. coli* 294 (ATCC 31,446), *E. coli* B, *E. coli*, 1776 (ATCC 31,537) and *E. coli* RV308 (ATCC 31,608) are also suitable. These examples are illustrative rather than limiting. Methods for constructing derivatives of any of the above-mentioned bacteria having defined genotypes are known in the art and described in, for example, Bass et al., Proteins, 8:309-314 (1990). It is generally necessary to select the appropriate bacteria taking into consideration replicability of the replicon in the cells of a bacterium. For example, *E. coli, Serratia*, or *Salmonella* species can be suitably used as the host when well known plasmids such as pBR322, pBR325, pACYC 177, or pKN410 are used to supply the replicon. Typically the host cell should secrete minimal amounts of proteolytic enzymes, and additional protease inhibitors may desirably be incorporated in the cell culture.

ii. Antibody Production

Host cells are transformed with the above-described expression vectors and cultured in conventional nutrient media modified as appropriate for inducing promoters, selecting transformants, or amplifying the genes encoding the desired sequences.

Transformation means introducing DNA into the prokaryotic host so that the DNA is replicable, either as an extra-chromosomal element or by chromosomal integrant. Depending on the host cell used, transformation is done using standard techniques appropriate to such cells. The calcium treatment employing calcium chloride is generally used for bacterial cells that contain substantial cell-wall barriers. Another method for transformation employs polyethylene glycol/DMSO. Yet another technique used is electroporation.

Prokaryotic cells used to produce the polypeptides of the invention are grown in media known in the art and suitable for culture of the selected host cells. Examples of suitable media include Luria broth (LB) plus necessary nutrient supplements. In some embodiments, the media also contains a selection agent, chosen based on the construction of the expression vector, to selectively permit growth of prokaryotic cells containing the expression vector. For example, ampicillin is added to media for growth of cells expressing ampicillin resistant gene.

Any necessary supplements besides carbon, nitrogen, and inorganic phosphate sources may also be included at appropriate concentrations introduced alone or as a mixture with another supplement or medium such as a complex nitrogen source. Optionally the culture medium may contain one or more reducing agents selected from the group consisting of glutathione, cysteine, cystamine, thioglycollate, dithioerythritol and dithiothreitol.

The prokaryotic host cells are cultured at suitable temperatures. For *E. coli* growth, for example, the preferred temperature ranges from about 20° C. to about 39° C., more preferably from about 25° C. to about 37° C., even more preferably at about 30° C. The pH of the medium may be any pH ranging from about 5 to about 9, depending mainly on the host organism. For *E. coli*, the pH is preferably from about 6.8 to about 7.4, and more preferably about 7.0.

If an inducible promoter is used in the expression vector of the invention, protein expression is induced under conditions suitable for the activation of the promoter. In one aspect of the invention, PhoA promoters are used for controlling transcription of the polypeptides. Accordingly, the transformed host cells are cultured in a phosphate-limiting medium for induction. Preferably, the phosphate-limiting medium is the C.R.A.P medium (see, e.g., Simmons et al., J. Immunol. Methods (2002), 263:133-147) or media described in WO2002/061090. A variety of other inducers may be used, according to the vector construct employed, as is known in the art.

In one embodiment, the expressed polypeptides of the present invention are secreted into and recovered from the periplasm of the host cells. Protein recovery typically involves disrupting the microorganism, generally by such means as osmotic shock, sonication or lysis. Once cells are disrupted, cell debris or whole cells may be removed by centrifugation or filtration. The proteins may be further purified, for example, by affinity resin chromatography. Alternatively, proteins can be transported into the culture media and isolated therein. Cells may be removed from the culture and the culture supernatant being filtered and concentrated for further purification of the proteins produced. The expressed polypeptides can be further isolated and identified using commonly known methods such as polyacrylamide gel electrophoresis (PAGE) and Western blot assay.

In one aspect of the invention, antibody production is conducted in large quantity by a fermentation process. Various large-scale fed-batch fermentation procedures are available for production of recombinant proteins. Large-scale fermentations have at least 1000 liters of capacity, preferably about 1,000 to 100,000 liters of capacity. These fermentors use agitator impellers to distribute oxygen and nutrients, especially glucose (the preferred carbon/energy source). Small scale fermentation refers generally to fermentation in a fermentor that is no more than approximately 100 liters in volumetric capacity, and can range from about 1 liter to about 100 liters.

In a fermentation process, induction of protein expression is typically initiated after the cells have been grown under suitable conditions to a desired density, e.g., an OD550 of about 180-220, at which stage the cells are in the early stationary phase. A variety of inducers may be used, according to the vector construct employed, as is known in the art and described above. Cells may be grown for shorter periods prior to induction. Cells are usually induced for about 12-50 hours, although longer or shorter induction time may be used.

To improve the production yield and quality of the polypeptides of the invention, various fermentation conditions can be modified. For example, to improve the proper assembly and folding of the secreted antibody polypeptides, additional vectors overexpressing chaperone proteins, such as Dsb proteins (DsbA, DsbB, DsbC, DsbD, and/or DsbG) or FkpA (a peptidylprolyl cis,trans-isomerase with chaperone activity) can be used to co-transform the host prokaryotic cells. The chaperone proteins have been demonstrated to facilitate the proper folding and solubility of heterologous proteins produced in bacterial host cells. Chen et al., (1999) J. Biol. Chem. 274:19601-19605; Georgiou et al., U.S. Pat. No. 6,083,715; Georgiou et al., U.S. Pat. No. 6,027,888; Bothmann and Pluckthun (2000) J. Biol. Chem. 275:17100-17105; Ramm and Pluckthun, (2000) J. Biol. Chem. 275: 17106-17113; Arie et al., (2001) Mol. Microbiol. 39:199-210. In some embodiments, DsbA and C are expressed in the bacterial host cell.

To minimize proteolysis of expressed heterologous proteins (especially those that are proteolytically sensitive), certain host strains deficient for proteolytic enzymes can be used for the present invention. For example, host cell strains may be modified to effect genetic mutation(s) in the genes encoding known bacterial proteases such as Protease III, OmpT, DegP, Tsp, Protease I, Protease Mi, Protease V, Protease VI, and combinations thereof. Some E. coli protease-deficient strains are available and described in, for example, Joly et al., (1998), supra; Georgiou et al., U.S. Pat. No. 5,264,365; Georgiou et al., U.S. Pat. No. 5,508,192; Hara et al., Microbial Drug Resistance, 2:63-72 (1996).

In one embodiment, E. coli strains deficient for proteolytic enzymes and transformed with plasmids overexpressing one or more chaperone proteins are used as host cells in the expression system of the invention.

iii. Antibody Purification

Standard protein purification methods known in the art can be employed. The following procedures are exemplary of suitable purification procedures: fractionation on immunoaffinity or ion-exchange columns, ethanol precipitation, reverse phase HPLC, chromatography on silica or on a cation-exchange resin such as DEAE, chromatofocusing, SDS-PAGE, ammonium sulfate precipitation, and gel filtration using, for example, Sephadex G-75.

In one aspect, Protein A immobilized on a solid phase is used for immunoaffinity purification of the antibody products of the invention. Protein A is a 41kD cell wall protein from Staphylococcus aureas which binds with a high affinity to the Fc region of antibodies. Lindmark et al., (1983) J. Immunol. Meth. 62:1-13. The solid phase to which Protein A is immobilized is preferably a column comprising a glass or silica surface, more preferably a controlled pore glass column or a silicic acid column. In some applications, the column has been coated with a reagent, such as glycerol, in an attempt to prevent nonspecific adherence of contaminants.

As the first step of purification, the preparation derived from the cell culture as described above is applied onto the Protein A immobilized solid phase to allow specific binding of the antibody of interest to Protein A. The solid phase is then washed to remove contaminants non-specifically bound to the solid phase. Finally the antibody of interest is recovered from the solid phase by elution.

Immunoconjugates

The invention also provides immunoconjugates (interchangeably termed "antibody-drug conjugates" or "ADC"), comprising any of the antibodies described herein conjugated to a cytotoxic agent such as a chemotherapeutic agent, a drug, a growth inhibitory agent, a toxin (e.g., an enzymatically active toxin of bacterial, fungal, plant, or animal origin, or fragments thereof), or a radioactive isotope (i.e., a radioconjugate).

The use of antibody-drug conjugates for the local delivery of cytotoxic or cytostatic agents, i.e., drugs to kill or inhibit tumor cells in the treatment of cancer (Syrigos and Epenetos (1999) Anticancer Research 19:605-614; Niculescu-Duvaz and Springer (1997) Adv. Drg. Del. Rev. 26:151-172; U.S. Pat. No. 4,975,278) allows targeted delivery of the drug moiety to tumors, and intracellular accumulation therein, where systemic administration of these unconjugated drug agents may result in unacceptable levels of toxicity to normal cells as well as the tumor cells sought to be eliminated (Baldwin et al., (1986) Lancet pp. (Mar. 15, 1986): 603-05; Thorpe, (1985) "Antibody Carriers Of Cytotoxic Agents In Cancer Therapy: A Review," in Monoclonal Antibodies '84: Biological And Clinical Applications, A. Pinchera et al. (ed.s), pp. 475-506). Maximal efficacy with minimal toxicity is sought thereby. Both polyclonal antibodies and monoclonal antibodies have been reported as useful in these strategies (Rowland et al., (1986) Cancer Immunol. Immunother., 21:183-87). Drugs used in these methods include daunomycin, doxorubicin, methotrexate, and vindesine (Rowland et al., (1986) supra). Toxins used in antibody-toxin conjugates include bacterial toxins such as diphtheria toxin, plant toxins such as ricin, small molecule toxins such as geldanamycin (Mandler et al (2000) Jour. of the Nat. Cancer Inst. 92(19):1573-1581; Mandler et al., (2000) Bioorganic & Med. Chem. Letters 10:1025-1028; Mandler et al., (2002) Bioconjugate Chem. 13:786-791), maytansinoids (EP 1391213; Liu et al., (1996) Proc. Natl. Acad. Sci. USA 93:8618-8623), and calicheamicin (Lode et al., (1998) Cancer Res. 58:2928; Hinman et al., (1993) Cancer Res. 53:3336-3342). The toxins may effect their cytotoxic and cytostatic effects by mechanisms including tubulin binding, DNA binding, or topoisomerase inhibition. Some cytotoxic drugs tend to be inactive or less active when conjugated to large antibodies or protein receptor ligands.

ZEVALIN® (ibritumomab tiuxetan, Biogen/Idec) is an antibody-radioisotope conjugate composed of a murine IgG1 kappa monoclonal antibody directed against the CD20 antigen found on the surface of normal and malignant B lymphocytes and $^{111}$In or $^{90}$Y radioisotope bound by a thiourea linker-chelator (Wiseman et al., (2000) Eur. Jour. Nucl. Med. 27(7):766-77; Wiseman et al., (2002) Blood 99(12):4336-42; Witzig et al., (2002) J. Clin. Oncol. 20(10): 2453-63; Witzig et al., (2002) J. Clin. Oncol. 20(15):3262-69). Although ZEVALIN has activity against B-cell non-Hodgkin's Lymphoma (NHL), administration results in severe and prolonged cytopenias in most patients. MYLO-TARG™ (gemtuzumab ozogamicin, Wyeth Pharmaceuticals), an antibody drug conjugate composed of a hu CD33 antibody linked to calicheamicin, was approved in 2000 for the treatment of acute myeloid leukemia by injection (Drugs of the Future (2000) 25(7):686; U.S. Pat. Nos. 4,970,198; 5,079,233; 5,585,089; 5,606,040; 5,6937,62; 5,739,116; 5,767,285; 5,773,001). Cantuzumab mertansine (Immunogen, Inc.), an antibody drug conjugate composed of the huC242 antibody linked via the disulfide linker SPP to the maytansinoid drug moiety, DM1, is advancing into Phase II trials for the treatment of cancers that express CanAg, such as colon, pancreatic, gastric, and others. MLN-2704 (Millennium Pharm., BZL Biologics, Immunogen Inc.), an antibody drug conjugate composed of the anti-prostate specific membrane antigen (PSMA) monoclonal antibody linked to the maytansinoid drug moiety, DM1, is under development for the potential treatment of prostate tumors. The auristatin peptides, auristatin E (AE) and monomethylauristatin (MMAE), synthetic analogs of dolastatin, were conjugated to chimeric monoclonal antibodies cBR96 (specific to Lewis Y on carcinomas) and cAC10 (specific to CD30 on hematological malignancies) (Doronina et al., (2003) Nature Biotechnology 21(7):778-784) and are under therapeutic development.

Chemotherapeutic agents useful in the generation of immunoconjugates are described herein (e.g., above). Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin, and the tricothecenes. See, e.g., WO 93/21232 published Oct. 28, 1993. A variety of radionuclides are available for the production of radioconjugated antibodies. Examples include $^{212}$Bi, $^{131}$I, $^{131}$In, $^{90}$Y, and $^{186}$Re. Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science, 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

Conjugates of an antibody and one or more small molecule toxins, such as a calicheamicin, maytansinoids, dolastatins, aurostatins, a trichothecene, and CC1065, and the derivatives of these toxins that have toxin activity, are also contemplated herein.

i. Maytansine and Maytansinoids

In some embodiments, the immunoconjugate comprises an antibody (full length or fragments) of the invention conjugated to one or more maytansinoid molecules.

Maytansinoids are mitototic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248, 870; 4,256,746; 4,260,608; 4,265,814; 4,294,757; 4,307, 016; 4,308,268; 4,308,269; 4,309,428; 4,313,946; 4,315, 929; 4,317,821; 4,322,348; 4,331,598; 4,361,650; 4,364, 866; 4,424,219; 4,450,254; 4,362,663; and 4,371,533.

Maytansinoid drug moieties are attractive drug moieties in antibody drug conjugates because they are: (i) relatively accessible to prepare by fermentation or chemical modification, derivatization of fermentation products, (ii) amenable to derivatization with functional groups suitable for conjugation through the non-disulfide linkers to antibodies, (iii) stable in plasma, and (iv) effective against a variety of tumor cell lines.

Immunoconjugates containing maytansinoids, methods of making same, and their therapeutic use are disclosed, for example, in U.S. Pat. Nos. 5,208,020, 5,416,064 and European Patent EP 0 425 235 B1, the disclosures of which are hereby expressly incorporated by reference. Liu et al., Proc. Natl. Acad. Sci. USA 93:8618-8623 (1996) described immunoconjugates comprising a maytansinoid designated DM1 linked to the monoclonal antibody C242 directed against human colorectal cancer. The conjugate was found to be highly cytotoxic towards cultured colon cancer cells, and showed antitumor activity in an in vivo tumor growth assay. Chari et al., Cancer Research 52:127-131 (1992) describe immunoconjugates in which a maytansinoid was conjugated via a disulfide linker to the murine antibody A7 binding to an antigen on human colon cancer cell lines, or to another murine monoclonal antibody TA.1 that binds the HER-2/neu oncogene. The cytotoxicity of the TA.1-maytansinoid conjugate was tested in vitro on the human breast cancer cell line SK-BR-3, which expresses $3 \times 10^5$ HER-2 surface antigens per cell. The drug conjugate achieved a degree of cytotoxicity similar to the free maytansinoid drug, which could be increased by increasing the number of maytansinoid molecules per antibody molecule. The A7-maytansinoid conjugate showed low systemic cytotoxicity in mice.

Antibody-maytansinoid conjugates are prepared by chemically linking an antibody to a maytansinoid molecule without significantly diminishing the biological activity of either the antibody or the maytansinoid molecule. See, e.g., U.S. Pat. No. 5,208,020 (the disclosure of which is hereby expressly incorporated by reference). An average of 3-4 maytansinoid molecules conjugated per antibody molecule has shown efficacy in enhancing cytotoxicity of target cells without negatively affecting the function or solubility of the antibody, although even one molecule of toxin/antibody would be expected to enhance cytotoxicity over the use of naked antibody. Maytansinoids are well known in the art and can be synthesized by known techniques or isolated from natural sources. Suitable maytansinoids are disclosed, for example, in U.S. Pat. No. 5,208,020 and in the other patents and nonpatent publications referred to hereinabove. Preferred maytansinoids are maytansinol and maytansinol analogues modified in the aromatic ring or at other positions of the maytansinol molecule, such as various maytansinol esters.

There are many linking groups known in the art for making antibody-maytansinoid conjugates, including, for example, those disclosed in U.S. Pat. No. 5,208,020 or EP Patent 0 425 235 B1, Chari et al., Cancer Research 52:127-131 (1992), and U.S. patent application Ser. No. 10/960,602, filed Oct. 8, 2004, the disclosures of which are hereby expressly incorporated by reference. Antibody-maytansinoid conjugates comprising the linker component SMCC may be prepared as disclosed in U.S. patent application Ser. No. 10/960,602, filed Oct. 8, 2004. The linking groups include disulfide groups, thioether groups, acid labile groups, photolabile groups, peptidase labile groups, or esterase labile groups, as disclosed in the above-identified patents, disulfide and thioether groups being preferred. Additional linking groups are described and exemplified herein.

Conjugates of the antibody and maytansinoid may be made using a variety of bifunctional protein coupling agents such as N-succinimidyl-3-(2-pyridyldithio) propionate (SPDP), succinimidyl-4-(N-maleimidomethyl)cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Particularly preferred coupling agents include N-succinimidyl-3-(2-pyridyldithio) propionate (SPDP) (Carlsson et al., Biochem. J. 173:723-737 (1978)) and N-succinimidyl-4-(2-pyridylthio)pentanoate (SPP) to provide for a disulfide linkage.

The linker may be attached to the maytansinoid molecule at various positions, depending on the type of the link. For example, an ester linkage may be formed by reaction with a hydroxyl group using conventional coupling techniques. The reaction may occur at the C-3 position having a hydroxyl group, the C-14 position modified with hydroxymethyl, the C-15 position modified with a hydroxyl group, and the C-20 position having a hydroxyl group. In a preferred embodiment, the linkage is formed at the C-3 position of maytansinol or a maytansinol analogue.

ii. Auristatins and Dolastatins

In some embodiments, the immunoconjugate comprises an antibody of the invention conjugated to dolastatins or dolostatin peptidic analogs and derivatives, the auristatins (U.S. Pat. Nos. 5,635,483 and 5,780,588). Dolastatins and auristatins have been shown to interfere with microtubule dynamics, GTP hydrolysis, and nuclear and cellular division (Woyke et al (2001) Antimicrob. Agents and Chemother. 45(12):3580-3584) and have anticancer (U.S. Pat. No. 5,663,149) and antifungal activity (Pettit et al., (1998) Antimicrob. Agents Chemother. 42:2961-2965). The dolastatin or auristatin drug moiety may be attached to the antibody through the N (amino) terminus or the C (carboxyl) terminus of the peptidic drug moiety (WO 02/088172).

Exemplary auristatin embodiments include the N-terminus linked monomethylauristatin drug moieties DE and DF, disclosed in "Monomethylvaline Compounds Capable of Conjugation to Ligands," U.S. Ser. No. 10/983,340, filed Nov. 5, 2004, the disclosure of which is expressly incorporated by reference in its entirety.

Typically, peptide-based drug moieties can be prepared by forming a peptide bond between two or more amino acids and/or peptide fragments. Such peptide bonds can be prepared, for example, according to the liquid phase synthesis method (see E. Schröder and K. Lübke, "The Peptides," volume 1, pp. 76-136, 1965, Academic Press) that is well known in the field of peptide chemistry. The auristatin/dolastatin drug moieties may be prepared according to the methods of: U.S. Pat. Nos. 5,635,483 and 5,780,588; Pettit et al., (1989) J. Am. Chem. Soc. 111:5463-5465; Pettit et al., (1998) Anti-Cancer Drug Design 13:243-277; Pettit, G. R., et al., Synthesis, 1996, 719-725; and Pettit et al., (1996) J. Chem. Soc. Perkin Trans. 1 5:859-863. See also Doronina (2003) Nat. Biotechnol. 21(7):778-784; "Monomethylvaline Compounds Capable of Conjugation to Ligands," U.S. Ser. No. 10/983,340, filed Nov. 5, 2004, hereby incorporated by reference in its entirety (disclosing, e.g., linkers and methods of preparing monomethylvaline compounds such as MMAE and MMAF conjugated to linkers).

iii. Calicheamicin

In other embodiments, the immunoconjugate comprises an antibody of the invention conjugated to one or more calicheamicin molecules. The calicheamicin family of antibiotics are capable of producing double-stranded DNA breaks at sub-picomolar concentrations. For the preparation of conjugates of the calicheamicin family, see U.S. Pat. Nos. 5,712,374, 5,714,586, 5,739,116, 5,767,285, 5,770,701, 5,770,710, 5,773,001, and 5,877,296 (all to American Cyanamid Company). Structural analogues of calicheamicin which may be used include, but are not limited to, $\gamma_1^I$, $\alpha_2^I$, $\alpha_3^I$, N-acetyl-$\gamma_1^I$, PSAG and $\theta^I_1$ (Hinman et al., Cancer Research 53:3336-3342 (1993), Lode et al., Cancer Research 58:2925-2928 (1998) and the aforementioned U.S. patents to American Cyanamid). Another anti-tumor drug that the antibody can be conjugated is QFA which is an antifolate. Both calicheamicin and QFA have intracellular sites of action and do not readily cross the plasma membrane. Therefore, cellular uptake of these agents through antibody mediated internalization greatly enhances their cytotoxic effects.

iv. Other Cytotoxic Agents

Other antitumor agents that can be conjugated to the antibodies of the invention include BCNU, streptozoicin, vincristine and 5-fluorouracil, the family of agents known collectively LL-E33288 complex described in U.S. Pat. Nos. 5,053,394 and 5,770,710, as well as esperamicins (U.S. Pat. No. 5,877,296).

Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin and the tricothecenes. See, for example, WO 93/21232 published Oct. 28, 1993.

The present invention further contemplates an immunoconjugate formed between an antibody and a compound with nucleolytic activity (e.g., a ribonuclease or a DNA endonuclease such as a deoxyribonuclease; DNase).

For selective destruction of the tumor, the antibody may comprise a highly radioactive atom. A variety of radioactive isotopes are available for the production of radioconjugated antibodies. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the conjugate is used for detection, it may comprise a radioactive atom for scintigraphic studies, for example $tc^{99m}$ or $I^{123}$, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

The radio- or other labels may be incorporated in the conjugate in known ways. For example, the peptide may be biosynthesized or may be synthesized by chemical amino acid synthesis using suitable amino acid precursors involving, for example, fluorine-19 in place of hydrogen. Labels such as $tc^{99m}$ or $I^{123}$, $Re^{186}$, $Re^{188}$ and $In^{111}$ can be attached via a cysteine residue in the peptide. Yttrium-90 can be attached via a lysine residue. The IODOGEN method (Fraker et al (1978) Biochem. Biophys. Res. Commun. 80: 49-57 can be used to incorporate iodine-123. "Monoclonal Antibodies in Immunoscintigraphy" (Chatal, CRC Press 1989) describes other methods in detail.

Conjugates of the antibody and cytotoxic agent may be made using a variety of bifunctional protein coupling agents such as N-succinimidyl-3-(2-pyridyldithio) propionate (SPDP), succinimidyl-4-(N-maleimidomethyl)cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of the cytotoxic drug in the cell. For example, an acid-labile linker, peptidase-sensitive linker, photolabile linker, dimethyl linker or disulfide-containing linker (Chari et al., Cancer Research 52:127-131 (1992); U.S. Pat. No. 5,208,020) may be used.

The compounds of the invention expressly contemplate, but are not limited to, ADC prepared with cross-linker reagents: BMPS, EMCS, GMBS, HBVS, LC-SMCC, MBS, MPBH, SBAP, SIA, SLAB, SMCC, SMPB, SMPH, sulfo-EMCS, sulfo-GMBS, sulfo-KMUS, sulfo-MBS, sulfo-STAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A). See pages 467-498, 2003-2004 Applications Handbook and Catalog.

v. Preparation of Antibody Drug Conjugates

In the antibody drug conjugates (ADC) of the invention, an antibody (Ab) is conjugated to one or more drug moieties (D), e.g. about 1 to about 20 drug moieties per antibody, through a linker (L). The ADC of Formula I may be prepared by several routes, employing organic chemistry reactions, conditions, and reagents known to those skilled in the art, including: (1) reaction of a nucleophilic group of an antibody with a bivalent linker reagent, to form Ab-L, via a covalent bond, followed by reaction with a drug moiety D; and (2) reaction of a nucleophilic group of a drug moiety with a bivalent linker reagent, to form D-L, via a covalent bond, followed by reaction with the nucleophilic group of an antibody. Additional methods for preparing ADC are described herein.

The linker may be composed of one or more linker components. Exemplary linker components include 6-maleimidocaproyl ("MC"), maleimidopropanoyl ("MP"), valine-citrulline ("val-cit"), alanine-phenylalanine ("ala-phe"), p-aminobenzyloxycarbonyl ("PAB"), N-Succinimidyl 4-(2-pyridylthio) pentanoate ("SPP"), N-Succinimidyl 4-(N-maleimidomethyl)cyclohexane-1 carboxylate ("SMCC'), and N-Succinimidyl (4-iodo-acetyl)aminobenzoate ("SIAB"). Additional linker components are known in the art and some are described herein. See also "Monomethylvaline Compounds Capable of Conjugation to Ligands," U.S. Ser. No. 10/983,340, filed Nov. 5, 2004, the contents of which are hereby incorporated by reference in its entirety.

In some embodiments, the linker may comprise amino acid residues. Exemplary amino acid linker components include a dipeptide, a tripeptide, a tetrapeptide or a pentapeptide. Exemplary dipeptides include: valine-citrulline (vc or val-cit), alanine-phenylalanine (af or ala-phe). Exemplary tripeptides include: glycine-valine-citrulline (gly-val-cit) and glycine-glycine-glycine (gly-gly-gly). Amino acid residues which comprise an amino acid linker component include those occurring naturally, as well as minor amino acids and non-naturally occurring amino acid analogs, such as citrulline. Amino acid linker components can be designed and optimized in their selectivity for enzymatic cleavage by a particular enzymes, for example, a tumor-associated protease, catantigen B, C and D, or a plasmin protease.

Nucleophilic groups on antibodies include, but are not limited to: (i) N-terminal amine groups, (ii) side chain amine groups, e.g. lysine, (iii) side chain thiol groups, e.g. cysteine, and (iv) sugar hydroxyl or amino groups where the antibody is glycosylated. Amine, thiol, and hydroxyl groups are nucleophilic and capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups. Certain antibodies have reducible interchain disulfides, i.e. cysteine bridges. Antibodies may be made reactive for conjugation with linker reagents by treatment with a reducing agent such as DTT (dithiothreitol). Each cysteine bridge will thus form, theoretically, two reactive thiol nucleophiles. Additional nucleophilic groups can be introduced into antibodies through the reaction of lysines with 2-iminothiolane (Traut's reagent) resulting in conversion of an amine into a thiol. Reactive thiol groups may be introduced into the antibody by introducing one, two, three, four, or more cysteine residues (e.g., preparing mutant antibodies comprising one or more non-native cysteine amino acid residues).

Antibody drug conjugates of the invention may also be produced by modification of the antibody to introduce electrophilic moieties, which can react with nucleophilic substituents on the linker reagent or drug. The sugars of glycosylated antibodies may be oxidized, e.g., with periodate oxidizing reagents, to form aldehyde or ketone groups which may react with the amine group of linker reagents or drug moieties. The resulting imine Schiff base groups may form a stable linkage, or may be reduced, e.g., by borohydride reagents to form stable amine linkages. In one embodiment, reaction of the carbohydrate portion of a glycosylated antibody with either glactose oxidase or sodium metaperiodate may yield carbonyl (aldehyde and ketone) groups in the protein that can react with appropriate groups on the drug (Hermanson, Bioconjugate Techniques). In another embodiment, proteins containing N-terminal serine or threo- Ab-(L-D)$_p$      I nine residues can react with sodium meta-periodate, resulting in production of an aldehyde in place of the first amino acid (Geoghegan & Stroh, (1992) Bioconjugate Chem. 3:138-146; U.S. Pat. No. 5,362,852). Such aldehyde can be reacted with a drug moiety or linker nucleophile.

Likewise, nucleophilic groups on a drug moiety include, but are not limited to: amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups.

Alternatively, a fusion protein comprising the antibody and cytotoxic agent may be made, e.g., by recombinant techniques or peptide synthesis. The length of DNA may comprise respective regions encoding the two portions of the conjugate either adjacent one another or separated by a region encoding a linker peptide which does not destroy the desired properties of the conjugate.

In yet another embodiment, the antibody may be conjugated to a "receptor" (such streptavidin) for utilization in tumor pre-targeting wherein the antibody-receptor conjugate is administered to the individual, followed by removal of unbound conjugate from the circulation using a clearing agent and then administration of a "ligand" (e.g., avidin) which is conjugated to a cytotoxic agent (e.g., a radionucleotide).

Pharmaceutical Formulations

Therapeutic formulations of the heterologous polypeptide are prepared for storage by mixing the heterologous polypeptide having the desired degree of purity with optional physiologically acceptable carriers, excipients or stabilizers (Remington's Pharmaceutical Sciences 16th edition, Osol, A. Ed. (1980)), in the form of aqueous solutions, lyophilized or other dried formulations. Acceptable carriers, excipients, or stabilizers are nontoxic to recipients at the dosages and concentrations employed, and include buffers such as phosphate, citrate, histidine and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The formulation herein may also contain more than one active compound as necessary for the particular indication being treated, preferably those with complementary activities that do not adversely affect each other. Such molecules are suitably present in combination in amounts that are effective for the purpose intended.

The active ingredients may also be entrapped in microcapsule prepared, for example, by coacervation techniques or by interfacial polymerization, for example, hydroxymethylcellulose or gelatin-microcapsule and poly-(methyl-methacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the antibody, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(–)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Uses

A heterologous polypeptide of the present invention may be used, for example, to purify, detect, and target a specific polypeptide it recognizes, including both in vitro and in vivo diagnostic and therapeutic methods.

In one aspect, an antibody of the invention can be used in immunoassays for qualitatively and quantitatively measuring specific antigens in biological samples. Conventional methods for detecting antigen-antibody binding includes, for example, an enzyme linked immunosorbent assay (ELISA), an radioimmunoassay (RIA) or tissue immunohistochemistry. Many methods may use a label bound to the antibody for detection purposes. The label used with the antibody is any detectable functionality that does not interfere with its binding to antibody. Numerous labels are known, including the radioisotopes $^{32}P$, $^{32}S$, $^{14}C$, $^{125}I$, $^{3}H$, and $^{131}I$, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, .beta.-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, lactoperoxidase, biotin/avidin, spin labels, bacteriophage labels, stable free radicals, imaging radionuclides (such as Technecium) and the like.

Conventional methods are available to bind these labels covalently to the heterologous polypeptides. For instance, coupling agents such as dialdehydes, carbodiimides, dimaleimides, bis-imidates, bis-diazotized benzidine, and the like may be used to tag the antibodies with the above-described fluorescent, chemiluminescent, and enzyme labels. See, for example, U.S. Pat. No. 3,940,475 (fluorimetry) and U.S. Pat. No. 3,645,090 (enzymes); Hunter et al. *Nature* 144: 945 (1962); David et al. *Biochemistry* 13:1014-1021 (1974); Pain et al. *J. Immunol. Methods* 40:219-230 (1981); and Nygren *Histochem. and Cytochem* 30:407-412 (1982). Preferred labels herein are enzymes such as horseradish peroxidase and alkaline phosphatase. The conjugation of such label, including the enzymes, to the antibody polypeptide is a standard manipulative procedure for one of ordinary skill in immunoassay techniques. See, for example, O'Sullivan et al., "Methods for the Preparation of Enzyme-antibody Conjugates for Use in Enzyme Immunoassay," in Methods in Enzymology, ed. J. J. Langone and H. Van Vunakis, Vol. 73 (Academic Press, New York, N.Y., 1981), pp. 147-166. Such bonding methods are suitable for use with the heterologous polypeptides of this invention.

Alternative to labeling the heterologous polypeptide, antigen can be assayed in biological fluids by a competition immunoassay utilizing a competing antigen standard labeled with a detectable substance and an unlabeled heterologous polypeptide. In this assay, the biological sample, the labeled antigen standards and the heterologous polypeptide are combined and the amount of labeled antigen standard bound to the unlabeled heterologous polypeptide is determined. The amount of tested antigen in the biological sample is inversely proportional to the amount of labeled antigen standard bound to the heterologous polypeptide.

In one aspect, a heterologous polypeptide (such as an antibody) of the invention is particularly useful to detect and profile expressions of specific surface antigens in vitro or in vivo. As discussed before, generally, an aglycosylated antibody does not exert effector functions (i.e., ADCC or CDC activity). Therefore, when the antibody binds to the cell surface antigen, it will not initiate undesirable cytotoxic events. The surface antigen can be specific to a particular cell or tissue type, therefore serving as a marker of the cell or tissue type. Preferably, the surface antigen marker is differentially expressed at various differentiation stages of particular cell or tissue types. The antibody directed against such surface antigen can thus be used for the screening of cell or tissue populations expressing the marker. For example, the antibody of the invention can be used for the screening and isolation of stem cells such as embryonic stem cells, hematopoietic stem cells and mesenchymal stem cells. The antibody of the invention can also be used to detect tumor cells expressing tumor-associated surface antigens such c-met, HER2, HER3 or HER4 receptors An antibody or other heterologous polypeptide of the invention may be used as an affinity purification agent. In this process, the polypeptide is immobilized on a solid phase such a Sephadex resin or filter paper, using methods well known in the art. The immobilized polypeptide is contacted with a sample containing the antigen to be purified, and thereafter the support is washed with a suitable solvent that will remove substantially all the material in the sample except the antigen to be purified, which is bound to the immobilized polypeptide. Finally, the support is washed with another suitable solvent, such as glycine buffer, pH 5.0, that will release the antigen from the polypeptide.

In one aspect, the invention provides uses of a heterologous polypeptide generated using the methods of the invention, in the preparation of a medicament for the therapeutic and/or prophylactic treatment of a disease, such as a cancer, a tumor, a cell proliferative disorder, and/or an immune (such as autoimmune) disorder. The heterologous polypeptide can be of any form described herein, including antibody, antibody fragment, polypeptide (e.g., an oligopeptide), or combination thereof. In some embodiments, the antigen is a human protein molecule and the subject is a human subject.

The heterologous polypeptides of the invention can be used to diagnose, treat, inhibit or prevent diseases, disorders or conditions associated with abnormal expression and or activity of one or more antigen molecules, including but not limited to malignant and benign tumors; non-leukemias and lymphoid malignancies; neuronal, glial, astrocytal, hypothalamic and other glandular, macrophagal, epithelial, stromal and blastocoelic disorders; and inflammatory, angiogenic and immunologic disorders.

In certain embodiments, an immunoconjugate comprising the antibody is administered to the subject. Preferably, the immunoconjugate and/or antigen to which it is bound is/are internalized by the cell Heterologous polypeptides of the present invention can be used either alone or in combination with other compositions in a therapy. For instance, the heterologous polypeptide may be co-administered with an antibody, chemotherapeutic agent(s) (including cocktails of chemotherapeutic agents), other cytotoxic agent(s), anti-angiogenic agent(s), cytokines, and/or growth inhibitory agent(s). Where the heterologous polypeptide inhibits tumor growth, it may be particularly desirable to combine the heterologous polypeptide with one or more other therapeutic agent(s) which also inhibits tumor growth. Alternatively, or additionally, the patient may receive combined radiation therapy (e.g. external beam irradiation or therapy with a radioactive labeled agent, such as an antibody). Such combined therapies noted above include combined administration (where the two or more agents are included in the same or separate formulations), and separate administration, in which case, administration of the antibody can occur prior to, and/or following, administration of the adjunct therapy or therapies.

The heterologous polypeptide (and optionally, an adjunct therapeutic agent) is/are administered by any suitable means, including parenteral, subcutaneous, intraperitoneal, intrapulmonary, and intranasal, and, if desired for local treatment, intralesional administration. Parenteral infusions include intramuscular, intravenous, intraarterial, intraperitoneal, or subcutaneous administration. In addition, the antibody is suitably administered by pulse infusion, particularly with declining doses of the antibody. Preferably the dosing is given by injections, most preferably intravenous or subcutaneous injections, depending in part on whether the administration is brief or chronic.

The heterologous polypeptide composition of the invention will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as used hereinbefore or about from 1 to 99% of the heretofore employed dosages.

For the prevention or treatment of disease, the appropriate dosage of the antibody (when used alone or in combination with other agents such as chemotherapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 µg/kg to 15 mg/kg (e.g. 0.1 mg/kg-10 mg/kg) of antibody is an initial candidate dosage for administration to the patient, whether, for example, by one or more separate administrations, or by continuous infusion. For repeated administrations over several days or longer, depending on the condition, the treatment is sustained until a desired suppression of disease symptoms occurs. The preferred dosage of the antibody will be in the range from about 0.05 mg/kg to about 10 mg/kg. An initial higher loading dose, followed by one or more lower doses may be administered. However, other dosage regimens may be useful. The progress of this therapy is easily monitored by conventional techniques and assays.

Articles of Manufacture

In another embodiment of the invention, an article of manufacture containing materials useful for the treatment of the disorders described above is provided. The article of manufacture comprises a container and a label or package insert on or associated with the container. Suitable containers include, for example, bottles, vials, syringes, etc. The containers may be formed from a variety of materials such as glass or plastic. The container holds a composition which is effective for treating the condition and may have a sterile access port (for example the container may be an intravenous solution bag or a vial having a stopper pierceable by a hypodermic injection needle). At least one active agent in the composition is a antibody of the invention. The label or package insert indicates that the composition is used for treating the condition of choice, such as cancer. Moreover, the article of manufacture may comprise (a) a first container with a composition contained therein, wherein the composition comprises a antibody; and (b) a second container with a composition contained therein, wherein the composition comprises a further cytotoxic agent. The article of manufacture in this embodiment of the invention may further comprise a package insert indicating that the first and second antibody compositions can be used to treat cancer. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The following examples are intended merely to illustrate the practice of the present invention and are not provided by way of limitation. The disclosures of all patent and scientific literatures cited herein are expressly incorporated in their entirety by reference.

EXAMPLES

Materials and Methods

Bacterial strains and media—The strains and plasmids used in this study are listed in Table 1. For shake flask cultures, all strains were grown in Lauria-Bertani (LB) or C.R.A.P. phosphate-limiting media (1) at 30 or 37° C. where indicated. Fermentor medium was essentially as described in reference 1. Antibiotics were added at the following concentrations: 50 µg/mL carbenicillin, 50 µg/mL kanamycin, 12.5 µg/mL chloramphenicol, or 20 µg/mL tetracycline.

Construction and evaluation of relative TIR libraries—The heat-stable enterotoxin II (stII), maltose-binding periplasmic protein (malE), alkaline phosphatase (phoA), or thiol:disulfide interchange protein (dsbA) signal peptides were PCR-amplified and fused to the mature domain of the phoA gene using degenerate primers that introduced wobble-based silent codon mutations (2) in the first six amino acids after the parental gene's initiation codon with a BssHII, MluI, or XbaI restriction site nine base pairs (bps) upstream of said initiation codon (see Table 2). DNAs encoding for the wild-type codons of each signal sequence were also generated. These inserts were then routinely cloned into the SpeI/NotI (New England Biolabs) sites of the pPho41 (3) plasmid and transformed into competent JM109 cells (Promega), recovered for one hour and subcultured in 200 mL of LB supplemented with cabenicillin at 37° C. for sixteen hours and subsequently maxi-prepped (Qiagen). An aliquot of recovered cells from each library was plated on selective LB-agar plates in order to determine library size; all libraries produced between ~10-100× coverage over theoretical library sizes. Purified DNA was then transformed into competent 27C7 cells and plated on LB-agar plates supplemented with carbenicillin and 100 µg/mL 5-bromo-4-chloro-3-indolyl phosphate (BCIP; Sigma) and grown at 37° C. for sixteen hours. Colonies that appeared light blue putatively indicated they harbored a TIR variant displaying at least a low level of PhoA activity, while dark blue colonies were indicative of cells harboring strong TIR variants (4), and white colonies implied the cells were carrying TIR variants with little to no PhoA expression; the percentage of blue colonies on a given agar plate for each library ranged from ~2-70%. DNA from individual colonies displaying varying hues of blue was miniprepped (Qiagen), sequenced by SRS Analysis (Genentech, Inc.), retransformed into competent 27C7 cells and then tested for their basal PhoA activities as previously described (3). Briefly, colonies were grown in selective LB at 30° C. for sixteen hours and diluted 1:100 into fresh media and grown for an additional four hours at 30° C. Cultures were then normalized based on optical density ($OD_{550}$) and resuspended in strict-AP media (3), then stored at −20° C. overnight. Cells were then thawed, partially permeabilized with toluene (Sigma) treatment (5) and aerated at 37° C. for one hour. Forty microliters of each culture was then added to a solution containing 1 mM disodium 4-nitrophenyl phosphate hexahydrate (PNPP; Promega) in 1 M Tris-HCl buffer (pH 8.0) and incubated in darkness at room temperature for one hour. Reactions were stopped with the addition of 100 µL sodium phosphate buffer (pH 6.5) and the absorbance at 410 nm ($A_{410}$) was read within 20 minutes. Relative TIR strengths were calculated by first subtracting from each sample's $A_{410}$ the background absorbance from a culture containing empty vector (pBR322) and then dividing by the corrected absorbance from a culture carrying the pPho41 plasmid. All reported TIR values are the result of at least seven replicate experiments.

Construction of antibody expression vectors—Signal peptides were routinely cloned into the previously described two-cistron system (1). Heavy chain signal peptide variants were created by fusing the signal peptide of interest via splicing overlap extension-(SOE) PCR to the heavy chain of interest and cloned into BssHII/HpaI (New England Biolabs) sites. Light chain signal peptide variants were similarly made using SOE-PCR and cloned into MluI/PacI (New England Biolabs) or XbaI/PacI (New England Biolabs) sites as specified by the individual TIR variant nucleotide sequence (Table 2). All construct sequences were confirmed by SRS Analysis (Genentech, Inc).

Small scale induction and analysis—Cells were grown in 5 mL of selective LB supplemented with 5 mM sodium phosphate (pH 7.0) at 30° C. for 16 hours. A 500 µL aliquot of cells were then used to inoculate 25 mL of selective C.R.A.P. phosphate-limiting media and grown for 24 hours at 30° C. Where indicated, cells carrying the plasmid pJJ247 were induced with isopropyl β-D-thiogalactoside (IPTG) to a final concentration of 1.0 mM when the cells reached an $OD_{600}$~2.0. End point whole broth samples were taken and diluted to an $OD_{600}$ of ~3.0 in lysis buffer (10 mM Tris pH 6.8, 5 mM EDTA, 0.2 mg/mL lysozyme (Sigma), 5 mM iodoacetic acid (Sigma)) and incubated on ice for 10 minutes. Samples were sonicated, centrifuged to remove cell debris and then analyzed using SDS-PAGE analysis (10% Bis-Tris, Invitrogen). Whole cell lysate samples were normalized to equivalent optical densities reduced with 0.2 M dithiothreitol (DTT, Sigma), and analyzed using SDS-PAGE analysis. All lanes were loaded with equivalent volumes of samples and probed using with either a human anti-Fc (Southern Biotech) antibody at a 1:200,000 dilution or a mouse anti-κLc (Southern Biotech) antibody at a 1:200,000 dilution. All antibodies were HRP-conjugated and immunoblots were visualized using Western Lightning-ECL (PerkinElmer) and exposing the membrane to Biomax XAR Film (Kodak). Protein samples were also analyzed via Coomassie blue staining following standard techniques.

Large scale induction—Fermentations were performed as previously described (1). Briefly, a 500 µL aliquot of cryopreserved cells from a 5 mL selective LB culture was used to inoculate 500 mL of selective LB and grown at 30° C. for 16 hours. A 10-L fermentor was then inoculated (essentially as described in ref. 1) and cells were grown to a high density using a computer-based algorithm to feed a concentrated glucose solution based on fermentation demands. Where indicated, cells carrying the plasmid pJJ247 were induced with Where indicated, cells carrying the plasmid pJJ247 were induced with isopropyl β-D-thiogalactoside (IPTG) to a final concentration of 1.0 M when the cells reached an $OD_{550}$~200. Whole broth and normalized $OD_{550}$ samples were taken at regular time intervals and all fermentations were terminated after 2-3 days. Culture fitness was routinely monitored using online and offline measured parameters. Samples were analyzed using SDS-PAGE analysis as described above.

HPLC analysis of samples—Samples from either small or large scale induction experiments were analyzed for total (insoluble and soluble) heavy or light chain concentrations through a previously developed reversed-phase HPLC analysis technique (Lisa Wong, personal communication). Samples were analyzed for light-chain containing antibody species by a dual-column, Protein-L reverse phase based HPLC assay (Analytical Operations, Genentech, Inc.). Antibody titers were obtained by comparing chromatogram peak areas to those of a standard curve generated by spiking blank samples with known amounts of molecule of interest.

TABLE 1

Strains and plasmids used in this study

| Strain or plasmid | Relevant genotype/phenotype | Reference or source |
|---|---|---|
| *E. coli* strains | | |
| 27C7 | ΔfhuA (ΔtonA) phoAΔE15 Δ(argF-lac)169 ptr3 degP41 kan$^R$ ompTΔ(nmpc-fepE) | (3) |
| 64B4 | W3110 ΔfhuA ΔphoA ilvG+ Δprc spr43H1 ΔdegP ΔmanA lacI$^q$ ΔompT | Laboratory stock |
| JM109 | e14$^-$(McrA$^-$) recA1 endA1 gyrA96 thi-1 hsdR17 ($r_K^-$ $m_K^+$) supE44 relA1 Δ(lac-proAB) [F' traD36 proAB lacI$^q$ZΔM15] | Promega |
| Plasmids | | |
| pPho41 | Cb$^r$ | (3) |
| pBR322 | Cb$^r$, Tc$^r$ | Laboratory stock |
| ph5D5 | Humanized 5D5 antibody (interchangeably termed 5D5.v2 antibody) cloned into pBR322 | Laboratory stock' |
| pJJ247 | *E. coli* dsbA and dsbC under control of the tac promoter in a pACYC-derived vector, Km$^r$ | Laboratory stock |
| pBR-STIIHc1.0-PhoA | *E. coli* BssHIII-ssSTII TIRv.1 fused to Δ(1-22)PhoA in pPho41 | This study |
| pBR-STIIHc2.41-PhoA | *E. coli* BssHIII-ssSTII TIRv.2 fused to Δ(1-22)PhoA in pPho41 | This study |
| pBR-STIIHc3.38-PhoA | *E. coli* BssHIII-ssSTII TIRv.3 fused to Δ(1-22)PhoA in pPho41 | This study |
| pBR-STIIHc4.60-PhoA | *E. coli* BssHIII-ssSTII TIRv.4 fused to Δ(1-22)PhoA in pPho41 | This study |
| pBR-STIIHc5.34-PhoA | *E. coli* BssHIII-ssSTII TIRv.5 fused to Δ(1-22)PhoA in pPho41 | This study |
| pBR-STIIHc6.52-PhoA | *E. coli* BssHIII-ssSTII TIRv.6 fused to Δ(1-22)PhoA in pPho41 | This study |
| pBR-STIIHc8.36-PhoA | *E. coli* BssHIII-ssSTII TIRv.8 fused to Δ(1-22)PhoA in pPho41 | This study |
| pBR-STIILc1.0-PhoA | *E. coli* MluI-ssSTII TIRv.1 fused to Δ(1-22)PhoA in pPho41 | This study |
| pBR-STIILc2.74-PhoA | *E. coli* MluI-ssSTII TIRv.2 fused to Δ(1-22)PhoA in pPho41 | This study |

TABLE 1-continued

Strains and plasmids used in this study

| Strain or plasmid | Relevant genotype/phenotype | Reference or source |
|---|---|---|
| pBR-STIILc3.72-PhoA | E. coli MluI-ssSTII TIRv.3 fused to Δ(1-22)PhoA in pPho41 | This study |
| pBR-DsbAHc1.48-PhoA | E. coli BssHII-ssDsbA TIRv.1 fused to Δ(1-22)PhoA in pPho41 | This study |
| pBR-DsbAHc2.WT-PhoA | E. coli BssHII-ssDsbA TIRv.2 fused to Δ(1-22)PhoA in pPho41 | This study |
| pBR-DsbAHc3.79-PhoA | E. coli BssHII-ssDsbA TIRv.3 fused to Δ(1-22)PhoA in pPho41 | This study |
| pBR-DsbAHc7.72-PhoA | E. coli BssHII-ssDsbA TIRv.7 fused to Δ(1-22)PhoA in pPho41 | This study |
| pBR-DsbALc1.WT-PhoA | E. coli MluI-ssDsbA TIRv.1 fused to Δ(1-22)PhoA in pPho41 | This study |
| pBR-DsbALc2.3-PhoA | E. coli MluI-ssDsbA TIRv.2 fused to Δ(1-22)PhoA in pPho41 | This study |
| pBR-DsbALc3.37-PhoA | E. coli MluI-ssDsbA TIRv.3 fused to Δ(1-22)PhoA in pPho41 | This study |
| pBR-PhoAHc1.70-PhoA | E. coli BssHII-ssPhoA TIRv.1 fused to Δ(1-22)PhoA in pPho41 | This study |
| pBR-PhoAHc2.64-PhoA | E. coli BssHII-ssPhoA TIRv.2 fused to Δ(1-22)PhoA in pPho41 | This study |
| pBR-PhoAHc3.WT-PhoA | E. coli BssHII-ssPhoA TIRv.3 fused to Δ(1-22)PhoA in pPho41 | This study |
| pBR-PhoAHc4.67-PhoA | E. coli BssHII-ssPhoA TIRv.4 fused to Δ(1-22)PhoA in pPho41 | This study |
| pBR-PhoAHc5.71-PhoA | E. coli BssHII-ssPhoA TIRv.5 fused to Δ(1-22)PhoA in pPho41 | This study |
| pBR-PhoAHc6.77-PhoA | E. coli BssHII-ssPhoA TIRv.6 fused to Δ(1-22)PhoA in pPho41 | This study |
| pBR-PhoALc1.104-PhoA | E. coli MluI-ssPhoA TIRv.1 fused to Δ(1-22)PhoA in pPho41 | This study |
| pBR-PhoAXb2.41-PhoA | E. coli XbaI-ssPhoA TIRv.2 fused to Δ(1-22)PhoA in pPho41 | This study |
| pBR-PhoAXb3.WT-PhoA | E. coli XbaI-ssPhoA TIRv.3 fused to Δ(1-22)PhoA in pPho41 | This study |
| pBR-PhoAXb5.53-PhoA | E. coli XbaI-ssPhoA TIRv.5 fused to Δ(1-22)PhoA in pPho41 | This study |
| pBR-PhoAXb6.15-PhoA | E. coli XbaI-ssPhoA TIRv.6 fused to Δ(1-22)PhoA in pPho41 | This study |
| pBR-PhoAXb7.1-PhoA | E. coli XbaI-ssPhoA TIRv.7 fused to Δ(1-22)PhoA in pPho41 | This study |
| pBR-PhoAXb8.24-PhoA | E. coli XbaI-ssPhoA TIRv.8 fused to Δ(1-22)PhoA in pPho41 | This study |
| pBR-PhoAXb10.23-PhoA | E. coli XbaI-ssPhoA TIRv.10 fused to Δ(1-22)PhoA in pPho41 | This study |
| pBR-MalEHc1.92-PhoA | E. coli BssHII-ssMalE TIRv.1 fused to Δ(1-22)PhoA in pPho41 | This study |
| pBR-MalEHc2.100-PhoA | E. coli BssHII-ssMalE TIRv.2 fused to Δ(1-22)PhoA in pPho41 | This study |
| pBR-MalELc1.97-PhoA | E. coli MluI-ssMalE TIRv.1 fused to Δ(1-22)PhoA in pPho41 | This study |
| pBR-MalELc2.123-PhoA | E. coli MluI-ssMalE TIRv.2 fused to Δ(1-22)PhoA in pPho41 | This study |
| pBR-MalEXb1.WT-PhoA | E. coli XbaI-ssMalE TIRv.1 fused to Δ(1-22)PhoA in pPho41 | This study |
| pBR-MalEXb2.15-PhoA | E. coli XbaI-ssMalE TIRv.2 fused to Δ(1-22)PhoA in pPho41 | This study |
| pBR-MalEXb3.12-PhoA | E. coli XbaI-ssMalE TIRv.3 fused to Δ(1-22)PhoA in pPho41 | This study |
| pBR-MalEXb5.37-PhoA | E. coli XbaI-ssMalE TIRv.5 fused to Δ(1-22)PhoA in pPho41 | This study |
| pBR-MalEXb6.4-PhoA | E. coli XbaI-ssMalE TIRv.6 fused to Δ(1-22)PhoA in pPho41 | This study |
| pBR-MalEXb7.25-PhoA | E. coli XbaI-ssMalE TIRv.7 fused to Δ(1-22)PhoA in pPho41 | This study |
| pBR-MalEXb8.13-PhoA | E. coli XbaI-ssMalE TIRv.8 fused to Δ(1-22)PhoA in pPho41 | This study |
| pBR-MalEXb11.34-PhoA | E. coli XbaI-ssMalE TIRv.11 fused to Δ(1-22)PhoA in pPho41 | This study |
| pBR-SS-5D5-1.1 | STII TIRv.1 fused to 5D5 Hc, STII TIRv.1 fused to 5D5 Lc | This study |
| pBR-SS-5D5-1.2 | STII TIRv.1 fused to 5D5 Hc, STII TIRv.2 fused to 5D5 Lc | This study |
| pBR-SS-5D5-2.1 | STII TIRv.2 fused to 5D5 Hc, STII TIRv.1 fused to 5D5 Lc | This study |

TABLE 1-continued

Strains and plasmids used in this study

| Strain or plasmid | Relevant genotype/phenotype | Reference or source |
|---|---|---|
| pBR-SS-5D5-2.2 | STII TIRv.2 fused to 5D5 Hc, STII TIRv.2 fused to 5D5 Lc | This study |
| pBR-SM-5D5-1.1 | STII TIRv.1 fused to 5D5 Hc, MalE TIRv.1 fused to 5D5 Lc | This study |
| pBR-SM-5D5-1.2 | STII TIRv.1 fused to 5D5 Hc, MalE TIRv.2 fused to 5D5 Lc | This study |
| pBR-SM-5D5-2.1 | STII TIRv.2 fused to 5D5 Hc, MalE TIRv.1 fused to 5D5 Lc | This study |
| pBR-SM-5D5-2.2 | STII TIRv.2 fused to 5D5 Hc, MalE TIRv.2 fused to 5D5 Lc | This study |
| pBR-SD-5D5-1.1 | STII TIRv.1 fused to 5D5 Hc, DsbA TIRv.1 fused to 5D5 Lc | This study |
| pBR-SD-5D5-1.2 | STII TIRv.1 fused to 5D5 Hc, DsbA TIRv.2 fused to 5D5 Lc | This study |
| pBR-SD-5D5-2.1 | STII TIRv.2 fused to 5D5 Hc, DsbA TIRv.1 fused to 5D5 Lc | This study |
| pBR-SD-5D5-2.2 | STII TIRv.2 fused to 5D5 Hc, DsbA TIRv.2 fused to 5D5 Lc | This study |
| pBR-SP-5D5-1.1 | STII TIRv.1 fused to 5D5 Hc, PhoA TIRv.1 fused to 5D5 Lc | This study |
| pBR-SP-5D5-1.2 | STII TIRv.1 fused to 5D5 Hc, PhoA TIRv.2 fused to 5D5 Lc | This study |
| pBR-SP-5D5-2.1 | STII TIRv.2 fused to 5D5 Hc, PhoA TIRv.1 fused to 5D5 Lc | This study |
| pBR-SP-5D5-2.2 | STII TIRv.2 fused to 5D5 Hc, PhoA TIRv.2 fused to 5D5 Lc | This study |
| pBR-MS-5D5-1.1 | MalE TIRv.1 fused to 5D5 Hc, STII TIRv.1 fused to 5D5 Lc | This study |
| pBR-MS-5D5-1.2 | MalE TIRv.1 fused to 5D5 Hc, STII TIRv.2 fused to 5D5 Lc | This study |
| pBR-MS-5D5-2.1 | MalE TIRv.2 fused to 5D5 Hc, STII TIRv.1 fused to 5D5 Lc | This study |
| pBR-MS-5D5-2.2 | MalE TIRv.2 fused to 5D5 Hc, STII TIRv.2 fused to 5D5 Lc | This study |
| pBR-MM-5D5-1.1 | MalE TIRv.1 fused to 5D5 Hc, MalE TIRv.1 fused to 5D5 Lc | This study |
| pBR-MM-5D5-1.2 | MalE TIRv.1 fused to 5D5 Hc, MalE TIRv.2 fused to 5D5 Lc | This study |
| pBR-MM-5D5-2.1 | MalE TIRv.2 fused to 5D5 Hc, MalE TIRv.1 fused to 5D5 Lc | This study |
| pBR-MM-5D5-2.2 | MalE TIRv.2 fused to 5D5 Hc, MalE TIRv.2 fused to 5D5 Lc | This study |
| pBR-MD-5D5-1.1 | MalE TIRv.1 fused to 5D5 Hc, DsbA TIRv.1 fused to 5D5 Lc | This study |
| pBR-MD-5D5-1.2 | MalE TIRv.1 fused to 5D5 Hc, DsbA TIRv.2 fused to 5D5 Lc | This study |
| pBR-MD-5D5-2.1 | MalE TIRv.2 fused to 5D5 Hc, DsbA TIRv.1 fused to 5D5 Lc | This study |
| pBR-MD-5D5-2.2 | MalE TIRv.2 fused to 5D5 Hc, DsbA TIRv.2 fused to 5D5 Lc | This study |
| pBR-MP-5D5-1.1 | MalE TIRv.1 fused to 5D5 Hc, PhoA TIRv.1 fused to 5D5 Lc | This study |
| pBR-MP-5D5-1.2 | MalE TIRv.1 fused to 5D5 Hc, PhoA TIRv.2 fused to 5D5 Lc | This study |
| pBR-MP-5D5-2.1 | MalE TIRv.2 fused to 5D5 Hc, PhoA TIRv.1 fused to 5D5 Lc | This study |
| pBR-MP-5D5-2.2 | MalE TIRv.2 fused to 5D5 Hc, PhoA TIRv.2 fused to 5D5 Lc | This study |
| pBR-DS-5D5-1.1 | DsbA TIRv.1 fused to 5D5 Hc, STII TIRv.1 fused to 5D5 Lc | This study |
| pBR-DS-5D5-1.2 | DsbA TIRv.1 fused to 5D5 Hc, STII TIRv.2 fused to 5D5 Lc | This study |
| pBR-DS-5D5-2.1 | DsbA TIRv.2 fused to 5D5 Hc, STII TIRv.1 fused to 5D5 Lc | This study |
| pBR-DS-5D5-2.2 | DsbA TIRv.2 fused to 5D5 Hc, STII TIRv.2 fused to 5D5 Lc | This study |
| pBR-DM-5D5-1.1 | DsbA TIRv.1 fused to 5D5 Hc, MalE TIRv.1 fused to 5D5 Lc | This study |
| pBR-DM-5D5-1.2 | DsbA TIRv.1 fused to 5D5 Hc, MalE TIRv.2 fused to 5D5 Lc | This study |
| pBR-DM-5D5-2.1 | DsbA TIRv.2 fused to 5D5 Hc, MalE TIRv.1 fused to 5D5 Lc | This study |
| pBR-DM-5D5-2.2 | DsbA TIRv.2 fused to 5D5 Hc, MalE TIRv.2 fused to 5D5 Lc | This study |

TABLE 1-continued

Strains and plasmids used in this study

| Strain or plasmid | Relevant genotype/phenotype | Reference or source |
|---|---|---|
| pBR-DD-5D5-1.1 | DsbA TIRv.1 fused to 5D5 Hc, DsbA TIRv.1 fused to 5D5 Lc | This study |
| pBR-DD-5D5-1.2 | DsbA TIRv.1 fused to 5D5 Hc, DsbA TIRv.2 fused to 5D5 Lc | This study |
| pBR-DD-5D5-2.1 | DsbA TIRv.2 fused to 5D5 Hc, DsbA TIRv.1 fused to 5D5 Lc | This study |
| pBR-DD-5D5-2.2 | DsbA TIRv.2 fused to 5D5 Hc, DsbA TIRv.2 fused to 5D5 Lc | This study |
| pBR-DP-5D5-1.1 | DsbA TIRv.1 fused to 5D5 Hc, PhoA TIRv.1 fused to 5D5 Lc | This study |
| pBR-DP-5D5-1.2 | DsbA TIRv.1 fused to 5D5 Hc, PhoA TIRv.2 fused to 5D5 Lc | This study |
| pBR-DP-5D5-2.1 | DsbA TIRv.2 fused to 5D5 Hc, PhoA TIRv.1 fused to 5D5 Lc | This study |
| pBR-DP-5D5-2.2 | DsbA TIRv.2 fused to 5D5 Hc, PhoA TIRv.2 fused to 5D5 Lc | This study |
| pBR-PS-5D5-1.1 | PhoA TIRv.1 fused to 5D5 Hc, STII TIRv.1 fused to 5D5 Lc | This study |
| pBR-PS-5D5-1.2 | PhoA TIRv.1 fused to 5D5 Hc, STII TIRv.2 fused to 5D5 Lc | This study |
| pBR-PS-5D5-2.1 | PhoA TIRv.2 fused to 5D5 Hc, STII TIRv.1 fused to 5D5 Lc | This study |
| pBR-PS-5D5-2.2 | PhoA TIRv.2 fused to 5D5 Hc, STII TIRv.2 fused to 5D5 Lc | This study |
| pBR-PM-5D5-1.1 | PhoA TIRv.1 fused to 5D5 Hc, MalE TIRv.1 fused to 5D5 Lc | This study |
| pBR-PM-5D5-1.2 | PhoA TIRv.1 fused to 5D5 Hc, MalE TIRv.2 fused to 5D5 Lc | This study |
| pBR-PM-5D5-2.1 | PhoA TIRv.2 fused to 5D5 Hc, MalE TIRv.1 fused to 5D5 Lc | This study |
| pBR-PM-5D5-2.2 | PhoA TIRv.2 fused to 5D5 Hc, MalE TIRv.2 fused to 5D5 Lc | This study |
| pBR-PD-5D5-1.1 | PhoA TIRv.1 fused to 5D5 Hc, DsbA TIRv.1 fused to 5D5 Lc | This study |
| pBR-PD-5D5-1.2 | PhoA TIRv.1 fused to 5D5 Hc, DsbA TIRv.2 fused to 5D5 Lc | This study |
| pBR-PD-5D5-2.1 | PhoA TIRv.2 fused to 5D5 Hc, DsbA TIRv.1 fused to 5D5 Lc | This study |
| pBR-PD-5D5-2.2 | PhoA TIRv.2 fused to 5D5 Hc, DsbA TIRv.2 fused to 5D5 Lc | This study |
| pBR-PP-5D5-1.1 | PhoA TIRv.1 fused to 5D5 Hc, PhoA TIRv.1 fused to 5D5 Lc | This study |
| pBR-PP-5D5-1.2 | PhoA TIRv.1 fused to 5D5 Hc, PhoA TIRv.2 fused to 5D5 Lc | This study |
| pBR-PP-5D5-2.1 | PhoA TIRv.2 fused to 5D5 Hc, PhoA TIRv.1 fused to 5D5 Lc | This study |
| pBR-PP-5D5-2.2 | PhoA TIRv.2 fused to 5D5 Hc, PhoA TIRv.2 fused to 5D5 Lc | This study |

Hc = heavy chain
Lc = light chain
5D5 = anti-c-met monoclonal antibody clone 5D5.v2. 5D5.v2 heavy and light chain sequences are shown in FIG. 7 and are also described in, e.g., WO2006/015371; Jin et al, Cancer Res (2008) 68: 4360.

TABLE 2 signal sequence variants

| Parent gene | Clone ID | Relevant genotype/phenotype | Relative TIR strength | SEQ ID NO: |
|---|---|---|---|---|
| stII | SH1.2 | GCGCGCATTATGAAGAAAAACATCGCTTTTCTTCTTGCATCTATGTTCGTTTTTTCTATTGCTACAAACGCTTACGCT | 0.99 ± 0.07 | 1 |
| | SH2.41 | GCGCGCATTATGAAAAAAAAATATAGCGTTCTTCTTGCATCTATGTTCGTTTTTTCTATTGCTACAAACGCTTACGCT | 1.94 ± 0.05 | 2 |

TABLE 2-continued signal sequence variants

| Parent gene | Clone ID | Relevant genotype/phenotype | Relative TIR strength | SEQ ID NO: |
|---|---|---|---|---|
| | SH3.38 | GCGCGCATTATGAAAAAAAACATTGCCTTTCTTCTTGCATCTATGTTCGTTTTTTCTATTGCTACAAACGCTTACGCT | 2.9 ± 0.2 | 3 |
| | SH4.60 | GCGCGCATTATGAAAAAGAATATTGCCTTTCTTCTTGCATCTATGTTCGTTTTTTCTATTGCTACAAACGCTTACGCT | 4.1 ± 0.1 | 4 |
| | SH5.34 | GCGCGCATTATGAAGAAAAATATTGCATTCCTTCTTGCATCTATGTTCGTTTTTTCTATTGCTACAAACGCTTACGCT | 5.0 ± 0.2 | 5 |
| | SH6.52 | GCGCGCATTATGAAAAAAAATATTGCATTTCTTCTTGCATCTATGTTCGTTTTTTCTATTGCTACAAACGCTTACGCT | 5.9 ± 0.2 | 6 |
| | SH8.36 | GCGCGCATTATGAAAAAAAATATTGCTTTTCTTCTTGCATCTATGTTCGTTTTTTCTATTGCTACAAACGCTTACGCT | 7.7 ± 0.1 | 7 |
| | SL1.2 | ACGCGTATTATGAAGAAAAACATCGCTTTTCTTCTTGCATCTATGTTCGTTTTTTCTATTGCTACAAACGCTTACGCT | 0.75 ± 0.07 | 8 |
| | SL2.74 | ACGCGTATTATGAAAAAGAATATCGCCTTTCTTCTTGCATCTATGTTCGTTTTTTCTATTGCTACAAACGCTTACGCT | 1.9 ± 0.2 | 9 |
| | SL3.72 | ACGCGTATTATGAAAAAAAATATTGCTTTTCTTCTTGCATCTATGTTCGTTTTTTCTATTGCTACAAACGCTTACGCT | 2.9 ± 0.2 | 10 |
| malE | MH1.92 | GCGCGCATTATGAAAATTAAGACTGGAGCACGCATCCTCGCATTATCCGCATTAACGACGATGATGTTTTCCGCCTCGGCTCTCGCC | 1.1 ± 0.1 | 11 |
| | MH2.100 | GCGCGCATTATGAAGATTAAAACCGGAGCCCGCATCCTCGCATTATCCGCATTAACGACGATGATGTTTTCCGCCTCGGCTCTCGCC | 1.9 ± 0.1 | 12 |
| | ML1.97 | ACGCGTATTATGAAGATCAAGACAGGCGCGCGCATCCTCGCATTATCCGCATTAACGACGATGATGTTTTCCGCCTCGGCTCTCGCC | 1.1 ± 0.1 | 13 |
| | ML2.123 | ACGCGTATTATGAAGATCAAGACAGGGGCCCGCATCCTCGCATTATCCGCATTAACGACGATGATGTTTTCCGCCTCGGCTCTCGCC | 2.0 ± 0.1 | 14 |
| | MX1.wt | TCTAGAATTATGAAAATTAAAAACAGGTGCACGCATCCTCGCATTATCCGCATTAACGACGATGATGTTTTCCGCCTCGGCTCTCGCC | 1.1 ± 0.1 | 15 |
| | MX2.15 | TCTAGAATTATGAAAATTAAGACGGGGGCGCGCATCCTCGCATTATCCGCATTAACGACGATGATGTTTTCCGCCTCGGCTCTCGCC | 2.0 ± 0.1 | 16 |
| | MX3.12 | TCTAGAATTATGAAAATCAAAACCGGCGCTCGCATCCTCGCATTATCCGCATTAACGACGATGATGTTTTCCGCCTCGGCTCTCGCC | 3.01 ± 0.09 | 17 |

TABLE 2-continued signal sequence variants

| Parent gene | Clone ID | Relevant genotype/phenotype | Relative TIR strength | SEQ ID NO: |
|---|---|---|---|---|
| | MX5.37 | TCTAGAATTATGAAGATCAAGACTGGAGCTCGCATCCTCGCATTATCCGCATTAAC GACGATGATGTTTTCCGCCTCGGCTCTC GCC | 5.0 ± 0.2 | 18 |
| | MX6.4 | TCTAGAATTATGAAAATAAAGACGGGAGCTCGCATCCTCGCATTATCCGCATTAAC GACGATGATGTTTTCCGCCTCGGCTCTC GCC | 5.8 ± 0.3 | 19 |
| | MX7.25 | TCTAGAATTATGAAGATTAAAGACTGGTGCGCGCATCCTCGCATTATCCGCATTAAC GACGATGATGTTTTCCGCCTCGGCTCTC GCC | 7.1 ± 0.2 | 20 |
| | MX8.13 | TCTAGAATTATGAAAATTAAGACGGGAGCACGCATCCTCGCATTATCCGCATTAAC GACGATGATGTTTTCCGCCTCGGCTCTC GCC | 8.2 ± 0.3 | 21 |
| | MX11.34 | TCTAGAATTATGAAGATTAAGACGGGCGCTCGCATCCTCGCATTATCCGCATTAAC GACGATGATGTTTTCCGCCTCGGCTCTC GCC | 10.8 ± 0.5 | 22 |
| phoA | PH1.70 | GCGCGCATTATGAAACAATCCACGATTGCCCTGGCACTCTTACCGTTACTGTTTAC CCCTGTGACAAAAGCC | 1.14 ± 0.05 | 23 |
| | PH2.64 | GCGCGCATTATGAAACAGTCGACGATCGCACTGGCACTCTTACCGTTACTGTTTAC CCCTGTGACAAAAGCC | 1.93 ± 0.03 | 24 |
| | PH3.wt | GCGCGCATTATGAAACAAAGCACTATTGCACTGGCACTCTTACCGTTACTGTTTAC CCCTGTGACAAAAGCC | 2.8 ± 0.1 | 25 |
| | PH4.67 | GCGCGCATTATGAAGCAATCTACTATCGCTCTGGCACTCTTACCGTTACTGTTTAC CCCTGTGACAAAAGCC | 3.7 ± 0.1 | 26 |
| | PH5.71 | GCGCGCATTATGAAGCAATCAACTATCGCACTGGCACTCTTACCGTTACTGTTTAC CCCTGTGACAAAAGCC | 5.1 ± 0.3 | 27 |
| | PH6.77 | GCGCGCATTATGAAACAATCTACTATTGCACTGGCACTCTTACCGTTACTGTTTAC CCCTGTGACAAAAGCC | 6.0 ± 0.4 | 28 |
| | PL1.104 | ACGCGTATTATGAAACAGTCTACTATCGCTCTCTGGCACTCTTACCGTTACTGTTTAC CCCTGTGACAAAAGCC | 1.00 ± 0.07 | 29 |
| | PX2.41 | TCTAGAATTATGAAGCAGAGTACGATTGCTCTGGCACTCTTACCGTTACTGTTTAC CCCTGTGACAAAAGCC | 2.0 ± 0.1 | 30 |
| | PX3.wt | TCTAGAATTATGAAACAAAGCACTATTGCACTGGCACTCTTACCGTTACTGTTTAC CCCTGTGACAAAAGCC | 3.39 ± 0.09 | 31 |
| | PX5.53 | TCTAGAATTATGAAGCAATCCACAATAGCTCTGGCACTCTTACCGTTACTGTTTAC CCCTGTGACAAAAGCC | 4.9 ± 0.1 | 32 |
| | PX6.15 | TCTAGAATTATGAAACAATCCACCATTGCCCTGGCACTCTTACCGTTACTGTTTACC CCTGTGACAAAAGCC | 5.9 ± 0.2 | 33 |
| | PX8.24 | TCTAGAATTATGAAACAGTCTACTATCGCGCTGGCACTCTTACCGTTACTGTTTACC CCTGTGACAAAAGCC | 8.0 ± 0.1 | 34 |

TABLE 2-continued signal sequence variants

| Parent gene | Clone ID | Relevant genotype/phenotype | Relative TIR strength | SEQ ID NO: |
|---|---|---|---|---|
| | PX10.23 | TCTAGAATTATGAAACAATCCACAATCG CACTGGCACTCTTACCGTTACTGTTTAC CCCTGTGACAAAAGCC | 10.0 ± 0.4 | 35 |
| dsbA | DH1.48 | GCGCGCATTATGAAAAAAATTTGGCTCG CCCTGGCTGGTTTAGTTTTAGCGTTTAG CGCATCGGCG | 0.80 ± 0.03 | 36 |
| | DH2.wt | GCGCGCATTATGAAAAAGATTTGGCTGG CGCTGGCTGGTTTAGTTTTAGCGTTTAG CGCATCGGCG | 1.89 ± 0.09 | 37 |
| | DH3.79 | GCGCGCATTATGAAAAAGATATGGCTGG CTCTGGCTGGTTTAGTTTTAGCGTTTAG CGCATCGGCG | 2.92 ± 0.08 | 38 |
| | DH7.72 | GCGCGCATTATGAAAAAGATATGGTTGG CTCTGGCTGGTTTAGTTTTAGCGTTTAG CGCATCGGCG | 6.7 ± 0.2 | 39 |
| | DL1.wt | ACGCGTATTATGAAAAAGATTTGGCTGG CGCTGGCTGGTTTAGTTTTAGCGTTTAG CGCATCGGCG | 1.0 ± 0.1 | 40 |
| | DL2.3 | ACGCGTATTATGAAGAAAATTTGGTTGG CTCTGGCTGGTTTAGTTTTAGCGTTTAG CGCATCGGCG | 1.87 ± 0.09 | 41 |
| | DL3.37 | ACGCGTATTATGAAGAAGATTTGGTTA GCACTGGCTGGTTTAGTTTTAGCGTTTA GCGCATCGGCG | 2.6 ± 0.1 | 42 |

Legend: Clone naming convention is as follows:
XY.# = X designates the signal sequence (S = STII, P = PhoA and so on);
Y designates the restriction sequence (H means the BsshII restriction site, X designates the XbaI site, L designates the MluI restriction site) and # designates the TIR strength (eg, 1 = TIR of 1, 7.72 = TIR of 7.72). wt = wildtype TIR sequence.
Bold italics = sequence that was varied (i.e., the first six amino acids after the initiation codon)
Italic = BssHII, MluI, or XbaI restriction site

TABLE 3

Final time point fermentation titers

| Heavy chain signal sequence (TIR)/ light chain signal sequence (TIR) | DsbA/C (+/−) | Relative full-length Ab titer* |
|---|---|---|
| STII (1)/STII (1) | − | 1.0 |
| STII (1)/STII (1) | + | 4.9 |
| STII (1)/PhoA (1) | − | 0.6 |
| STII (1)/PhoA (1) | + | 5.6 |
| STII (2)/STII (2) | + | 0.8 |
| MalE (1)/STII (1) | − | 0.4 |
| MalE (1)/PhoA (1) | − | 0.4 |
| MalE (1)/PhoA (1) | + | 1.5 |
| DsbA (1)/STII (1) | − | 1.4 |
| DsbA (1)/STII (1) | + | 3.3 |
| DsbA (1)/STII (2) | + | 3.6 |
| DsbA (2)/STII (1) | − | 0.9 |
| DsbA (1)/MalE (1) | − | 1.7 |
| DsbA (1)/MalE (1) | + | 10.1 |
| DsbA (1)/DsbA (1) | − | 1.9 |
| DsbA (1)/DsbA (1) | + | 12.7 |
| DsbA (2)/DsbA (2) | + | 10.6 |
| DsbA (1)/PhoA (1) | − | 1.9 |
| DsbA (1)/PhoA (1) | + | 10.0 |
| DsbA (2)/PhoA (1) | − | 1.5 |
| DsbA (2)/PhoA (1) | + | 6.7 |
| PhoA (1)/STII (1) | − | 0.3 |

*All samples normalized to the titer of the STII (1)/STII (1) sample, which comprised full length antibody expressed without chaperones DsbA and DsbC present.

Results/Discussion

We developed novel variant translational initiation region (TIR) signal peptide libraries (FIG. 2, Table 2) for signal peptides representing two of the major secretion pathways for transport across the inner-membrane in E. coli: sec (PhoA, MalE) and SRP (DsbA, STII). Each library comprises a panel of vectors with comprising variant TIRs of differing translational strengths, providing a means by which to readily adjust level of translation for a given protein of interest. The maltose-binding periplasmic protein (MalE) and alkaline phosphatase (PhoA) signal peptides direct translocation from the cytoplasm to the periplasm in a post-translational manner with the aid of the molecular motor SecA. The heat-stable enterotoxin II (stII) and thiol: disulfide interchange protein (dsbA) signal peptides direct translocation in a co-translational manner with aid from the signal recognition particle (SRP) (FIG. 1).

Figure 2:
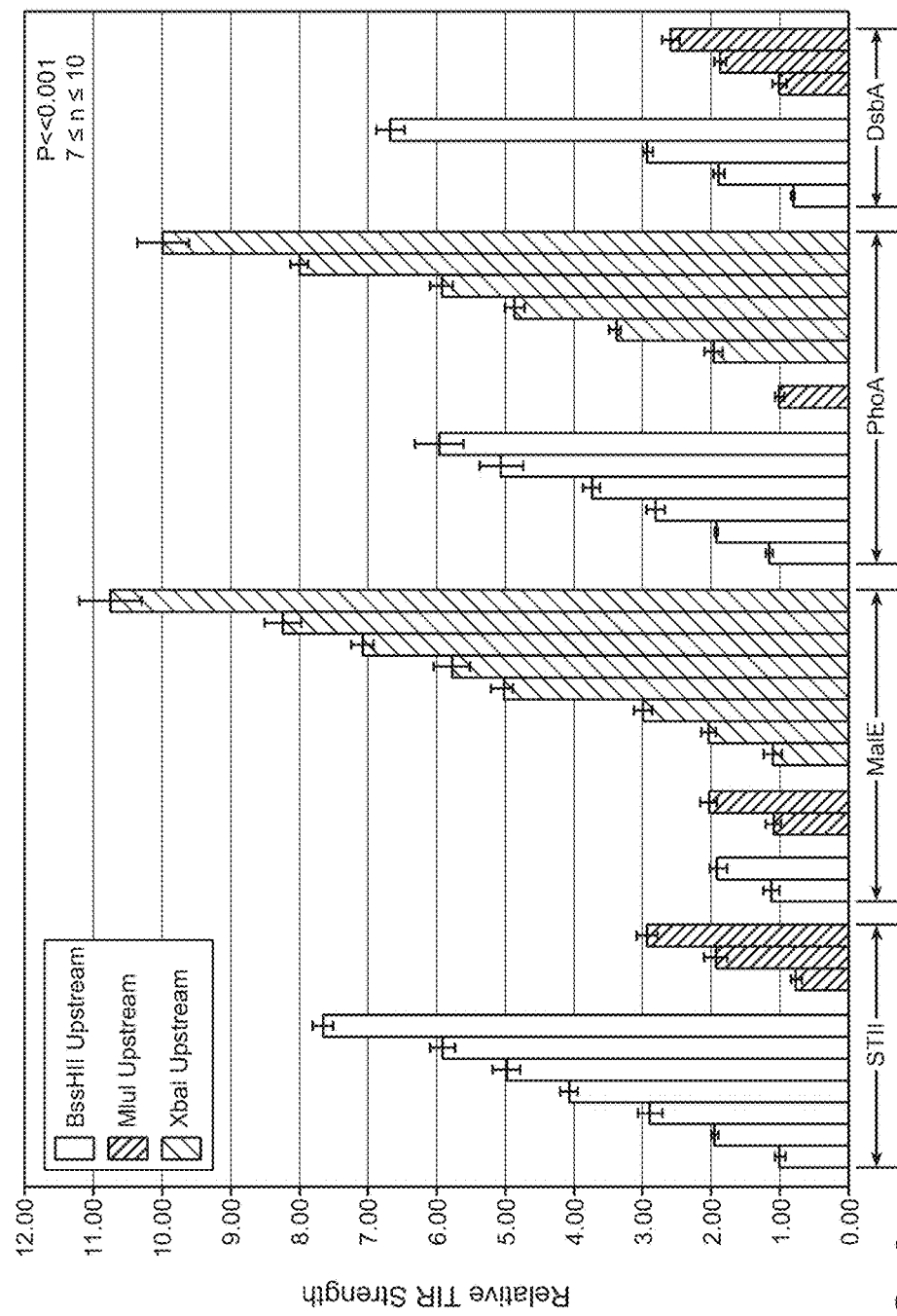
FIG. 2: Relative translocation initiation region strength of signal peptide variants. Normalized basal alkaline phosphatase activity of 27C7 cells carrying a vector with a fusion between either an STII, MalE, PhoA, or DsbA signal peptide and the mature domain of the *E. coli* alkaline phosphatase (BAP) gene. Each bar represents an individual culture incubated with the chromogenic substrate PNPP and enzymatic activity was determined as the absorbance of that culture at 410 nm less the absorbance of a culture carrying an empty vector (pBR322). Activities were normalized to the basal activity of 27C7 cells carrying the plasmid pPho41. White bars represent signal peptide variants with a BssHII restriction site at the −9 position relative to the first base pair of the initiation codon. Grey or striped bars represent an MluI or XbaI site at the −9 position, respectively. All activities are the mean of between seven and ten replicate experiments. Error bars are reported as the uncertainty in the mean with a 95% confidence limit. The differences in relative TIR strength between adjacent bars are all statistically significant ($P \ll 0.001$). Bars represent clones SH1.2, SH2.41, SH3.38, SH4.60, SH5.34, SH6.52, SH8.36, SL1.2, SL2.74, SL3.72, MH1.92, MH2.100, ML1.97, ML2.123, MX1.wt, MX2.15, MX3.12, MX5.37, MX6.4, MX7.25, MX8.13, MX11.34, PH1.70, PH2.64, PH3.wt, PH4.67, PH5.71, PH6.77, PL1.104, PX2.41, PX3.wt, PX5.53, PX6.15, PX8.24, PX10.23, DH1.48, DH2.wt, DH3.79, DH7.72, DL1.wt, DL2.3, DL3.37 (in order, from left to right).

During construction of the library, a BssHII, MluI, or XbaI restriction site was inserted nine base pairs (bps) upstream of the parental gene's initiation codon. Depending upon the type of restriction site present, different ranges of TIR strengths were observed (FIG. 2). In general, sequences bearing an MluI site displayed the smallest range of TIR strengths (~1-3), while a BssHII site upstream allowed for a moderate range of TIR strengths (~1-8), and an XbaI site the highest range (~1-11). These restriction sites present in the untranslated region are encompassed in the TIR (3). While it cannot be ruled out that higher TIR variants may exist for any of the signal peptide/restriction site combinations examined, these results appear to be representative of the mean TIR strengths of each signal peptide library examined.

A series of plasmids was constructed to illustrate the effect of translational level and signal peptide on secretion. In each case, the gene of interest was inserted downstream of the phoA promoter, trp Shine-Dalgarno and a signal sequence possessing a different relative TIR strength. Following transformation and induction of the phoA promoter at the shake flask scale, lysates from whole cells expressing the heterologous protein, the anti-c-met antibody clone 5D5.v2, were analyzed by SDS-PAGE. In these experiments, either heavy chain or light chain TIR was varied, with the corresponding light chain or heavy chain, respectively, kept invariant.

Figures 3A, 3B:
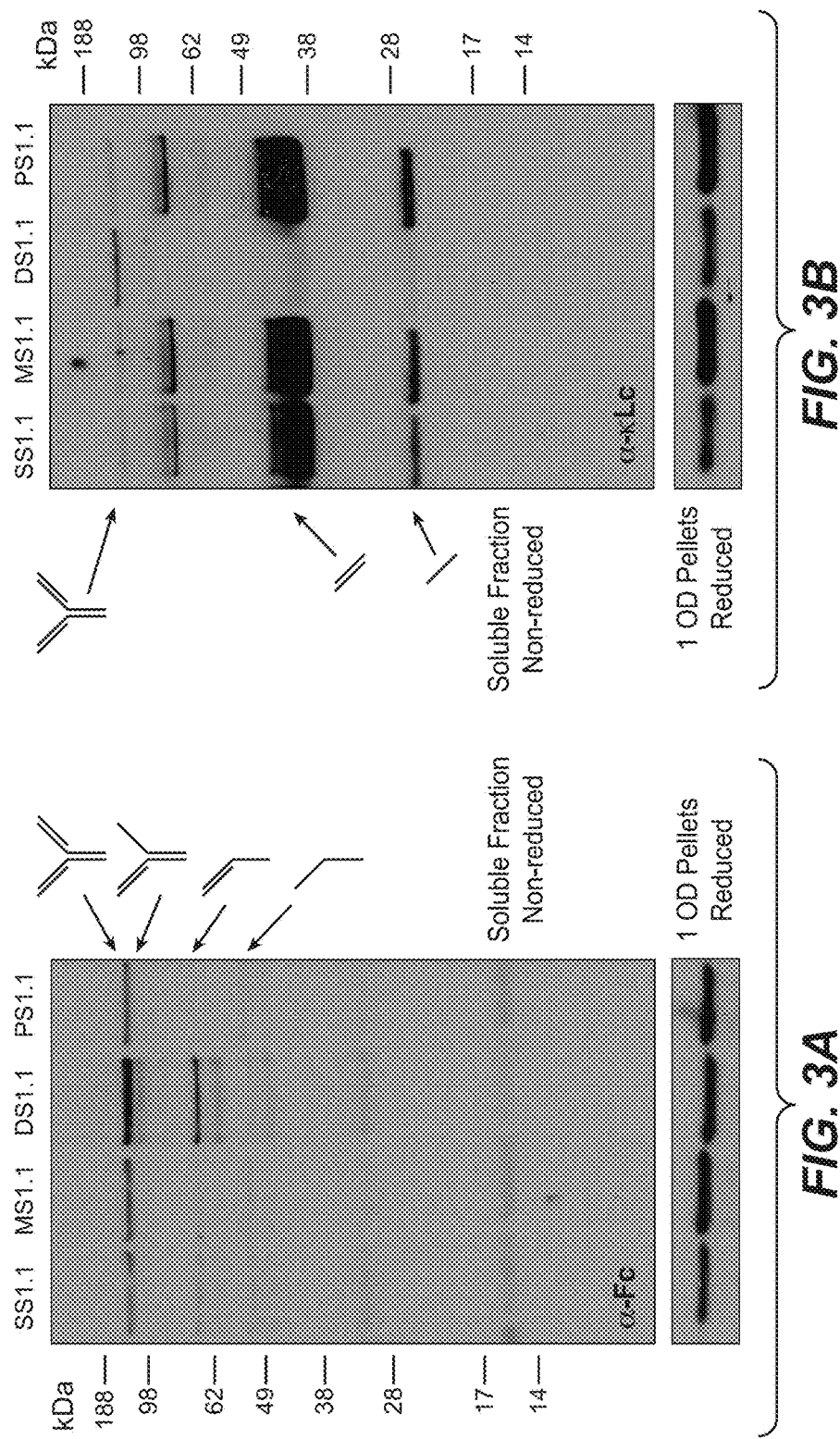
FIGS. 3A & 3B: Monitoring assembly of antibody species with heavy chain signal peptide manipulation. 64B4 cells were grown in 25 mL of C.R.A.P. phosphate-limiting media for 24 hours and soluble fractions as well at total protein pellets normalized by optical density (OD) were prepared for SDS-PAGE analysis.

FIGS. 3A & 3B show the results of heavy chain signal peptide manipulation. When probed with an α-Fc specific antibody, the ssDsbA-heavy chain TIR one variant gave a clear increase in full-length antibody (FL-Ab), as well as heavy-light (HL) dimer and heavy-heavy-light (HHL) species, over the other signal peptide variants (FIG. 3A, top blot). An examination of the total heavy chain from these samples revealed relatively similar levels between all signal peptide fusions examined (FIG. 3A, bottom blot). When light chain was visualized with an α-κLc antibody, similar results were obtained, with the ssDsbA-heavy chain TIR one variant again displaying the highest level of FL-Ab (FIG. 3B, top blot). Strikingly, the DsbA TIR one-heavy chain fusion sample lacked the lower mass species—the predicted light-light (LL) dimer and free light chain—seen in the other samples. Generally, in the case where the post-translational signals (MalE, PhoA) is fused to the heavy chain there appear to be more expressed total light chain than in the cases of the co-translational (STII, DsbA) signal peptide fusions (FIG. 3B, bottom blot). In general, the following hierarchy was observed with respect to the signal peptide fused to the heavy chain and full length antibody production: DsbA>STII>MalE>PhoA. Notably, the DsbA variant TIR resulted in increased expression (e.g., of full length antibody) compared to STII variant TIR, even though the relative TIR strength did not change (i.e., both TIRs were strength one).

Figure 4:
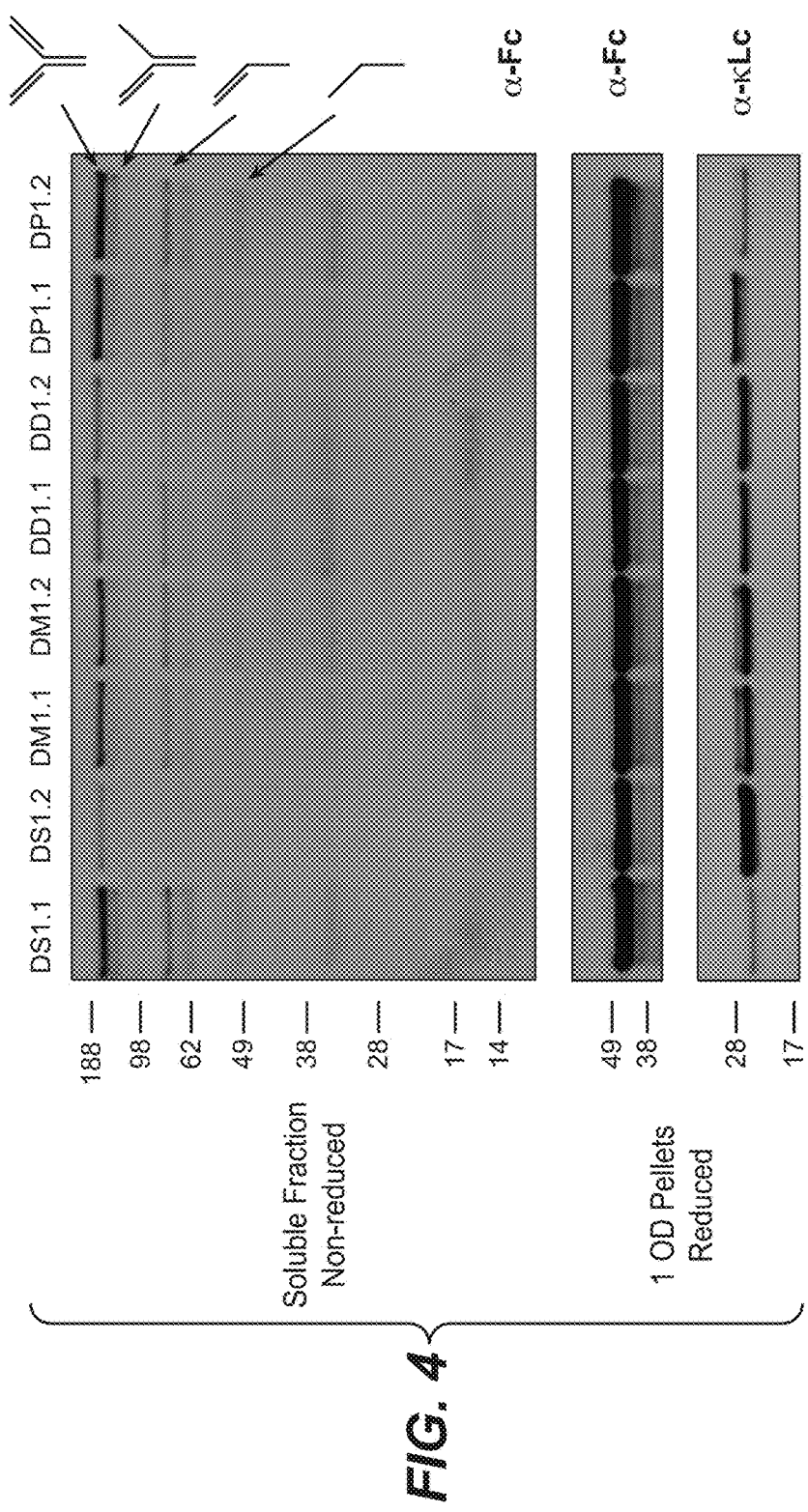
FIG. 4: Monitoring assembly of antibody species with light chain signal peptide manipulation. 64B4 cells were grown in 25 mL of C.R.A.P. phosphate-limiting media for 24 hours and soluble fractions as well at total protein pellets normalized by optical density (OD) were prepared for SDS-PAGE analysis. Samples from cells carrying the plasmid pBR-DS-5D5-1.1 (DS1.1), pBR-DS-5D5-1.2 (DS1.2), pBR-DM-5D5-1.1 (DM1.1), pBR-DM-5D5-1.2 (DM1.2), pBR-DD-5D5-1.1 (DD1.1), pBR-DD-5D5-1.2 (DD1.2), pBR-DP-5D5-1.1 (DP1.1), or pBR-DP-5D5-1.2 were separated by SDS-PAGE gel electrophoresis (mass in kDa indicated at the left side), transferred to nitrocellulose, and probed for the presence of heavy or light chain-containing species with an α-Fc or α-κLc specific antibody, respectively, as indicated along the right side of the images. Soluble samples (top blot) consisted of the putatively identified bands corresponding to (from top to bottom): full-length antibody, heavy-heavy-light (HHL), heavy-light (HL) dimer or free heavy chain. Normalized, total protein samples (middle blot, bottom) were reduced with 0.2 M DTT to disrupt disulfide bond structure and each individual lane migrated to a single band with an apparent mass of ~49 kDa when probed with an α-Fc antibody. When probed with an α-κLc specific antibody, all lanes migrated to a single or double band with an apparent mass of either ~25 kDa or ~27 kDa and ~25 kDa. Abbreviations: S=signal sequence STII M=signal sequence MalE D=signal sequence DsbA P=signal sequence PhoA. XX#.# (e.g. DS1.1) refers to heavy chain signal sequence, light chain signal sequence, heavy chain TIR, light chain TIR used in the experiment.

FIG. 4 shows the results of light chain signal peptide manipulation. Changing the light chain signal peptide from an STII TIR one variant to either a PhoA TIR one or two variant produced a noticeable increase in FL-Ab titer (FIG. 4, top blot). Modification of the signal peptide fused to the light chain did not appear to effect the total amount of heavy chain expressed (FIG. 4, middle blot), but did significantly alter the total amount of light chain present, with the largest accumulation of processed light chain appearing in samples with a STII or DsbA TIR variant two fused to the light chain (FIG. 4, bottom blot). When fused to the post-translational signal peptides, two bands were observed in the total light chain samples, indicative of unprocessed light chain. In general, the following hierarchy was observed with respect to signal peptide fusions to the light chain and full length antibody production: PhoA≥MalE>STII>DsbA.

Figure 5:
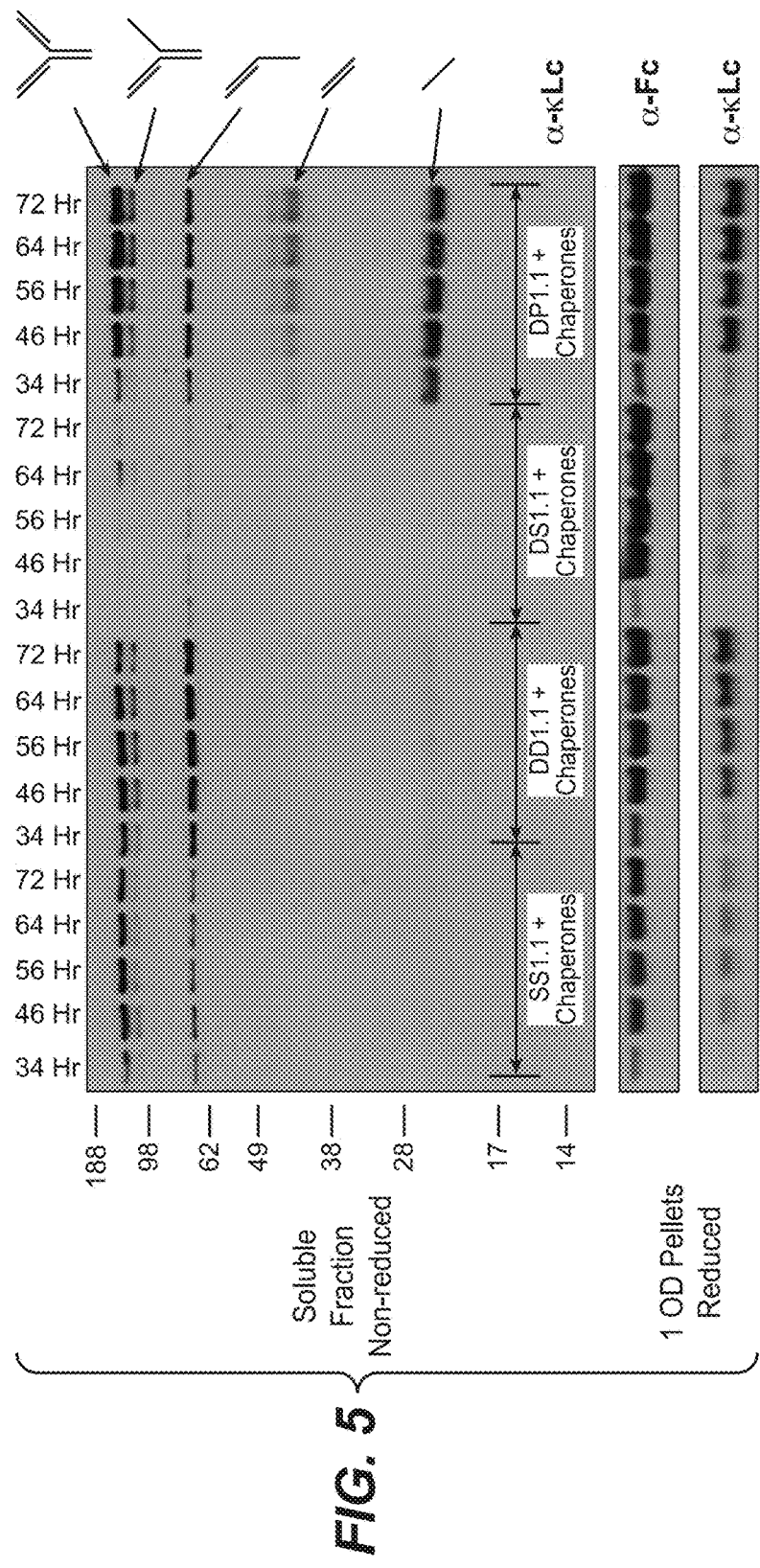
FIG. 5: Monitoring assembly of antibody species over time from 10-L fermentations. 64B4 cells were grown to a high cell density in a 10-L fermentation for three days with samples taken at regular time intervals (time sample taken above each lane in hours past inoculation) from which soluble fractions as well at total protein pellets normalized by optical density (OD) were prepared for SDS-PAGE analysis. Samples from cells carrying the plasmid pBR-SS-5D5-1.1 co-expressing the chaperone-bearing plasmid pJJ247 (SS1.1+Chaperones), pBR-DD-5D5-1.1 with pJJ247 (DD1.1+Chaperones), pBR-DS-5D5-1.1 with pJJ247 (DM1.1+Chaperones), or pBR-DP-5D5-1.1 with pJJ247 (DP1.1+Chaperones) were separated by SDS-PAGE gel electrophoresis (mass in kDa indicated at the left side), transferred to nitrocellulose, and probed for the presence of heavy or light chain-containing species with an α-Fc or α-κLc specific antibody, respectively, as indicated along the right side of the images. Soluble samples (top blot) consisted of the putatively identified bands corresponding to (from top to bottom): full-length antibody, heavy-heavy-light (HHL), heavy-light (HL) dimer, light-light (LL) dimer, or free light chain. Normalized, total protein samples (middle blot, bottom) were reduced with 0.2 mM DTT to disrupt disulfide bond structure and each individual lane migrated to a single band with an apparent mass of ~49 kDa when probed with an α-Fc. When probed with an α-κLc specific antibody, all lanes migrated to a single band with an apparent mass of either ~25 kDa. Abbreviations: S=signal sequence STII M=signal sequence MalE D=signal sequence DsbA P=signal sequence PhoA. XX#.# (e.g. DS1.1) refers to heavy chain signal sequence, light chain signal sequence, heavy chain TIR, light chain TIR used in the experiment.

Monitoring assembly of antibody species over time from 10-L fermentations revealed similar results to the shake flask experiments shown in FIGS. 3 and 4. The highest amount of FL-Ab was observed from samples with a DsbA-derived TIR variant fused to the heavy chain and either a DsbA- or PhoA-derived signal peptide fused to the light chain (FIG. 5, top blot). These samples also displayed more HHL and HL dimer species than did the STII TIR one heavy chain fusion. Additionally, LL dimer and free light chain was readily visible in samples with the PhoA TIR one signal peptide fused to the light chain. Examination of reduced total protein samples revealed that the DsbA signal peptide fusion resulted in more total heavy chain than the STII fusion under the expression inducing conditions of the fermentation (FIG. 5, middle blot). Similarly for the light chain signal peptide fusions, a higher accumulation of light chain was observed with the DsbA TIR one signal peptide fusions than the STII TIR one (FIG. 5, bottom blot). However, the highest accumulation of light chain was seen with the PhoA TIR one signal peptide fusion. The two bands seen in total light chain samples taken from the shake flasks appears as only one band in fermentation samples, indicative of light chain being more efficiently processed during 10-L fermentation.

Figure 6:
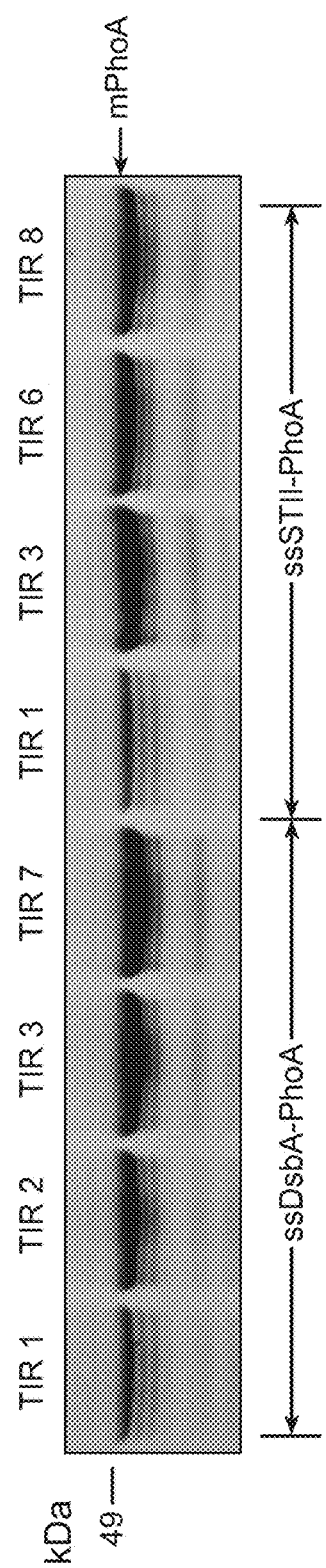
FIG. 6: Accumulation of mature PhoA under inducing conditions. 27C7 cells were grown in 25-mL of C.R.A.P. phosphate-limiting media for 24 hours and soluble fractions were normalized by optical density (OD) and prepared for SDS-PAGE analysis. The mature domain of the *E. coli* phoA gene was fused to the indicated DsbA or STII (bottom) TIR variants (top). Gel was visualized for the presence of protein by Commassie blue staining A putatively identified band corresponding to the mature domain of PhoA (right) appeared at a mass of ~47 kDa (mass indicated at left side).

We fused different signal peptides to the mature domain of the *E. coli* phoA gene (mPhoA) to further examine the differences in total light or heavy chain expression levels when fused to either STII- or DsbA-derived TIR variants and expressed in shake flask cultures under inducing conditions. Similar effects on total light and heavy chain expression levels were observed (FIG. 6). When protein expression was induced, expression of mPhoA showed a concomitant rise with increased TIR strength for the DsbA signal peptide fusions, up to a TIR strength of seven (the highest TIR strength used in this study). A similar increase in mPhoA expression with TIR strength increase was observed for the STII signal peptide fusions up to a TIR strength of six or eight was reached, whereby the amount of mPhoA appears to decrease compared to the mPhoA present in the STII TIR three sample. Strikingly, more heavy and light chain was produced using a DsbA strength one TIR than using a STII strength one TIR, and STII-driven translocation of PhoA reached a maximum amount at a lower total protein concentration than did Dba-drive translocation of PhoA. Moreover, changing TIR sequence from STII to DsbA increased the dynamic range of TIR effect.

Samples from 10-L fermentations were analyzed for antibody titers using a Protein-L-based HPLC assay (Table 3). The HPLC data were in good agreement with qualitative titer levels revealed by Western blot analysis (FIGS. 3, 4). When the heavy chain signal sequence was changed from a STII-derived TIR variant to a Dsb-derived TIR variant, FL-Ab titers increased ~40-90%. The highest titers were produced when a DsbA one heavy chain fusion was paired with a light chain fused to either the DsbA, MalE, or PhoA TIR one signal peptides. Highest titers were generated when the light chain was fused to the MalE or PhoA TIR signal peptides.

By contrast, FL-Ab titer fell when a post-translational signal peptide was fused to the heavy chain, with a PhoA TIR one and MalE TIR one signal peptide fusion showing a 70% and 60% drop in titer, respectively. We concluded that heavy chain expression was optimized when a co-translational signal peptide (e.g., DsbA) was used to drive translation.

We tested the effect of chaperone overexpression. The overexpression of chaperones DsbA and DsbC (sometimes termed DsbA/C herein) enhanced the benefits of DsbA signal peptide fused to the heavy chain and DsbA, PhoA, or MalE signals fused to the light chain. When compared to expression of FL-Ab by a STII TIR one signal fused to the heavy and light chains (SS1.1+Chaperones), an approximate 2- to 2.5-fold increase in FL-Ab titer was seen with a DsbA TIR one-heavy chain fusion coupled with a MalE, PhoA, or DsbA TIR one light chain fusion.

We examined the relationship between the signal peptide fused to the light chain and heavy chain of an antibody and final antibody titers. Fully-assembled antibody (FL-Ab) titers were highest when a co-translational (e.g., DsbA or STII) signal peptide was fused to the N-terminus of the heavy chain, with the DsbA-derived TIR variants resulting in the maximum observed FL-Ab yields. Thus, DsbA TIR variants may allow for higher translation levels of passenger protein than do STII TIR variants under inducing conditions, thereby resulting in higher expression levels of processed passenger protein. By contrast, antibody titers dramatically fell when either post-translational signal peptide (i.e., MalE or PhoA) was fused to the heavy chain\. This effect may be due to proteolysis or may be due to a different folding pathway followed by the heavy chain (6). An examination of total heavy chain levels from samples expressing either a PhoA or MalE TIR one signal peptide fused to the heavy chain revealed a slight shift in apparent mass, potentially due to the presence of unprocessed heavy chain (FIG. 3A, bottom blot).

Fusion of post-translational signal peptide MalE-derived or PhoA-derived TIR variants to the light chain resulted in a large accumulation of processed light chain and increased antibody titers over STII-mediated translocation during 10 L fermentation (FIG. 5, bottom blot). Increased yields of both light chain as well as FL-Ab were also observed when the light chain was translocated by DsbA TIR variants as compared with light chain translocated by STII TIR variants. However, the amount of total light chain expressed from the DsbA TIR one variant was not a great at that from the PhoA or MalE TIR one variants. Interestingly, analysis of samples taken over time from 10-L fermentations indicate that FL-Ab titers from runs with the light chain fused to either MalE, DsbA, or PhoA TIR variants continued to rise over time while fusions to STII TIR variants reached not only a lower maximum titer, but reached that titer level at a much earlier time point (FIG. 5, top blot). Thus, these data suggest that the light chain may be effectively translocated in either a co- or post-translational manner while the heavy chain requires co-translational translocation for peak expression.

Expression of a one-armed anti-c-met antibody: We evaluated the relationship between the signal peptide fused to the light chain, heavy chain and Fc of a one-armed antibody, and the final antibody titers. Plasmids were constructed using STII signal sequences with TIRs of 1 for light chain, heavy chain, and the Fc polypeptide, using the PhoA signal sequence with a TIR of 1 (SEQ ID NO: 29) for light chain and DsbA signal sequence with a TIR of 1 (SEQ ID NO: 40) for heavy chain and the Fc fragment; and using the PhoA signal sequence with a TIR of 1 for light chain and the Fc fragment and the DsbA signal sequence with a TIR of 1 for HC. Relative titer numbers were from end of run samples and were measured using the Protein L-reversed phase HPLC assay described above. The relative titer values were normalized to the titer for the case in the first row of Table 4—STII signal sequences and TIR=1 for LC, HC, and Fc without the co-expression of DsbA/C.

The results are shown in Table 4. One-armed antibody relative titers were highest when a co-translational (e.g., DsbA) signal peptide was fused to the N-terminus of the heavy chain, post-translational (e.g., PhoA) signal peptide was fused to the N-terminus of the light chain, and a post-translational (e.g., PhoA) signal peptide was fused to the Fc region, and expression was in the presence of DsbA/C. In general, the following hierarchy was observed with respect to the signal peptide fused to the light chain, heavy chain and Fc fragment, and one-armed antibody expression in the presence of DsbA/C: P.D.D>P.D.P.>S.S.S. Expression levels in the absence of DsbA/C were similar in all tested samples, in which most of the antibody secreted to the periplasm was aggregated. Co-expression of disulfide bond chaperones increased the folded antibody produced, thus revealing the increased antibody expression realized by TIR optimization.

TABLE 4

Expression of monovalent one-armed anti-c-met antibody MetMAb).

| Plasmid | LC, HC, Fc | DsbA/C | Relative Titer |
|---|---|---|---|
| pxCM11H.v2.H.Fc.1.K.2192 | STII TIR 1 for Lc, Hc, and Fc | − | 1.0 |
| pxCM11H.v2.H.Fc.1.K.2192 | STII TIR 1 for Lc, Hc, and Fc | + | 1.7 |
| pPDD.111.MetMAb | PhoA TIR 1 for Lc, DsbA TIR 1 for Hcand Fc | − | 1.0 |
| pPDD.111.MetMAb | PhoA TIR 1 for Lc, DsbA TIR 1 for Hc and Fc | + | 3.8 |
| pPDP.111.MetMAb | PhoA TIR 1 for Lc, DsbA TIR 1 for Hc, PhoA TIR for Fc | − | 0.7 |
| pPDP.111.MetMAb | PhoA TIR 1 for Lc, DsbA TIR 1 for Hc, PhoA TIR for Fc | + | 2.5 |

Abbreviations: D=signal sequence DsbA P=signal sequence PhoA. XXX#.#.# (e.g. PDP.111) refers to light chain signal sequence, heavy chain signal sequence, Fc signal sequence, light chain TIR, heavy chain TIR, Fc TIR used in the experiment.

In summary, this technology offers a novel means for increasing folded antibody yields, for example, in *E. coli* through manipulation of light chain and heavy chain expression via the selection from a new array of TIR variants and further by the use of co- or post-translational signal sequences for light chain and co-translational signal sequence for heavy chain. Improved expression of one-armed antibodies comprising a heavy chain, a light chain and a Fc region was also accomplished using the novel TIR variants disclosed herein, and further by the use of co- or post-translational signal sequences for light chain, co-translational signal sequence for heavy chain, and co- or post-translational signal sequence for Fc polypeptide resulted. The utility of this method appears to be broadly applicable to a wide-range of antibodies (for example, bispecific antibodies comprising knob and hole mutations), antibody derivatives and bacterial-based recombinant protein production as a whole.

PARTIAL REFERENCE LIST

1. Simmons, L. C., Reilly, D., Klimowski, L., Raju, T. S., Meng, G., Sims, P., Hong, K., Shields, R. L., Damico, L. A., Rancatore, P., and Yansura, D. G. (2002) Journal of immunological methods 263(1-2), 133-147

2. Stemmer, W. P., Morris, S. K., Kautzer, C. R., and Wilson, B. S. (1993) Gene 123(1), 1-7

3. Simmons, L. C., and Yansura, D. G. (1996) Nature biotechnology 14(5), 629-634

4. Le Calvez, H., Green, J. M., and Baty, D. (1996) Gene 170(1), 51-55

5. Jackson, R. W., and DeMoss, J. A. (1965) Journal of bacteriology 90(5), 1420-1425

6. Kadokura, H., and Beckwith, J. (2009) Cell 138(6), 1164-1173

Although the forgoing refers to particular embodiments, it will be understood that the present invention is not so limited. It will occur to those ordinary skilled in the art that various modifications may be made to the disclosed embodiments without diverting from the overall concept of the invention. All such modifications are intended to be within the scope of the present invention.

What is claimed is:

1. A method of making an antibody, said method comprising culturing a host cell comprising a polynucleotide comprising (1) a first inducible promoter operably linked to a first TIR operably linked to a polynucleotide encoding an antibody heavy chain, wherein the first TIR comprises a DsbA variant co-translational prokaryotic secretion signal sequence; and (2) a second inducible promoter operably linked to a second TIR operably linked to a polynucleotide encoding an antibody light chain, wherein the second TIR comprises a co-translational or post-translational prokaryotic secretion signal sequence, inducing expression of the antibody heavy chain and antibody light chain, and lysing the host cell to form a whole cell lysate, whereby upon expression of the antibody heavy chain and antibody light chain in the host cell and lysis of the host cell, at least 50% by molar ratio of the heavy and light chains in the whole cell lysate are folded and assembled to form a biologically active antibody, wherein the host cell is an *E. coli* cell.

2. The method of claim 1, wherein the first translation initiation region comprises sequence of one of SEQ ID NOs: 36-42.

3. The method of claim 1, wherein the second translation initiation region comprises a STII, DsbA, MalE or PhoA variant signal sequence.

4. The method of claim 3, wherein the second translation initiation region comprises a PhoA or MalE variant signal sequence.

5. The method of claim 3, wherein the second translation initiation region comprises sequence of one of SEQ ID NOs 1-42.

6. The method of claim 3, wherein the second translation initiation region comprises sequence of one of SEQ ID Nos. 1-14, 16-24, 26-39, and 41-42.

7. The method of claim 1, wherein the polynucleotide encoding an antibody further comprises (3) a third inducible promoter operably linked to a third translation initiation region operably linked to a polynucleotide encoding a Fc polypeptide, wherein the third translation initiation region comprises a co-translational or post-translational prokaryotic signal sequence.

8. The method of claim 7, wherein the third translation initiation region comprises a PhoA or DsbA variant signal sequence.

9. The method of claim 1, wherein the relative translation strength of the first translation initiation region to the second translational initiation region is about one or two.

10. The method of claim 9, wherein the relative translation strength of the first translation initiation region to the second translational initiation region is about one.

11. The method of claim 1, wherein the first and second inducible promoters are each prokaryotic promoters independently selected from the group consisting of phoA, tac, lpp, lac-lpp, lac, ara, and T7 promoter.

12. The method of claim 1, wherein the antibody is a monoclonal antibody.

13. The method of claim 12, wherein the antibody is a chimeric antibody, an affinity matured antibody, a bispecific antibody, humanized antibody, an antibody fragment or a human antibody.

14. The method of claim 13, wherein the antibody fragment is a one-armed antibody.

15. The method of claim 13 or 14, wherein the antibody binds c-met.

16. The method of claim 15, wherein the anti-c-met antibody comprises (a) a first polypeptide comprising a heavy chain variable domain having the sequence: EVQLVESGGGLVQPGGSLRLSCAASGYTFTSYWLHWVRQAPGKGLEWVGMIDPSNSD TRFNPNFKDRFTISADTSKNTAYLQMNSLRAEDTAVYYCATYRSYVTPLDYWGQGTLV TVSS (SEQ ID NO: 43), CHI sequence, and a first Fc polypeptide; (b) a second polypeptide comprising a light chain variable domain having the sequence: DIQMTQSPSSLSASVGDRVTITCKSSQSLLYTSSQKNYLAWYQQKPGKAPKLLIYWAST RESGVPSRFSGSGSGTDFTLTISSLQPEDFATYYCQQYYAYPWTFGQGTKVEIKR (SEQ ID NO:44), and CLI sequence; and (c) a third polypeptide comprising a second Fc polypeptide, wherein the heavy chain variable domain and the light chain variable domain are present as a complex and form a single antigen binding arm, wherein the first and second Fc polypeptides are present in a complex and form a Fc region that increases stability of said antibody fragment compared to a Fab molecule comprising said antigen binding arm.

17. The method of claim 1, wherein the *E. coli* is of a strain deficient in endogenous protease activities.

18. The method of claim 1, wherein the genotype of the *E. coli* lacks degP and prc genes and harbors a mutant spr gene.

19. The method of claim 1, wherein the method further comprises recovering the antibody from the whole cell lysate.

20. The method of claim 19, wherein the method further comprises combining the recovered antibody with a pharmaceutically acceptable carrier or excipient to prepare a pharmaceutical formulation comprising the antibody.

21. The method of claim 3, wherein the second translation initiation region comprises sequence of one of SEQ ID NOs. 1, 2, 8, 9, 11, 13, 29, 36, 37, and 40.

22. The method of claim 7, wherein the third translation initiation region comprises sequence of one of SEQ ID NOs. 1-42.

23. The method of claim 7, wherein the relative translation strength of the first, second and third translation initiation regions is about one.

24. The method of claim 1, wherein the host cell further comprises a polynucleotide encoding at least one prokaryotic polypeptide selected from the group consisting of DsbA, DsbC, DsbG and FkpA.

25. The method of claim 24, wherein the polynucleotide encodes both DsbA and DsbC.

26. The method of claim 3, wherein the second translation initiation region comprises a STII variant signal sequence.

27. The method of claim 3, wherein the second translation initiation region comprises a DsbA variant signal sequence.

28. The method of claim 3, wherein the second translation initiation region comprises a MalE variant signal sequence.

29. The method of claim 3, wherein the second translation initiation region comprises a PhoA variant signal sequence.

30. The method of claim 26, wherein the relative translation strength of the first translation initiation region to the second translational initiation region is about one or two.

31. The method of claim 27, wherein the relative translation strength of the first translation initiation region to the second translational initiation region is about one or two.

32. The method of claim 28, wherein the relative translation strength of the first translation initiation region to the second translational initiation region is about one or two.

33. The method of claim 29, wherein the relative translation strength of the first translation initiation region to the second translational initiation region is about one or two.

34. The method of claim 26, wherein the relative translation strength of the first translation initiation region to the second translation initiation region is about one.

35. The method of claim 27, wherein the relative translation strength of the first translation initiation region to the second translation initiation region is about one.

36. The method of claim 28, wherein the relative translation strength of the first translation initiation region to the second translation initiation region is about one.

37. The method of claim 29, wherein the relative translation strength of the first translation initiation region to the second translation initiation region is about one.

38. The method of claim 11, wherein the first and/or second inducible promoter is a phoA promoter.

39. The method of claim 11, wherein the first and/or second inducible promoter is a tac promoter.

40. The method of claim 11, wherein the first and/or second inducible promoter is a lpp promoter.

41. The method of claim 11, wherein the first and/or second inducible promoter is a lac-lpp promoter.

42. The method of claim 11, wherein the first and/or second inducible promoter is a lac promoter.

43. The method of claim 11, wherein the first and/or second inducible promoter is an ara promoter.

44. The method of claim 11, wherein the first and/or second inducible promoter is a T7 promoter.

45. The method of claim 26, wherein the first and/or second inducible promoter is a phoA promoter.

46. The method of claim 26, wherein the first and/or second inducible promoter is a tac promoter.

47. The method of claim 26, wherein the first and/or second inducible promoter is a lpp promoter.

48. The method of claim 26, wherein the first and/or second inducible promoter is a lac-lpp promoter.

49. The method of claim 26, wherein the first and/or second inducible promoter is a lac promoter.

50. The method of claim 26, wherein the first and/or second inducible promoter is an ara promoter.

51. The method of claim 26, wherein the first and/or second inducible promoter is a T7 promoter.

52. The method of claim 27, wherein the first and/or second inducible promoter is a phoA promoter.

53. The method of claim 27, wherein the first and/or second inducible promoter is a tac promoter.

54. The method of claim 27, wherein the first and/or second inducible promoter is a lpp promoter.

55. The method of claim 27, wherein the first and/or second inducible promoter is a lac-lpp promoter.

56. The method of claim 27, wherein the first and/or second inducible promoter is a lac promoter.

57. The method of claim 27, wherein the first and/or second inducible promoter is an ara promoter.

58. The method of claim 27, wherein the first and/or second inducible promoter is a T7 promoter.

59. The method of claim 28, wherein the first and/or second inducible promoter is a phoA promoter.

60. The method of claim 28, wherein the first and/or second inducible promoter is a tac promoter.

61. The method of claim 28, wherein the first and/or second inducible promoter is a lpp promoter.

62. The method of claim 28, wherein the first and/or second inducible promoter is a lac-lpp promoter.
63. The method of claim 28, wherein the first and/or second inducible promoter is a lac promoter.
64. The method of claim 28, wherein the first and/or second inducible promoter is an ara promoter.
65. The method of claim 28, wherein the first and/or second inducible promoter is a T7 promoter.
66. The method of claim 29, wherein the first and/or second inducible promoter is a phoA promoter.
67. The method of claim 29, wherein the first and/or second inducible promoter is a tac promoter.
68. The method of claim 29, wherein the first and/or second inducible promoter is a lpp promoter.
69. The method of claim 29, wherein the first and/or second inducible promoter is a lac-lpp promoter.
70. The method of claim 29, wherein the first and/or second inducible promoter is a lac promoter.
71. The method of claim 29, wherein the first and/or second inducible promoter is an ara promoter.
72. The method of claim 29, wherein the first and/or second inducible promoter is a T7 promoter.
73. The method of claim 30, wherein the first and/or second inducible promoter is a phoA promoter.
74. The method of claim 30, wherein the first and/or second inducible promoter is a tac promoter.
75. The method of claim 30, wherein the first and/or second inducible promoter is a lpp promoter.
76. The method of claim 30, wherein the first and/or second inducible promoter is a lac-lpp promoter.
77. The method of claim 30, wherein the first and/or second inducible promoter is a lac promoter.
78. The method of claim 30, wherein the first and/or second inducible promoter is an ara promoter.
79. The method of claim 30, wherein the first and/or second inducible promoter is a T7 promoter.
80. The method of claim 31, wherein the first and/or second inducible promoter is a phoA promoter.
81. The method of claim 31, wherein the first and/or second inducible promoter is a tac promoter.
82. The method of claim 31, wherein the first and/or second inducible promoter is a lpp promoter.
83. The method of claim 31, wherein the first and/or second inducible promoter is a lac-lpp promoter.
84. The method of claim 31, wherein the first and/or second inducible promoter is a lac promoter.
85. The method of claim 31, wherein the first and/or second inducible promoter is an ara promoter.
86. The method of claim 31, wherein the first and/or second inducible promoter is a T7 promoter.
87. The method of claim 32, wherein the first and/or second inducible promoter is a phoA promoter.
88. The method of claim 32, wherein the first and/or second inducible promoter is a tac promoter.
89. The method of claim 32, wherein the first and/or second inducible promoter is a lpp promoter.
90. The method of claim 32, wherein the first and/or second inducible promoter is a lac-lpp promoter.
91. The method of claim 32, wherein the first and/or second inducible promoter is a lac promoter.
92. The method of claim 32, wherein the first and/or second inducible promoter is an ara promoter.
93. The method of claim 32, wherein the first and/or second inducible promoter is a T7 promoter.
94. The method of claim 33, wherein the first and/or second inducible promoter is a phoA promoter.
95. The method of claim 33, wherein the first and/or second inducible promoter is a tac promoter.
96. The method of claim 33, wherein the first and/or second inducible promoter is a lpp promoter.
97. The method of claim 33, wherein the first and/or second inducible promoter is a lac-lpp promoter.
98. The method of claim 33, wherein the first and/or second inducible promoter is a lac promoter.
99. The method of claim 33, wherein the first and/or second inducible promoter is an ara promoter.
100. The method of claim 33, wherein the first and/or second inducible promoter is a T7 promoter.
101. The method of claim 34, wherein the first and/or second inducible promoter is a phoA promoter.
102. The method of claim 34, wherein the first and/or second inducible promoter is a tac promoter.
103. The method of claim 34, wherein the first and/or second inducible promoter is a lpp promoter.
104. The method of claim 34, wherein the first and/or second inducible promoter is a lac-lpp promoter.
105. The method of claim 34, wherein the first and/or second inducible promoter is a lac promoter.
106. The method of claim 34, wherein the first and/or second inducible promoter is an ara promoter.
107. The method of claim 34, wherein the first and/or second inducible promoter is a T7 promoter.
108. The method of claim 35, wherein the first and/or second inducible promoter is a phoA promoter.
109. The method of claim 35, wherein the first and/or second inducible promoter is a tac promoter.
110. The method of claim 35, wherein the first and/or second inducible promoter is a lpp promoter.
111. The method of claim 35, wherein the first and/or second inducible promoter is a lac-lpp promoter.
112. The method of claim 35, wherein the first and/or second inducible promoter is a lac promoter.
113. The method of claim 35, wherein the first and/or second inducible promoter is an ara promoter.
114. The method of claim 35, wherein the first and/or second inducible promoter is a T7 promoter.
115. The method of claim 36, wherein the first and/or second inducible promoter is a phoA promoter.
116. The method of claim 36, wherein the first and/or second inducible promoter is a tac promoter.
117. The method of claim 36, wherein the first and/or second inducible promoter is a lpp promoter.
118. The method of claim 36, wherein the first and/or second inducible promoter is a lac-lpp promoter.
119. The method of claim 36, wherein the first and/or second inducible promoter is a lac promoter.
120. The method of claim 36, wherein the first and/or second inducible promoter is an ara promoter.
121. The method of claim 36, wherein the first and/or second inducible promoter is a T7 promoter.
122. The method of claim 37, wherein the first and/or second inducible promoter is a phoA promoter.
123. The method of claim 37, wherein the first and/or second inducible promoter is a tac promoter.
124. The method of claim 37, wherein the first and/or second inducible promoter is a lpp promoter.
125. The method of claim 37, wherein the first and/or second inducible promoter is a lac-lpp promoter.
126. The method of claim 37, wherein the first and/or second inducible promoter is a lac promoter.
127. The method of claim 37, wherein the first and/or second inducible promoter is an ara promoter.

128. The method of claim 37, wherein the first and/or second inducible promoter is a T7 promoter.

129. The method of claim 26, wherein the method further comprises recovering the antibody from the whole cell lysate.

130. The method of claim 27, wherein the method further comprises recovering the antibody from the whole cell lysate.

131. The method of claim 28, wherein the method further comprises recovering the antibody from the whole cell lysate.

132. The method of claim 29, wherein the method further comprises recovering the antibody from the whole cell lysate.

133. The method of claim 9, wherein the method further comprises recovering the antibody from the whole cell lysate.

134. The method of claim 10, wherein the method further comprises recovering the antibody from the whole cell lysate.

135. The method of claim 11, wherein the method further comprises recovering the antibody from the whole cell lysate.

136. The method of claim 129, wherein the method further comprises combining the recovered antibody with a pharmaceutically acceptable carrier or excipient to prepare a pharmaceutical formulation comprising the antibody.

137. The method of claim 130, wherein the method further comprises combining the recovered antibody with a pharmaceutically acceptable carrier or excipient to prepare a pharmaceutical formulation comprising the antibody.

138. The method of claim 131, wherein the method further comprises combining the recovered antibody with a pharmaceutically acceptable carrier or excipient to prepare a pharmaceutical formulation comprising the antibody.

139. The method of claim 132, wherein the method further comprises combining the recovered antibody with a pharmaceutically acceptable carrier or excipient to prepare a pharmaceutical formulation comprising the antibody.

140. The method of claim 133, wherein the method further comprises combining the recovered antibody with a pharmaceutically acceptable carrier or excipient to prepare a pharmaceutical formulation comprising the antibody.

141. The method of claim 134, wherein the method further comprises combining the recovered antibody with a pharmaceutically acceptable carrier or excipient to prepare a pharmaceutical formulation comprising the antibody.

142. The method of claim 135, wherein the method further comprises combining the recovered antibody with a pharmaceutically acceptable carrier or excipient to prepare a pharmaceutical formulation comprising the antibody.

143. The method of claim 1, wherein at least 60% by molar ratio of the heavy and light chains in the whole cell lysate are folded and assembled to form a biologically active antibody.

144. The method of claim 1, wherein at least 70% by molar ratio of the heavy and light chains in the whole cell lysate are folded and assembled to form a biologically active antibody.

145. The method of claim 1, wherein at least 80% by molar ratio of the heavy and light chains in the whole cell lysate are folded and assembled to form a biologically active antibody.

146. The method of claim 26, wherein at least 60% by molar ratio of the heavy and light chains in the whole cell lysate are folded and assembled to form a biologically active antibody.

147. The method of claim 26, wherein at least 70% by molar ratio of the heavy and light chains in the whole cell lysate are folded and assembled to form a biologically active antibody.

148. The method of claim 26, wherein at least 80% by molar ratio of the heavy and light chains in the whole cell lysate are folded and assembled to form a biologically active antibody.

149. The method of claim 27, wherein at least 60% by molar ratio of the heavy and light chains in the whole cell lysate are folded and assembled to form a biologically active antibody.

150. The method of claim 27, wherein at least 70% by molar ratio of the heavy and light chains in the whole cell lysate are folded and assembled to form a biologically active antibody.

151. The method of claim 27, wherein at least 80% by molar ratio of the heavy and light chains in the whole cell lysate are folded and assembled to form a biologically active antibody.

152. The method of claim 28, wherein at least 60% by molar ratio of the heavy and light chains in the whole cell lysate are folded and assembled to form a biologically active antibody.

153. The method of claim 28, wherein at least 70% by molar ratio of the heavy and light chains in the whole cell lysate are folded and assembled to form a biologically active antibody.

154. The method of claim 28, wherein at least 80% by molar ratio of the heavy and light chains in the whole cell lysate are folded and assembled to form a biologically active antibody.

155. The method of claim 29, wherein at least 60% by molar ratio of the heavy and light chains in the whole cell lysate are folded and assembled to form a biologically active antibody.

156. The method of claim 29, wherein at least 70% by molar ratio of the heavy and light chains in the whole cell lysate are folded and assembled to form a biologically active antibody.

157. The method of claim 29, wherein at least 80% by molar ratio of the heavy and light chains in the whole cell lysate are folded and assembled to form a biologically active antibody.

158. The method of claim 9, wherein at least 60% by molar ratio of the heavy and light chains in the whole cell lysate are folded and assembled to form a biologically active antibody.

159. The method of claim 9, wherein at least 70% by molar ratio of the heavy and light chains in the whole cell lysate are folded and assembled to form a biologically active antibody.

160. The method of claim 9, wherein at least 80% by molar ratio of the heavy and light chains in the whole cell lysate are folded and assembled to form a biologically active antibody.

161. The method of claim 10, wherein at least 60% by molar ratio of the heavy and light chains in the whole cell lysate are folded and assembled to form a biologically active antibody.

162. The method of claim 10, wherein at least 70% by molar ratio of the heavy and light chains in the whole cell lysate are folded and assembled to form a biologically active antibody.

163. The method of claim 10, wherein at least 80% by molar ratio of the heavy and light chains in the whole cell lysate are folded and assembled to form a biologically active antibody.

164. The method of claim 11, wherein at least 60% by molar ratio of the heavy and light chains in the whole cell lysate are folded and assembled to form a biologically active antibody.

165. The method of claim 11, wherein at least 70% by molar ratio of the heavy and light chains in the whole cell lysate are folded and assembled to form a biologically active antibody.

166. The method of claim 11, wherein at least 80% by molar ratio of the heavy and light chains in the whole cell lysate are folded and assembled to form a biologically active antibody.

167. The method of claim 11, wherein the first and second inducible promoters are phoA promoters.

168. The method of claim 26, wherein the first and second inducible promoters are phoA promoters.

169. The method of claim 27, wherein the first and second inducible promoters are phoA promoters.

170. The method of claim 28, wherein the first and second inducible promoters are phoA promoters.

171. The method of claim 29, wherein the first and second inducible promoters are phoA promoters.

172. The method of claim 30, wherein the first and second inducible promoters are phoA promoters.

173. The method of claim 31, wherein the first and second inducible promoters are phoA promoters.

174. The method of claim 32, wherein the first and second inducible promoters are phoA promoters.

175. The method of claim 33, wherein the first and second inducible promoters are phoA promoters.

176. The method of claim 34, wherein the first and second inducible promoters are phoA promoters.

177. The method of claim 35, wherein the first and second inducible promoters are phoA promoters.

178. The method of claim 36, wherein the first and second inducible promoters are phoA promoters.

179. The method of claim 37, wherein the first and second inducible promoters are phoA promoters.

180. The method of claim 167, wherein the method further comprises recovering the antibody from the whole cell lysate.

181. The method of claim 180, wherein the method further comprises combining the recovered antibody with a pharmaceutically acceptable carrier or excipient to prepare a pharmaceutical formulation comprising the antibody.

182. The method of claim 167, wherein at least 60% by molar ratio of the heavy and light chains in the whole cell lysate are folded and assembled to form a biologically active antibody.

183. The method of claim 167, wherein at least 70% by molar ratio of the heavy and light chains in the whole cell lysate are folded and assembled to form a biologically active antibody.

184. The method of claim 167, wherein at least 80% by molar ratio of the heavy and light chains in the whole cell lysate are folded and assembled to form a biologically active antibody.

\* \* \* \* \*

```
                          SEQUENCE LISTING

<160> NUMBER OF SEQ ID NOS: 68

<210> SEQ ID NO 1
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
gcgcgcatta tgaagaaaaa catcgctttt cttcttgcat ctatgttcgt tttttctatt      60
gctacaaacg cttacgct                                                   78

<210> SEQ ID NO 2
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gcgcgcatta tgaaaaaaaa tatagcgttt cttcttgcat ctatgttcgt tttttctatt      60
gctacaaacg cttacgct                                                   78

<210> SEQ ID NO 3
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gcgcgcatta tgaaaaaaaa cattgccttt cttcttgcat ctatgttcgt tttttctatt      60
gctacaaacg cttacgct                                                   78

<210> SEQ ID NO 4
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
gcgcgcatta tgaaaaagaa tattgccttt cttcttgcat ctatgttcgt tttttctatt      60
gctacaaacg cttacgct                                                   78

<210> SEQ ID NO 5
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
```

```
gcgcgcatta tgaagaaaaa tattgcattc cttcttgcat ctatgttcgt tttttctatt      60
gctacaaacg cttacgct                                                    78

<210> SEQ ID NO 6
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
gcgcgcatta tgaaaaaaaa tattgcattt cttcttgcat ctatgttcgt tttttctatt      60
gctacaaacg cttacgct                                                    78

<210> SEQ ID NO 7
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
gcgcgcatta tgaaaaaaaa tattgctttt cttcttgcat ctatgttcgt tttttctatt      60
gctacaaacg cttacgct                                                    78

<210> SEQ ID NO 8
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
acgcgtatta tgaagaaaaa catcgctttt cttcttgcat ctatgttcgt tttttctatt      60
gctacaaacg cttacgct                                                    78

<210> SEQ ID NO 9
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
acgcgtatta tgaaaagaa tatcgccttt cttcttgcat ctatgttcgt tttttctatt       60
gctacaaacg cttacgct                                                    78

<210> SEQ ID NO 10
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
acgcgtatta tgaaaaaaaa tattgctttt cttcttgcat ctatgttcgt tttttctatt      60
gctacaaacg cttacgct                                                    78
```

<210> SEQ ID NO 11
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
gcgcgcatta tgaaaattaa gactggagca cgcatcctcg cattatccgc attaacgacg      60
atgatgtttt ccgcctcggc tctcgcc                                         87

<210> SEQ ID NO 12
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
gcgcgcatta tgaagattaa aaccggagcc cgcatcctcg cattatccgc attaacgacg      60
atgatgtttt ccgcctcggc tctcgcc                                         87

<210> SEQ ID NO 13
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
acgcgtatta tgaagatcaa gacaggcgcg cgcatcctcg cattatccgc attaacgacg      60
atgatgtttt ccgcctcggc tctcgcc                                         87

<210> SEQ ID NO 14
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
acgcgtatta tgaagatcaa gacaggggcc cgcatcctcg cattatccgc attaacgacg      60
atgatgtttt ccgcctcggc tctcgcc                                         87

<210> SEQ ID NO 15
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
tctagaatta tgaaaataaa aacaggtgca cgcatcctcg cattatccgc attaacgacg      60
atgatgtttt ccgcctcggc tctcgcc                                         87

<210> SEQ ID NO 16
<211> LENGTH: 87

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
tctagaatta tgaaaattaa gacgggggcg cgcatcctcg cattatccgc attaacgacg      60
atgatgtttt ccgcctcggc tctcgcc                                         87

<210> SEQ ID NO 17
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
tctagaatta tgaaaatcaa aaccggcgct cgcatcctcg cattatccgc attaacgacg      60
atgatgtttt ccgcctcggc tctcgcc                                         87

<210> SEQ ID NO 18
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
tctagaatta tgaagatcaa gactggagct cgcatcctcg cattatccgc attaacgacg      60
atgatgtttt ccgcctcggc tctcgcc                                         87

<210> SEQ ID NO 19
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
tctagaatta tgaaaataaa gacgggagct cgcatcctcg cattatccgc attaacgacg      60
atgatgtttt ccgcctcggc tctcgcc                                         87

<210> SEQ ID NO 20
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
tctagaatta tgaagataaa gactggtgcg cgcatcctcg cattatccgc attaacgacg      60
atgatgtttt ccgcctcggc tctcgcc                                         87

<210> SEQ ID NO 21
<211> LENGTH: 87
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 21
tctagaatta tgaaaattaa gacgggagca cgcatcctcg cattatccgc attaacgacg    60
atgatgtttt ccgcctcggc tctcgcc                                       87

<210> SEQ ID NO 22
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
tctagaatta tgaagattaa gacgggcgct cgcatcctcg cattatccgc attaacgacg    60
atgatgtttt ccgcctcggc tctcgcc                                       87

<210> SEQ ID NO 23
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
gcgcgcatta tgaaacaatc cacgattgcc ctggcactct taccgttact gtttacccct    60
gtgacaaaag cc                                                       72

<210> SEQ ID NO 24
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
gcgcgcatta tgaaacagtc gacgatcgca ctggcactct taccgttact gtttacccct    60
gtgacaaaag cc                                                       72

<210> SEQ ID NO 25
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
gcgcgcatta tgaaacaaag cactattgca ctggcactct taccgttact gtttaccccct    60 gtgacaaaag cc                                                       72

<210> SEQ ID NO 26
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26

```
gcgcgcatta tgaagcaatc tactatcgct ctggcactct taccgttact gtttacccct    60
gtgacaaaag cc                                                        72

<210> SEQ ID NO 27
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
gcgcgcatta tgaagcaatc aactatcgca ctggcactct taccgttact gtttacccct    60
gtgacaaaag cc                                                        72

<210> SEQ ID NO 28
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
gcgcgcatta tgaaacaatc tactattgca ctggcactct taccgttact gtttacccct    60
gtgacaaaag cc                                                        72

<210> SEQ ID NO 29
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
acgcgtatta tgaaacagtc tactatcgct ctggcactct taccgttact gtttacccct    60
gtgacaaaag cc                                                        72

<210> SEQ ID NO 30
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
tctagaatta tgaagcagag tacgattgct ctggcactct taccgttact gtttacccct    60
gtgacaaaag cc                                                        72

<210> SEQ ID NO 31
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
tctagaatta tgaaacaaag cactattgca ctggcactct taccgttact gtttacccct    60
gtgacaaaag cc                                                        72
```

<210> SEQ ID NO 32
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
tctagaatta tgaagcaatc cacaatagct ctggcactct taccgttact gtttaccccct    60 gtgacaaaag cc                                                         72

<210> SEQ ID NO 33
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
tctagaatta tgaaacaatc caccattgcc ctggcactct taccgttact gtttaccccct    60 gtgacaaaag cc                                                         72

<210> SEQ ID NO 34
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
tctagaatta tgaaacagtc tactatcgcg ctggcactct taccgttact gtttaccccct    60 gtgacaaaag cc                                                         72

<210> SEQ ID NO 35
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
tctagaatta tgaaacaatc cacaatcgca ctggcactct taccgttact gtttaccccct    60 gtgacaaaag cc                                                         72

<210> SEQ ID NO 36
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
gcgcgcatta tgaaaaaaat ttggctcgcc ctggctggtt tagttttagc gtttagcgca    60
tcggcg                                                                66

<210> SEQ ID NO 37
<211> LENGTH: 66
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 37
gcgcgcatta tgaaaaagat ttggctggcg ctggctggtt tagttttagc gtttagcgca    60
tcggcg                                                               66

<210> SEQ ID NO 38
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
gcgcgcatta tgaaaaagat atggctggct ctggctggtt tagttttagc gtttagcgca    60
tcggcg                                                               66

<210> SEQ ID NO 39
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
gcgcgcatta tgaaaaagat atggttggct ctggctggtt tagttttagc gtttagcgca    60
tcggcg                                                               66

<210> SEQ ID NO 40
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
acgcgtatta tgaaaaagat ttggctggcg ctggctggtt tagttttagc gtttagcgca    60
tcggcg                                                               66

<210> SEQ ID NO 41
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
acgcgtatta tgaagaaaat tggttggct ctggctggtt tagttttagc gtttagcgca     60
tcggcg                                                               66

<210> SEQ ID NO 42
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 42
acgcgtatta tgaagaagat ttggttagca ctggctggtt tagtttagc gtttagcgca    60 tcggcg    66

<210> SEQ ID NO 43
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Tyr
            20                  25                  30

Trp Leu His Trp Val Arg Gln Ala Pro Gly Lys Gly Leu Glu Trp Val
        35                  40                  45

Gly Met Ile Asp Pro Ser Asn Ser Asp Thr Arg Phe Asn Pro Asn Phe
    50                  55                  60

Lys Asp Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Thr Tyr Arg Ser Tyr Val Thr Pro Leu Asp Tyr Trp Gly Gln Gly
            100                 105                 110

Thr Leu Val Thr Val Ser Ser
        115
```

<210> SEQ ID NO 44
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

```
Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Tyr Thr
            20                  25                  30

Ser Ser Gln Lys Asn Tyr Leu Ala Trp Tyr Gln Gln Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Tyr Tyr Ala Tyr Pro Trp Thr Phe Gly Gln Gly Thr Lys Val Glu Ile
            100                 105                 110

Lys Arg
```

<210> SEQ ID NO 45
<211> LENGTH: 449

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Tyr
            20                  25                  30

Trp Leu His Trp Val Arg Gln Ala Pro Gly Lys Gly Leu Glu Trp Val
        35                  40                  45

Gly Met Ile Asp Pro Ser Asn Ser Asp Thr Arg Phe Asn Pro Asn Phe
    50                  55                  60

Lys Asp Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Thr Tyr Arg Ser Tyr Val Thr Pro Leu Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Ser
        355                 360                 365

Cys Ala Val Lys Gly Phe Tyr Pro Ser Asp Ile Ala Val Glu Trp Glu
    370                 375                 380

```
Ser Asn Gly Gln Pro Glu Asn Asn Tyr Lys Thr Thr Pro Pro Val Leu
385                 390                 395                 400

Asp Ser Asp Gly Ser Phe Phe Leu Val Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 46
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Tyr Thr
            20                  25                  30

Ser Ser Gln Lys Asn Tyr Leu Ala Trp Tyr Gln Gln Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Tyr Tyr Ala Tyr Pro Trp Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 47
<211> LENGTH: 227
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47
```

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 48
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Asp Ile Cys Leu Pro Arg Trp Gly Cys Leu Trp
1               5                   10

<210> SEQ ID NO 49
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Lys Ser Ser Gln Ser Leu Leu Tyr Thr Ser Ser Gln Lys Asn Tyr Leu
1               5                   10                  15

Ala

<210> SEQ ID NO 50
<211> LENGTH: 7
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 50

Trp Ala Ser Thr Arg Glu Ser
1               5

<210> SEQ ID NO 51
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Gln Gln Tyr Tyr Ala Tyr Pro Trp Thr
1               5

<210> SEQ ID NO 52
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Gly Tyr Thr Phe Thr Ser Tyr Trp Leu His
1               5                   10

<210> SEQ ID NO 53
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Gly Met Ile Asp Pro Ser Asn Ser Asp Thr Arg Phe Asn Pro Asn Phe
1               5                   10                  15

Lys Asp

<210> SEQ ID NO 54
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Thr or Ser

<400> SEQUENCE: 54

Xaa Tyr Gly Ser Tyr Val Ser Pro Leu Asp Tyr
1               5                   10

<210> SEQ ID NO 55
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 55

Thr Tyr Gly Ser Tyr Val Ser Pro Leu Asp Tyr
1               5                   10

<210> SEQ ID NO 56
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Ser Tyr Gly Ser Tyr Val Ser Pro Leu Asp Tyr
1               5                   10

<210> SEQ ID NO 57
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 58
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Trp Tyr Gln Gln Lys Pro Gly Lys Ala Pro Lys Leu Leu Ile Tyr
1               5                   10                  15

<210> SEQ ID NO 59
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 60
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

```
Phe Gly Gln Gly Thr Lys Val Glu Ile Lys Arg
1               5                   10
```

<210> SEQ ID NO 61
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

```
Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105
```

<210> SEQ ID NO 62
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

```
Glu Val Gln Leu Val Glu Ser Gly Gly Gly Leu Val Gln Pro Gly Gly
1               5                   10                  15

Ser Leu Arg Leu Ser Cys Ala Ala Ser
            20                  25
```

<210> SEQ ID NO 63
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

```
Trp Val Arg Gln Ala Pro Gly Lys Gly Leu Glu Trp Val
1               5                   10
```

<210> SEQ ID NO 64
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

```
Arg Phe Thr Ile Ser Ala Asp Thr Ser Lys Asn Thr Ala Tyr Leu Gln
```

```
                1               5                    10                   15
Met Asn Ser Leu Arg Ala Glu Asp Thr Ala Val Tyr Tyr Cys
                20                   25                  30

<210> SEQ ID NO 65
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Trp Gly Gln Gly Thr Leu Val Thr Val Ser Ser
1               5                   10

<210> SEQ ID NO 66
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Ala Thr Tyr Arg Ser Tyr Val Thr Pro Leu Asp Tyr
1               5                   10

<210> SEQ ID NO 67
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr
            100                 105

<210> SEQ ID NO 68
<211> LENGTH: 222
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Cys Pro Pro Cys Pro Ala Pro Glu Leu Leu Gly Gly Pro Ser Val Phe
1               5                   10                  15
```

-continued

```
Leu Phe Pro Pro Lys Pro Lys Asp Thr Leu Met Ile Ser Arg Thr Pro
            20              25              30

Glu Val Thr Cys Val Val Val Asp Val Ser His Glu Asp Pro Glu Val
        35              40              45

Lys Phe Asn Trp Tyr Val Asp Gly Val Glu Val His Asn Ala Lys Thr
    50              55              60

Lys Pro Arg Glu Glu Gln Tyr Asn Ser Thr Tyr Arg Val Val Ser Val
65              70              75              80

Leu Thr Val Leu His Gln Asp Trp Leu Asn Gly Lys Glu Tyr Lys Cys
                85              90              95

Lys Val Ser Asn Lys Ala Leu Pro Ala Pro Ile Glu Lys Thr Ile Ser
            100             105             110

Lys Ala Lys Gly Gln Pro Arg Glu Pro Gln Val Tyr Thr Leu Pro Pro
        115             120             125

Ser Arg Glu Glu Met Thr Lys Asn Gln Val Ser Leu Ser Cys Ala Val
    130             135             140

Lys Gly Phe Tyr Pro Ser Asp Ile Ala Val Glu Trp Glu Ser Asn Gly
145             150             155             160

Gln Pro Glu Asn Asn Tyr Lys Thr Thr Pro Pro Val Leu Asp Ser Asp
                165             170             175

Gly Ser Phe Phe Leu Val Ser Lys Leu Thr Val Asp Lys Ser Arg Trp
            180             185             190

Gln Gln Gly Asn Val Phe Ser Cys Ser Val Met His Glu Ala Leu His
        195             200             205

Asn His Tyr Thr Gln Lys Ser Leu Ser Leu Ser Pro Gly Lys
    210             215             220
```